(12) United States Patent
Kumar et al.

(10) Patent No.: US 10,953,234 B2
(45) Date of Patent: Mar. 23, 2021

(54) WEARABLE DEVICES

(71) Applicant: ELEMENT SCIENCE, INC., San Francisco, CA (US)

(72) Inventors: Uday N. Kumar, San Francisco, CA (US); Timothy Bahney, San Francisco, CA (US); Maarten Dinger, San Francisco, CA (US); Pedram Afshar, Minneapolis, MN (US); Jay Dhuldhoya, San Francisco, CA (US); Riley Marangi, San Francisco, CA (US); Kevin M. Farino, San Francisco, CA (US); Christopher J. Hasser, Los Altos, CA (US); Zachary J. Malchano, San Francisco, CA (US); Frank Garcia, San Francisco, CA (US)

(73) Assignee: ELEMENT SCIENCE, INC., San Francisco, CA (US)

( * ) Notice: Subject to any disclaimer, the term of this patent is extended or adjusted under 35 U.S.C. 154(b) by 32 days.

(21) Appl. No.: 15/755,348

(22) PCT Filed: Aug. 26, 2016

(86) PCT No.: PCT/US2016/049085
§ 371 (c)(1),
(2) Date: Feb. 26, 2018

(87) PCT Pub. No.: WO2017/035502
PCT Pub. Date: Mar. 2, 2017

(65) Prior Publication Data
US 2019/0022400 A1    Jan. 24, 2019

Related U.S. Application Data

(60) Provisional application No. 62/210,369, filed on Aug. 26, 2015, provisional application No. 62/210,873, filed on Aug. 27, 2015.

(51) Int. Cl.
*A61N 1/39* (2006.01)
*A61B 5/046* (2006.01)
(Continued)

(52) U.S. Cl.
CPC .......... *A61N 1/3987* (2013.01); *A61B 5/0205* (2013.01); *A61B 5/046* (2013.01);
(Continued)

(58) Field of Classification Search
USPC .......................................................... 607/7
See application file for complete search history.

(56) References Cited

U.S. PATENT DOCUMENTS 3,706,313 A   12/1972  Milani et al.
3,924,641 A   12/1975  Weiss
(Continued)

FOREIGN PATENT DOCUMENTS

CN      103354756 A    10/2013
EP          95726 B1    11/1988
(Continued)

OTHER PUBLICATIONS

Kumar et al., U.S. Appl. No. 16/598,866 entitled "Wearable Medical device with disposable and reusable components," filed Oct. 10, 2019.
(Continued)

*Primary Examiner* — Nicole F Lavert
(74) *Attorney, Agent, or Firm* — Shay Glenn LLP

(57) ABSTRACT

Wearable devices are provided herein including wearable defibrillators, wearable devices for diagnosing symptoms associated with sleep apnea, and wearable devices for diagnosing symptoms associated with heart failure. The wearable external defibrillators can include a plurality of ECG sensing electrodes and a first defibrillator electrode pad and a second defibrillator electrode pad. The ECG sensing
(Continued)

electrodes and the defibrillator electrode pads are configured for long term wear. Methods are also provided for using the wearable external defibrillators to analyze cardiac signals of the wearer and to provide an electrical shock if a treatable arrhythmia is detected. Methods are also disclosed for refurbishing wearable defibrillators. Methods of using wearable devices for diagnosing symptoms associated with sleep apnea and for diagnosing symptoms associated with heart failure are also provided.

26 Claims, 59 Drawing Sheets

(51) Int. Cl.
| | | |
|---|---|---|
| A61N 1/04 | (2006.01) | |
| A61B 5/0205 | (2006.01) | |
| A61B 5/0408 | (2006.01) | |
| A61B 5/00 | (2006.01) | |
| A61B 5/0468 | (2006.01) | |
| A61B 5/04 | (2006.01) | |
| A61N 1/02 | (2006.01) | |

(52) U.S. Cl.
CPC ........ *A61B 5/04011* (2013.01); *A61B 5/0468* (2013.01); *A61B 5/04087* (2013.01); *A61B 5/4818* (2013.01); *A61B 5/6833* (2013.01); *A61B 5/746* (2013.01); *A61N 1/025* (2013.01); *A61N 1/046* (2013.01); *A61N 1/0492* (2013.01); *A61N 1/3904* (2017.08); *A61N 1/3968* (2013.01); *A61B 2562/0215* (2017.08); *A61N 1/048* (2013.01); *A61N 1/0484* (2013.01); *A61N 1/395* (2013.01); *A61N 1/3925* (2013.01)

(56) References Cited

U.S. PATENT DOCUMENTS

| | | | |
|---|---|---|---|
| 4,023,573 A | 5/1977 | Pantridge et al. | |
| 4,184,493 A | 1/1980 | Langer et al. | |
| 4,328,808 A | 5/1982 | Charbonnier et al. | |
| 4,473,078 A | 9/1984 | Angel | |
| 4,499,907 A | 2/1985 | Kallok et al. | |
| 4,504,773 A | 3/1985 | Suzuki et al. | |
| 4,523,595 A | 6/1985 | Zibell | |
| 4,548,203 A | 10/1985 | Tacker et al. | |
| 4,574,810 A | 3/1986 | Lerman | |
| 4,576,170 A | 3/1986 | Bradley et al. | |
| 4,595,009 A | 6/1986 | Leinders | |
| 4,614,192 A | 9/1986 | Imran et al. | |
| 4,637,397 A | 1/1987 | Jones et al. | |
| 4,706,680 A | 11/1987 | Keusch et al. | |
| 4,708,145 A | 11/1987 | Tacker et al. | |
| 4,727,877 A | 3/1988 | Kallok | |
| 4,768,512 A | 9/1988 | Imran | |
| 4,777,954 A | 10/1988 | Keusch et al. | |
| 4,800,883 A | 1/1989 | Winstrom | |
| 4,821,723 A | 4/1989 | Baker et al. | |
| 4,823,796 A | 4/1989 | Benson | |
| 4,834,100 A | 5/1989 | Charms | |
| 4,850,357 A | 7/1989 | Bach | |
| 4,869,252 A | 9/1989 | Gilli | |
| 4,928,690 A | 5/1990 | Heilman et al. | |
| 4,953,551 A | 9/1990 | Mehra et al. | |
| 4,996,984 A | 3/1991 | Sweeney | |
| 5,014,701 A | 5/1991 | Pless et al. | |
| 4,989,607 A | 12/1991 | Keusch et al. | |
| 5,078,134 A | 1/1992 | Heilman et al. | |
| 5,083,562 A | 1/1992 | de Coriolis et al. | |
| 5,092,332 A | 3/1992 | Lee et al. | |
| 5,107,834 A | 4/1992 | Ideker et al. | |
| 5,111,813 A | 5/1992 | Charbonnier et al. | |
| 5,143,071 A | 9/1992 | Keusch et al. |
| 5,163,427 A | 11/1992 | Keimel |
| 5,172,690 A | 12/1992 | Nappholz et al. |
| 5,174,288 A | 12/1992 | Bardy et al. |
| 5,179,946 A | 1/1993 | Weiss |
| 5,184,616 A | 2/1993 | Weiss |
| 5,205,284 A | 4/1993 | Freeman |
| 5,207,219 A | 5/1993 | Adams et al. |
| 5,222,492 A | 6/1993 | Morgan et al. |
| 5,230,336 A | 7/1993 | Fain et al. |
| 5,251,624 A | 10/1993 | Bocek et al. |
| 5,261,400 A | 11/1993 | Bardy |
| 5,271,417 A | 12/1993 | Swanson et al. |
| 5,292,338 A | 3/1994 | Bardy |
| 5,314,430 A | 5/1994 | Bardy |
| 5,324,309 A | 6/1994 | Kallok |
| 5,334,219 A | 8/1994 | Kroll |
| 5,344,429 A | 9/1994 | Smits |
| 5,352,239 A | 10/1994 | Pless |
| 5,360,435 A | 11/1994 | DeGroot |
| 5,366,484 A | 11/1994 | Kroll |
| 5,366,485 A | 11/1994 | Kroll et al. |
| 5,366,497 A | 11/1994 | Ilvento et al. |
| 5,372,606 A | 12/1994 | Lang et al. |
| 5,381,803 A | 1/1995 | Herleikson et al. |
| 5,391,186 A | 2/1995 | Kroll et al. |
| 5,395,395 A | 3/1995 | Hedberg |
| 5,405,366 A | 4/1995 | Fox et al. |
| 5,411,547 A | 5/1995 | Causey |
| 5,413,591 A | 5/1995 | Knoll |
| 5,431,687 A | 7/1995 | Kroll |
| 5,431,693 A | 7/1995 | Schroeppel |
| 5,439,484 A | 8/1995 | Mehra |
| 5,456,690 A | 10/1995 | Duong Van |
| 5,466,244 A | 11/1995 | Morgan |
| 5,468,254 A | 11/1995 | Hahn et al. |
| 5,474,574 A | 12/1995 | Payne et al. |
| 5,483,165 A | 1/1996 | Cameron et al. |
| 5,489,293 A | 2/1996 | Pless et al. |
| 5,507,778 A | 4/1996 | Freeman |
| 5,540,723 A | 7/1996 | Ideker et al. |
| 5,540,724 A | 7/1996 | Cox |
| 5,545,182 A | 8/1996 | Stotts et al. |
| 5,545,183 A | 8/1996 | Altman |
| 5,578,062 A | 11/1996 | Alt et al. |
| 5,591,211 A | 1/1997 | Meltzer |
| 5,591,212 A | 1/1997 | Keimel |
| 5,594,287 A | 1/1997 | Cameron |
| 5,607,454 A | 3/1997 | Cameron et al. |
| 5,620,467 A | 4/1997 | Wagner |
| 5,622,168 A | 4/1997 | Keusch et al. |
| 5,632,267 A | 5/1997 | Hognelid et al. |
| 5,643,324 A | 7/1997 | Persson |
| 5,650,750 A | 7/1997 | Leyde et al. |
| 5,658,319 A | 8/1997 | Kroll |
| 5,662,690 A | 9/1997 | Cole et al. |
| 5,670,557 A | 9/1997 | Dietz et al. |
| 5,674,250 A | 10/1997 | de Coriolis et al. |
| 5,674,275 A | 10/1997 | Tang et al. |
| 5,683,424 A | 11/1997 | Brown et al. |
| 5,718,718 A | 2/1998 | Kroll et al. |
| 5,720,767 A | 2/1998 | Amely Velez |
| 5,725,560 A | 3/1998 | Brink |
| 5,735,879 A | 4/1998 | Gliner et al. |
| 5,741,306 A | 4/1998 | Glegyak et al. |
| 5,766,226 A | 6/1998 | Pedersen |
| 5,769,872 A | 6/1998 | Lopin et al. |
| 5,792,188 A | 8/1998 | Starkweather et al. |
| 5,803,927 A | 9/1998 | Cameron et al. |
| 5,824,017 A | 10/1998 | Sullivan et al. |
| 5,824,018 A | 10/1998 | Dreher et al. |
| 5,833,712 A | 11/1998 | Kroll et al. |
| 5,849,025 A | 12/1998 | Owens et al. |
| 5,889,388 A | 3/1999 | Cameron et al. |
| 5,891,173 A | 4/1999 | Brewer |
| D409,752 S | 5/1999 | Bishay et al. |
| 5,902,249 A | 5/1999 | Lyster |
| 5,902,323 A | 5/1999 | Brewer et al. |
| 5,908,443 A | 6/1999 | Brewer et al. |

(56) References Cited

U.S. PATENT DOCUMENTS

| | | |
|---|---|---|
| 5,928,270 A | 7/1999 | Ramsey |
| 5,929,601 A | 7/1999 | Kaib et al. |
| 5,944,669 A | 8/1999 | Kaib |
| 5,951,598 A | 9/1999 | Bishay et al. |
| 5,974,339 A | 10/1999 | Baker et al. |
| 5,978,705 A | 11/1999 | KenKnight et al. |
| 5,987,354 A | 11/1999 | Cooper et al. |
| 5,991,658 A | 11/1999 | Brewer et al. |
| 6,041,255 A | 3/2000 | Kroll |
| 6,065,154 A | 5/2000 | Hulings et al. |
| 6,093,982 A | 7/2000 | Kroll |
| 6,097,982 A | 8/2000 | Glegyak et al. |
| 6,101,413 A | 8/2000 | Olson et al. |
| 6,104,953 A | 8/2000 | Leyde |
| 6,108,578 A | 8/2000 | Bardy et al. |
| 6,119,039 A | 9/2000 | Leyde |
| 6,125,298 A | 9/2000 | Olson et al. |
| 6,128,531 A | 10/2000 | Campbell Smith |
| 6,134,479 A | 10/2000 | Brewer et al. |
| 6,148,222 A | 11/2000 | Ramsey |
| 6,169,387 B1 | 1/2001 | Kaib |
| 6,173,204 B1 | 1/2001 | Sullivan et al. |
| 6,208,896 B1 | 3/2001 | Mulhauser |
| 6,208,898 B1 | 3/2001 | Gliner et al. |
| 6,219,222 B1 | 4/2001 | Shah et al. |
| 6,230,054 B1 | 5/2001 | Powers |
| 6,234,990 B1 | 5/2001 | Rowe et al. |
| 6,241,751 B1 | 6/2001 | Morgan et al. |
| 6,253,099 B1 | 6/2001 | Oskin et al. |
| 6,280,461 B1 | 8/2001 | Glegyak et al. |
| 6,289,243 B1 | 9/2001 | Lin et al. |
| 6,298,267 B1 | 10/2001 | Rosborough et al. |
| 6,304,773 B1 | 10/2001 | Taylor et al. |
| 6,304,783 B1 | 10/2001 | Lyster et al. |
| 6,327,499 B1 | 12/2001 | Alt |
| 6,337,995 B1 | 1/2002 | Mower |
| 6,347,248 B1 | 2/2002 | Gliner |
| 6,411,844 B1 | 6/2002 | Kroll et al. |
| 6,421,563 B1 | 7/2002 | Sullivan et al. |
| 6,441,582 B1 | 8/2002 | Powers |
| 6,451,947 B1 | 9/2002 | Benz et al. |
| 6,480,734 B1 | 11/2002 | Zhang et al. |
| 6,490,478 B1 | 12/2002 | Zhang et al. |
| 6,496,729 B2 | 12/2002 | Thompson |
| 6,539,255 B1 | 3/2003 | Brewer et al. |
| 6,539,258 B1 | 3/2003 | Sullivan et al. |
| 6,546,285 B1 | 4/2003 | Owen et al. |
| 6,546,287 B1 | 4/2003 | Havel et al. |
| 6,549,807 B1 | 4/2003 | Kroll |
| 6,556,863 B1 | 4/2003 | O'Phelan et al. |
| 6,597,949 B1 | 7/2003 | Dhurjaty |
| 6,625,487 B2 | 9/2003 | Herleikson |
| 6,633,778 B2 | 10/2003 | Sherman |
| 6,647,290 B2 | 11/2003 | Wuthrich |
| 6,678,559 B1 | 1/2004 | Breyen et al. |
| 6,681,003 B2 | 1/2004 | Linder et al. |
| 6,687,117 B2 | 2/2004 | Liu et al. |
| 6,738,664 B1 | 5/2004 | McDaniel |
| 6,760,621 B2 | 7/2004 | Walcott et al. |
| 6,766,193 B1 | 7/2004 | Mouchawar et al. |
| 6,834,050 B1 | 12/2004 | Madour et al. |
| 6,856,835 B2 | 2/2005 | Bardy et al. |
| 6,871,094 B1 | 3/2005 | Allen et al. |
| 6,873,133 B1 | 3/2005 | Kavounas |
| 6,873,874 B2 | 3/2005 | Ware et al. |
| 6,954,669 B1 | 10/2005 | Fishler et al. |
| 6,963,773 B2 | 11/2005 | Waltman et al. |
| 6,965,796 B2 | 11/2005 | Kelly |
| 6,965,799 B2 | 11/2005 | Nova et al. |
| 6,968,230 B2 | 11/2005 | Waltman |
| 6,980,856 B2 | 12/2005 | Sullivan et al. |
| 6,983,183 B2 | 1/2006 | Thiagarajan et al. |
| 6,990,373 B2 | 1/2006 | Jayne et al. |
| 6,993,386 B2 | 1/2006 | Lin et al. |
| 6,996,436 B2 | 2/2006 | Allen et al. |
| 7,006,865 B1 | 2/2006 | Cohen et al. |
| 7,027,864 B2 | 4/2006 | Snyder et al. |
| 7,047,072 B2 | 5/2006 | Walker et al. |
| 7,050,850 B2 | 5/2006 | Norton |
| 7,054,686 B2 | 5/2006 | MacDonald |
| 7,062,321 B2 | 6/2006 | Lyster et al. |
| 7,079,894 B2 | 7/2006 | Lyster et al. |
| 7,085,601 B1 | 8/2006 | Bardy et al. |
| 7,095,210 B2 | 8/2006 | Tamura et al. |
| 7,096,062 B2 | 8/2006 | Kelly et al. |
| 7,107,099 B1 | 9/2006 | O'Phelan et al. |
| 7,149,576 B1 | 12/2006 | Baura et al. |
| 7,151,963 B2 | 12/2006 | Havel et al. |
| 7,174,204 B2 | 2/2007 | Hadley et al. |
| 7,174,208 B2 | 2/2007 | DeGroot et al. |
| 7,194,303 B2 | 3/2007 | Rissmann et al. |
| 7,200,434 B2 | 4/2007 | Havel et al. |
| 7,242,979 B1 | 7/2007 | Kelly et al. |
| 7,245,974 B2 | 7/2007 | Dupelle et al. |
| 7,257,441 B2 | 8/2007 | Swerdlow et al. |
| 7,272,441 B1 | 9/2007 | Chapman et al. |
| 7,277,751 B2 | 10/2007 | Dupelle et al. |
| 7,379,772 B2 | 5/2008 | Bardy et al. |
| 7,383,085 B2 | 6/2008 | Olson |
| 7,385,802 B1 | 6/2008 | Ribble et al. |
| 7,392,081 B2 | 6/2008 | Wagner et al. |
| 7,463,923 B2 | 12/2008 | Brewer et al. |
| 7,570,994 B2 | 8/2009 | Tamura et al. |
| 7,570,996 B2 | 8/2009 | Crespi et al. |
| 7,667,954 B2 | 2/2010 | Lessner et al. |
| 7,684,864 B2 | 3/2010 | Olson et al. |
| 7,706,864 B2 | 4/2010 | Kroll et al. |
| 7,729,770 B2 | 6/2010 | Cabelka et al. |
| 7,734,345 B2 | 6/2010 | Cinbis |
| 7,840,265 B2 | 11/2010 | Perschbacher et al. |
| 7,920,918 B2 | 4/2011 | Ideker et al. |
| 7,962,207 B2 | 6/2011 | Nassif |
| 7,974,689 B2 | 7/2011 | Volpe et al. |
| 8,000,786 B2 | 8/2011 | Sweeney |
| 8,024,037 B2 | 9/2011 | Kumar |
| 8,050,759 B2 | 11/2011 | Stegemann et al. |
| 8,086,312 B2 | 12/2011 | Nielsen et al. |
| 8,108,043 B2 | 1/2012 | Markowitz et al. |
| 8,116,865 B2 | 2/2012 | Linder et al. |
| 8,121,683 B2 | 2/2012 | Bucher et al. |
| 8,145,303 B2 | 3/2012 | Rubin et al. |
| 8,195,280 B2 | 6/2012 | Van Dam et al. |
| 8,209,007 B2 | 6/2012 | McIntyre et al. |
| 8,239,012 B2 | 8/2012 | Felix et al. |
| 8,343,644 B2 | 1/2013 | Vaisnys et al. |
| 8,364,260 B2 | 1/2013 | Kumar |
| 8,369,945 B2 | 2/2013 | Youker et al. |
| 8,386,035 B2 | 2/2013 | Vaisnys et al. |
| 8,401,637 B2 | 3/2013 | Kroll et al. |
| 8,401,638 B2 | 3/2013 | Swerdlow et al. |
| 8,423,136 B2 | 4/2013 | Ostroff |
| 8,433,404 B2 | 4/2013 | Chavan et al. |
| 8,473,051 B1 | 6/2013 | Wessels et al. |
| 8,706,215 B2 | 4/2014 | Kaib et al. |
| 8,838,236 B2 | 9/2014 | Debardi et al. |
| 9,101,780 B2 | 8/2015 | Cheng et al. |
| 9,237,858 B2 | 1/2016 | Krusor et al. |
| 9,592,403 B2 | 3/2017 | Sullivan |
| 9,597,004 B2 | 3/2017 | Hughes et al. |
| 9,724,008 B2 | 8/2017 | Sullivan et al. |
| 9,757,580 B2 | 9/2017 | Park et al. |
| 9,757,581 B2 | 9/2017 | Sullivan et al. |
| 9,767,679 B2 | 9/2017 | Foshee et al. |
| 9,789,327 B2 | 10/2017 | Brown et al. |
| 9,827,434 B2 | 11/2017 | Kaib et al. |
| 9,833,607 B2 | 12/2017 | Crone et al. |
| 9,968,789 B2 | 5/2018 | Karl et al. |
| 10,052,043 B2 | 8/2018 | Kaib et al. |
| 10,105,547 B2 | 10/2018 | Gustavson et al. |
| 10,252,070 B2 | 4/2019 | Kaib et al. |
| 10,271,754 B2 | 4/2019 | Bahney et al. |
| 10,322,291 B2 | 6/2019 | Medema et al. |
| 10,328,275 B2 | 6/2019 | Donnelly et al. |
| 2003/0055460 A1 | 3/2003 | Owen et al. |

(56) References Cited

U.S. PATENT DOCUMENTS

| | | |
|---|---|---|
| 2003/0095648 A1 | 5/2003 | Kaib et al. |
| 2003/0125771 A1 | 7/2003 | Garrett |
| 2003/0167075 A1 | 9/2003 | Fincke |
| 2003/0201752 A1 | 10/2003 | Locke et al. |
| 2004/0143297 A1 | 7/2004 | Ramsey |
| 2004/0267322 A1 | 12/2004 | Kavounas et al. |
| 2005/0070963 A1 | 3/2005 | Wilson et al. |
| 2005/0090868 A1 | 4/2005 | Cansell |
| 2005/0107833 A1 | 5/2005 | Freeman et al. |
| 2005/0131465 A1 | 6/2005 | Freeman et al. |
| 2005/0234515 A1 | 10/2005 | Freeman |
| 2006/0116724 A1 | 6/2006 | Snyder |
| 2006/0129192 A1 | 6/2006 | Greatbatch et al. |
| 2006/0149346 A1 | 7/2006 | Dupelle et al. |
| 2006/0173499 A1 | 8/2006 | Hampton et al. |
| 2006/0178706 A1 | 8/2006 | Lisogurski et al. |
| 2006/0229679 A1 | 10/2006 | Joo |
| 2006/0241700 A1 | 10/2006 | Ghanem et al. |
| 2006/0259091 A1 | 11/2006 | Ries et al. |
| 2007/0100381 A1 | 5/2007 | Snyder et al. |
| 2008/0177342 A1 | 7/2008 | Snyder |
| 2008/0183230 A1 | 7/2008 | Kemmetmueller et al. |
| 2008/0255625 A1 | 10/2008 | Powers |
| 2008/0312708 A1 | 12/2008 | Snyder |
| 2009/0005827 A1 | 1/2009 | Weintraub et al. |
| 2009/0076345 A1 | 3/2009 | Manicka et al. |
| 2009/0076559 A1 | 3/2009 | Libbus et al. |
| 2009/0306730 A1 | 12/2009 | Roso |
| 2010/0030290 A1 | 2/2010 | Bonner et al. |
| 2010/0241181 A1 | 9/2010 | Savage et al. |
| 2010/0292544 A1 | 11/2010 | Sherman et al. |
| 2011/0071611 A1 | 3/2011 | Khuon et al. |
| 2011/0125040 A1 | 5/2011 | Crawford et al. |
| 2011/0279963 A1 | 11/2011 | Kumar et al. |
| 2011/0288604 A1 | 11/2011 | Kaib et al. |
| 2012/0046706 A1 | 2/2012 | Anderson et al. |
| 2012/0089037 A1 | 4/2012 | Bishay et al. |
| 2012/0116472 A1 | 5/2012 | Pittaro |
| 2012/0169287 A1 | 7/2012 | Lopin et al. |
| 2012/0191149 A1 | 7/2012 | Freeman |
| 2012/0197353 A1 | 8/2012 | Donnelly et al. |
| 2012/0215123 A1 | 8/2012 | Kumar et al. |
| 2012/0265264 A1 | 10/2012 | Vaisnys et al. |
| 2012/0289809 A1 | 11/2012 | Kaib et al. |
| 2012/0302860 A1 | 11/2012 | Volpe et al. |
| 2012/0325096 A1 | 12/2012 | Holt |
| 2013/0018432 A1 | 1/2013 | Garrett et al. |
| 2013/0053909 A1 | 2/2013 | Elghazzawi et al. |
| 2013/0085538 A1 | 4/2013 | Volpe et al. |
| 2013/0123870 A1 | 5/2013 | Heinrich et al. |
| 2013/0158614 A1 | 6/2013 | Azar et al. |
| 2013/0325096 A1 | 12/2013 | Dupelle et al. |
| 2014/0025131 A1 | 1/2014 | Sullivan et al. |
| 2014/0243694 A1 | 8/2014 | Baker et al. |
| 2014/0277226 A1 | 9/2014 | Poore et al. |
| 2014/0364918 A1* | 12/2014 | Owen .................. A61N 1/0452 607/6 |
| 2014/0371806 A1 | 12/2014 | Raymond et al. |
| 2015/0148854 A1 | 5/2015 | Whiting et al. |
| 2015/0217121 A1 | 8/2015 | Subramanian et al. |
| 2015/0238094 A1 | 8/2015 | Lai et al. |
| 2017/0056682 A1 | 3/2017 | Kumar et al. |

FOREIGN PATENT DOCUMENTS

| | | |
|---|---|---|
| EP | 362093 A2 | 4/1990 |
| EP | 445800 A1 | 9/1991 |
| EP | 487776 A1 | 6/1992 |
| EP | 612253 A1 | 8/1994 |
| EP | 503778 B1 | 7/1996 |
| EP | 469817 B1 | 2/1997 |
| EP | 465241 B1 | 11/1998 |
| EP | 589251 B1 | 11/2000 |
| EP | 1263497 A1 | 12/2002 |
| EP | 988087 B1 | 1/2003 |
| EP | 998328 B1 | 10/2003 |
| EP | 687479 B1 | 8/2004 |
| EP | 973582 B1 | 5/2005 |
| EP | 888149 B1 | 7/2005 |
| EP | 1742700 A2 | 1/2007 |
| EP | 1759732 A1 | 3/2007 |
| EP | 1827594 A1 | 9/2007 |
| EP | 1954345 A2 | 8/2008 |
| EP | 2047886 A1 | 4/2009 |
| EP | 1530983 B1 | 9/2009 |
| EP | 2446927 A1 | 5/2012 |
| JP | H06105917 A | 4/1994 |
| JP | H07541 A | 1/1995 |
| JP | 2002-514107 | 5/2002 |
| JP | 2014533525 A | 12/2014 |
| JP | 2015521085 A | 7/2015 |
| WO | WO97/031680 A1 | 9/1997 |
| WO | WO2001/085251 A1 | 11/2001 |
| WO | WO2006/115778 A2 | 11/2006 |
| WO | WO2007/113452 A1 | 10/2007 |
| WO | WO2011/163339 A1 | 12/2011 |
| WO | WO2013/033238 A1 | 3/2013 |
| WO | WO2013/181607 A1 | 12/2013 |
| WO | WO2014/151925 A1 | 9/2014 |
| WO | WO2015/017727 A1 | 2/2015 |

OTHER PUBLICATIONS

Kumar et al.; U.S. Appl. No. 16/721,506 etitled "External Defibrillator" filed Dec. 19, 2019.

Birgersdotter-Green; Advances in AEDs and wearable defibrillators (presentation slides); 23 pages; 2013 (year of pub. sufficiently earlier than effective US filing date and any foreign priority date; available to applicants(s) at least as of Jun. 4, 2013).

Calle et al.; Equivalence of the standard monophasic waveform shocks delivered by automated external defibrillators; Resuscitation; 53(1); pp. 41-46; Apr. 2002.

Field et al.; Part 1: Executive Summary: 2010 American heart association guidelines for cardiopulmonary resuscitation and emergency cardiovascular care; Circulation; 122 (18 Suppl. 3); pp. S640-S656; Nov. 2, 2010.

Jones et al.; improved safety factor for triphasic defibrillator waveforms; Cir. Res.; 64(6); pp. 1172-1177; Jun. 1989.

Jones et al.; Increasing fibrillation duration enhances relative asymmetrical biphasic versus monophasic defibrillator waveform efficacy; Circ. Res.; 67(2); pp. 376-384; Aug. 1990.

Pariaut et al; Evaluation of shock waveform configuration on the defibrillation capacity of implantable cardioverter defibrillators in dogs; J. Vet. Cardiol.; 14(3); pp. 389-398; Sep. 2012.

Swartz et al.; Conditioning prepulse of biphasic defibrillator waveforms enhances refractoriness to fibrillation wavefronts; Circulation Res.; 68(2); pp. 438-449; Feb. 1991.

Walsh et al.; Novel rectangular biphasic and monophasic waveforms delivered by a radiofrequency-powered defibrillator compared with conventional capacitor-based waveforms in transvenous cardioversion of atrial fibrillation; Europace; 8(10); pp. 873-880; Oct. 2006.

Zipes et al.; ACC/AHA/ESC 2006 guidelines for management of patients with ventricular arrhythmias and the prevention of sudden cardiac death; Europace; 8(9); pp. 746-837; Sep. 2006.

* cited by examiner

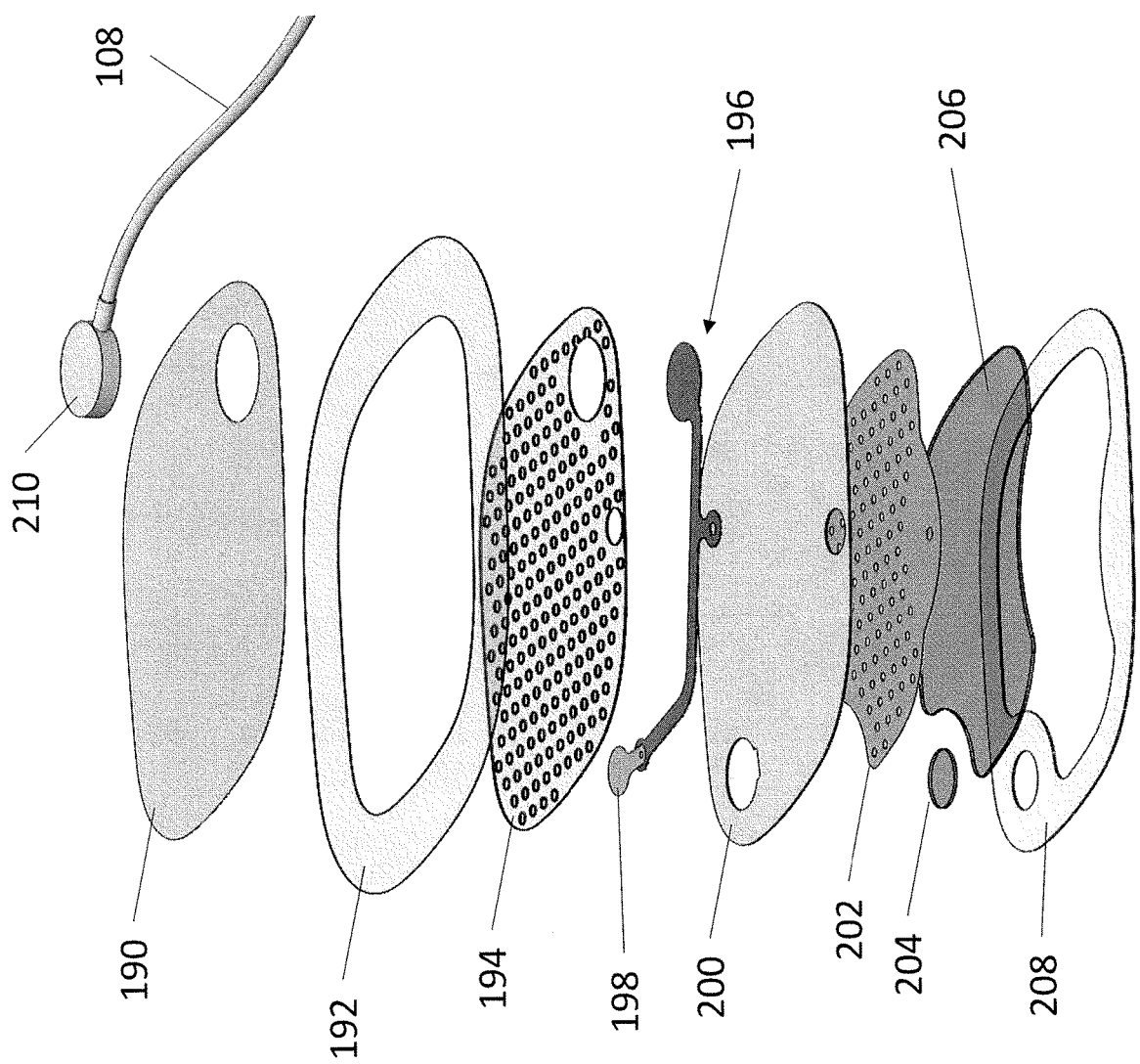

302: Adhering to a first skin surface portion of the patient a first patient engagement substrate comprising a first plurality of sensing electrodes and a first defibrillator electrode pad in electrical communication with an electrical energy source sufficient to provide a defibrillating shock, the first patient engagement substrate part of a wearable defibrillator comprising a fluid transport element configured to transport fluid away from the first skin surface portion of the patient to allow the wearable external defibrillator to be worn continuously 304: Adhering to a second skin surface portion of the patient a second patient engagement substrate comprising a sensing electrode and a second defibrillator electrode pad, the second defibrillator electrode pad in electrical communication with the electrical energy source sufficient to provide the defibrillating shock, the second patient engagement substrate part of the wearable defibrillator, the wearable defibrillator including one or more sensors adapted to detect one or more of the pulse, oxygen content of the blood, impedance, galvanic skin impedance, temperature, breathing rate, heart sounds, and heart rate of the patient 306: Measuring patient data corresponding to a cardiac signal or other characteristic of the patient with the first plurality of sensing electrodes, the sensing electrode of the second patient engagement substrate, and/or the sensors of the wearable defibrillator 308: Analyzing the patient data to determine if the patient has an arrhythmia

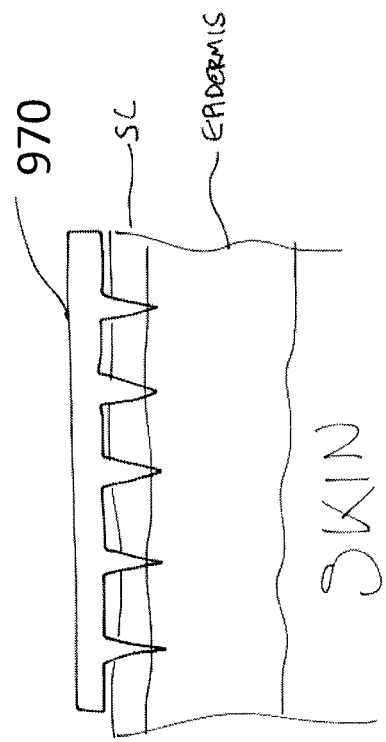
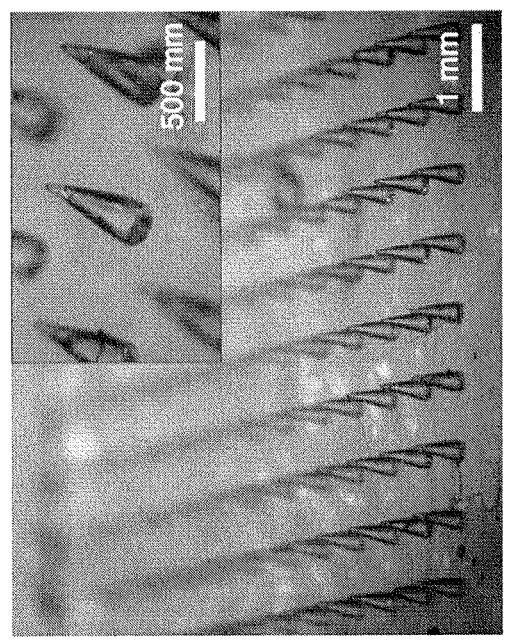
FIG. 36

1122 — Providing instructions on where to put a first patient engagement substrate of the wearable defibrillator on a chest of the patient, the first patient engagement substrate including one or more sensing electrodes, adhesive, and a first defibrillator electrode pad, the instructions including where to put the one or more sensing electrodes and first defibrillator electrode pad on the torso of the patient

→

1124 — Providing instructions on where to put a second patient engagement substrate of the wearable defibrillator, the second patient engagement substrate including a sensing electrode, adhesive, and a second defibrillator electrode pad, the instructions including where to put the one or more sensing electrodes and second defibrillator electrode pad

→

1126 — Verifying a first patient engagement substrate placement on the torso of the patient including the placement of the one or more sensing electrodes and first defibrillator electrode pad

→

1128 — Verifying a second patient engagement substrate placement on the chest of the patient including the sensing electrode and second defibrillator electrode pad.

WEARABLE DEVICES

CROSS REFERENCE TO RELATED APPLICATIONS

The present application claims priority under 35 U.S.C. 119 to U.S. provisional patent application Ser. No. 62/210,369 filed on Aug. 26, 2015 titled "Wearable Defibrillator" and U.S. Provisional Patent Application No. 62/210,873 filed on Aug. 27, 2015 titled "Wearable Defibrillator", the disclosures of each of which are herein incorporated by reference in their entirety.

The present application is related to U.S. Provisional Patent Application No. 61/944,008 filed on Feb. 24, 2014, and International Patent Application No. PCT/US2015/017366 filed on Feb. 24, 2015, each titled "External Defibrillator," the disclosures of which are both incorporated by reference in their entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The present disclosure relates generally to wearable devices, such as external defibrillators. In particular, the disclosure relates to automatic external defibrillators that can be continuously and comfortably worn by a patient for an extended period of time.

BACKGROUND

Every year in the US, over 800,000 individuals have a heart attack, or myocardial infarction (MI). After an MI, a patient is at increased risk for experiencing potentially life-threatening abnormal heart rhythms, or arrhythmias. This increased risk is caused by numerous structural and electrical abnormalities in the recently damaged heart. For most patients, however, this increased risk is temporary. After patients have been treated with various procedures and medications to help their heart heal, their risk of experiencing a life-threatening arrhythmia usually drops back to their risk prior to the MI. This drop in risk typically occurs after a few days to weeks after the MI has taken place.

In addition to the post-MI setting, there are other situations in which a patient's arrhythmia risk is temporarily increased, such as after certain types of heart surgery or when starting certain medications with pro-arrhythmic properties. In patients who are known to be at risk for an arrhythmia and who have an ICD or S-ICD in place, if the ICD/S-ICD needs to be removed for a short period of time due to an infection or malfunction, the patient is also left vulnerable. In other patients, such as those with a condition known as heart failure (new diagnosis or acute exacerbation) or cardiomyopathy, certain medications and/or procedures can lead to an improvement in the heart's function and reduce a patient's susceptibility to an arrhythmia such that a permanently implanted device, such as an ICD or S-ICD, would not be needed. However, during the time of treatment when heart function is recovering or when the patient is receiving treatment, these patients are still temporarily at risk for a life-threatening arrhythmia.

More than 750,000 patients are at risk for sudden cardiac death (SCD) in the U.S. each year. Based on event rates of up to 4% in the higher risk subgroups of the populations improved treatments could save up to 30,000 lives annually in the U.S. There are about 3.7 million worldwide incidence of SCD due to ventricular arrhythmias with a survival rate of less than 1%. Improved methods and devices are also needed to treat patients at risk for SCD. The devices and methods disclosed herein can be used for patients with a temporarily increased risk for SCD or with a chronically increased risk for SCD. Clinical conditions in which a patient's temporary risk for experiencing a lethal arrhythmia or SCD is elevated include, but are not limited to: in patients after explanation of an ICD or S-ICD (due to infection or a mechanical failure, for instance), in patients with sleep apnea when it is severe, in patients who have certain arrhythmia syndromes, in pediatric patients with structural heart diseases, in certain patients with significant valvular heart disease, in pregnant or recently pregnancy patients who develop pregnancy-related cardiomyopathy, and in patients with end-stage renal disease or on dialysis. Additional examples of conditions that can cause, increase the likelihood of SCD, or make a patient prone to SCD include: after cardiac surgery, new cardiomyopathy, after a heart attack, new heart failure, and heart failure exacerbation.

Various studies of this population of patients have shown that certain medications, especially those with anti-arrhythmic properties, do a poor job at reducing this temporarily increased arrhythmia risk. Implantable cardioverter defibrillators (ICDs) and subcutaneous ICD (S-ICDs), which can continuously monitor the patient for an arrhythmia and effectively reset the heart rhythm when an arrhythmia occurs, carry significant risks during implantation such that their overall benefit during this short period of increased risk is limited. Implanting ICDs and S-ICDs in many patients whose risk of an arrhythmia would eventually return to normal also has significant unwanted health, economic, and societal consequences.

Automatic external defibrillators (AEDs) are stored on walls apart from patients in highly populated places such as airports and do not monitor patients for arrhythmias. They are only useful if an AED is present when the patient needs it and if other people capable of using the AED are present at the time an arrhythmia occurs, can identify that a patient needs defibrillation and is able to apply the sensing and defibrillation electrodes to the patient. Wearable external defibrillators and external cardioverter defibrillators are described in U.S. Pat. Nos. 5,741,306; 6,065,154; 6,280,461; 6,681,003 and US 2003/0095648. A similar product is currently being sold as the Zoll Lifecor LifeVest™ wearable cardioverter defibrillator (WCD). Wearable cardioverter defibrillators are able to monitor a patient for arrhythmias while they are worn without the need for implantation surgery, and they can be removed when the need for such monitoring (and possible cardioversion or defibrillation shock) has passed.

One drawback of currently available wearable defibrillators (such as the LifeVest product) is lack of patient compliance. Because of the size, shape and weight of these wearable devices, patients are reluctant to wear them due to discomfort, their bulkiness under clothes or limitations in the devices themselves. In particular, such devices cannot be worn in the shower or bath, and they often are difficult, if not impossible, to sleep in. The device therefore is not useful in providing treatment to the patient while sleeping or in the shower. Patients also complain that the LifeVest is too large and uncomfortable. Many patients also have increased anxiety over the many alarms and notifications from the LifeVest. The increased anxiety further increases instances of non-compliance. Given the bulkiness of these devices, some patients do not like using these wearable devices outside in public as it draws unnecessary attention to them, which they might find uncomfortable or embarrassing. This may affect their well-being and may lead them to avoid performing their normal routine activities. All of these factors increase patient noncompliance and prevent the treatment of a treatable arrhythmia. In one study 60% of LifeVest wearers were not saved due to patient non-compliance (Tanawuttiwat T, et al. PACE Online Dec. 3, 2013). The device can also be easily taken off, which prevents the vest from providing treatment to the patient when it is not being worn.

Another drawback is that it is possible to incorrectly wear a wearable vest like the LifeVest, such that the vest will not properly detect a patient arrhythmia. Incorrectly wearing the vest can also prevent the vest from delivering a defibrillating shock to the patient. The design of the vest can also result in increased false positives of arrhythmias measured by the vest. The vest also has a complicated electrode design. Because the vest is put and taken off multiple times a day, no gel is applied between the defibrillation electrodes and the patient's skin unless and until a shock is required. The gel releasing mechanism can fail or may not work when the vest is worn incorrectly.

What is needed, therefore, is a non-invasive, temporary device that can continuously monitor the patient's heart rhythm to detect arrhythmias; can record and store all detected rhythms for future evaluation if necessary; can automatically and reliably defibrillate the heart if an arrhythmia is detected; can be used for a short period of time (days to weeks, possibly months) when the temporary risk of an arrhythmia exists; is entirely non-invasive and reversible and causes no significant or potentially permanent bodily harm from its use; and/or, most importantly, is unobtrusive and water resistant and requires only minimal maintenance or care so that it can seamlessly integrate into patients' lives such that they are protected from life-threatening arrhythmias during this entire period of time and can perform their normal daily routines without impediments to their physical or mental well-being. If the device is required to defibrillate a patient during this time, this patient can then be referred for evaluation to determine whether they need a permanent ICD or S-ICD, if appropriate. If nothing occurs and the patient doesn't have persistent pro-arrhythmic risk factors after this temporary period, the device can be removed and the implantation of a permanent device can be avoided. In this way, a functional, easy-to-use device for cardiac defibrillation to protect patients during a period of temporarily increased arrhythmia risk could also more efficiently identify patients who would benefit from more permanently implanted devices and those who would not.

A need also exists for treating temporary periods of elevated risk for sudden cardiac death in a successful and cost-effective manner while delivering an outstanding patient experience. A need also exists for improved treatment for patients with a need for an ICD but not getting one today, patients not initially indicated for ICD but found to be at elevated risk for SCD, and patients that would die of SCD without wearable defibrillator.

U.S. Pat. Nos. 8,024,037 and 8,364,260 disclose wearable external defibrillators. Wearable external defibrillators are desired that have improved adhesives for long term-wear, improved electrodes for long-term wear, improved weight distribution of the electrical components, improved and reduced size, and improved comfort to increase patient compliance.

The Zio® Patch by iRhythm® is designed to record heartbeats for up to 14 days. The Zio Patch has a relatively small profile and is lightweight because it does not have to accommodate the electrodes for delivering a defibrillating shock or support the electronic components required to deliver a defibrillating shock.

There are many challenges in developing biocompatible adhesives and electrodes for long-term wear. It is difficult to design adhesives that can be worn for longer than 10 days. Skin sloughing also occurs naturally over time, typically on the order of about 10-30 days, with variation related to the age of the patient. The natural sloughing of skin cells also presents technical challenges that need to be solved by the design of the adhesive material and design of the electrodes. Adhesives and electrodes also typically will cause skin irritation and redness during long term wear. It is desirable to also develop an improved adhesive and electrode design that can be used to comfortably attach the wearable defibrillator to the patient for long term wear. Developing a device that also is small enough to allow a weight distribution while adhered to the patients such that the device can be used constantly for long term wear is a challenging task. Additionally, developing a device small enough to be concealed such that its use in public does not draw attention or can be easily hidden under normal clothing is desired.

SUMMARY OF THE DISCLOSURE

The present invention relates generally to improved wearable devices and methods for using such wearable devices. Examples of wearable devices include wearable defibrillators, wearable devices for diagnosing symptoms associated with sleep apnea, and wearable devices for diagnosing symptoms associated with heart failure. The wearable devices disclosed herein can be comfortably worn by the patient around the clock. The wearable devices, including the wearable defibrillators, can be worn during showering, sleeping, and normal activities. The adhesives and electrodes are designed for long term wear. In the wearable defibrillators the electrodes are designed to be worn such that the electrodes are in continuous electrical communication with the skin and are ready to deliver an effective amount of energy for defibrillation.

In general, in one embodiment, a wearable external defibrillator including one or more sensing electrodes configured to engage with a patient's skin to detect a cardiac signal; a first defibrillator electrode pad configured to engage with the patient's skin and to deliver an electrical therapy to the patient, the first defibrillator electrode pad configured to be in continuous contact with the patient's skin; a first patient engagement substrate including an adhesive, the first defibrillator electrode pad, a first fluid transport element configured to transport fluid away from the skin to allow the wearable external defibrillator to be worn continuously, and a first vapor permeable layer; a second patient engagement substrate including a second defibrillator electrode pad, a second adhesive, a second fluid transport element in fluid communication with the second patient engagement substrate configured to transport fluid away from the skin to allow the wearable external defibrillator to be worn continuously, and a second vapor permeable layer; an energy source; one or more capacitors in electrical communication with the energy source and the first defibrillator electrode pad and the second defibrillator electrode pad; and a controller configured to detect the cardiac signal with the one or more sensing electrodes and the sensing electrode of the second patient engagement substrate and to charge the one or more capacitors with the energy source followed by discharging the one or more capacitors to deliver a therapeutic shock through the first defibrillator electrode pad and the second defibrillator electrode pad to the patient while the first and second patient engagement substrates are engaged with the patient, wherein the energy source, one or more capacitors, and controller are enclosed within one or more housings.

This and other embodiments can include one or more of the following features. The first patient engagement substrate can include the one or more sensing electrodes. The first patent engagement substrate can include two or more sensing electrodes. The second patient engagement substrate can include a sensing electrode. The first defibrillator electrode pad and second defibrillator electrode pad can be adapted to detect the cardiac signal. The one or more housings can include a first controller housing, the controller can be included in the first controller housing. The one or more housings can include a first energy source housing, the energy source can be included in the first energy source housing. The one or more housings can include a first capacitor housing and a second capacitor housing, the capacitors can be included in the first capacitor housing and the second capacitor housing. The first controller housing can include a first controller housing electrical connection, the first energy source housing can include a first energy source housing electrical connection, the first capacitor housing can include a first capacitor electrical connection, and the second capacitor housing can include a second electrical connection. The wearable defibrillator can further include a mechanical connection between each of the first controller housing, first energy source housing, first capacitor housing, and second capacitor housing. The wearable defibrillator can further include a flexible circuitry and one or more rigid printed circuit boards (PCBs). The flexible circuitry can be adapted to receive the first controller housing electrical connection, the first energy source housing electrical connection, the first capacitor electrical connection, and the second electrical connection. The flexible circuitry can be in electrical communication with the first controller housing, first energy source housing, first capacitor housing, and second capacitor housing.

The flexible circuitry can provide electrical communication between the first controller housing and the first energy source housing, first capacitor housing, and second capacitor housing. The flexible circuitry can be supported by the first patient engagement substrate between the first vapor permeable layer and the first defibrillator electrode pad. The first patient engagement substrate can be adapted to support the one or more housings. The second patient engagement substrate can be adapted to support the one or more housings. The first patient engagement substrate and second patient engagement substrate can be configured to be worn during showering activities. The first patient engagement substrate can include an exterior surface and the second patient engagement substrate can include an exterior surface. A portion of the first vapor permeable layer can represent an exterior surface of the first patient engagement surface. A portion of the second vapor permeable layer can represent an exterior surface of the second patient engagement surface. The exterior surfaces of the first patient engagement substrate and the second patient engagement substrate can be moisture vapor permeable. The exterior surfaces of the first patient engagement substrate and the second patient engagement substrate can have a moisture vapor transport above about 1000 $g/m^2$ per day based on a surface area of the patient engagement substrate. The exterior surfaces of the first patient engagement substrate and the second patient engagement substrate can have a moisture vapor transport above about 2000 $g/m^2$ per day based on a surface area of the patient engagement substrate. The exterior surfaces of the first patient engagement substrate and the second patient engagement substrate can have a moisture vapor transport above about 5000 $g/m^2$ per day based on a surface area of the patient engagement substrate. The exterior surfaces of the first patient engagement substrate and the second patient engagement substrate can have a moisture vapor transport above about 8000 $g/m^2$ per day based on a surface area of the patient engagement substrate. The exterior surfaces of the first patient engagement substrate and the second patient engagement substrate can be air permeable. The exterior surfaces of the first patient engagement substrate and the second patient engagement substrate can be waterproof. The exterior surfaces of the first and second patient engagement substrates can be hydrophobic. The first fluid transport element and second fluid transport element can be configured to transport fluid away from the skin. The wearable defibrillator can further include a support chassis disposed between the one or more housings and the first defibrillator electrode pad. The support chassis can be adapted to spread a shear load of the one or more housings across a dominant surface of the support chassis. The wearable defibrillator can further include a pulse oximeter configured to measure an oxygen content of a blood of the patient at a point on a chest of the patient. The wearable defibrillator can further include an ultrasound transceiver or transducer configured to transmit and/or receive ultrasonic signals. The wearable defibrillator can further include a Doppler radar configured to transmit a microwave signal and receive a returned microwave signal. The first defibrillator electrode pad can include a first pair of electrodes. The controller can be configured to measure a first impedance between the first pair of electrodes. The controller can be configured to analyze the first impedance to determine whether the first pair of electrodes are in proper contact with the patient's skin. The second defibrillator electrode pad can include a second pair of electrodes. The controller can be configured to measure a second impedance between the second pair of electrodes. The controller can be configured to analyze the second impedance to determine whether the second pair of electrodes are in proper contact with the patient's skin. The controller can be configured to measure a transthoracic impedance between the first pair of electrodes and the second pair of electrodes. The wearable defibrillator can further include a slip layer disposed between the housing and adhesive configured to allow relative movement between the housing and the adhesive. The wearable defibrillator can further include a first sealing layer enclosing the energy source, one or more capacitors, and controller. The first sealing layer can be within the housing. The first sealing layer can contact the housing. The wearable defibrillator can further include a second sealing layer containing the housing. The wearable defibrillator can further include a connector plug on the housing with a plurality of electrical connections. The plurality of electrical connections can include a first defibrillator electrode pad connection and a second defibrillator electrode pad connection. The first defibrillator electrode pad connection and the second defibrillator electrode pad connection can be configured to be in electrical communication with the one or more capacitors and the first and second defibrillator electrode pads. The plurality of electrical connections can include a plurality of sensing electrode connections. The plurality of sensing electrode connections can be each configured to be in electrical communication with the controller and one of the one or more sensing electrodes. The wearable defibrillator can further include an enclosure configured to surround the housing, the enclosure can include an enclosure connection and can have a first side with a complementary structure configured to engage with the connector plug on the housing. The wearable defibrillator can further include a second side of the enclosure connection configured to engage with a patient engagement substrate connector on the first patient engagement substrate, the patient engagement substrate connector in electrical communication with the one or more capacitors and the first and second defibrillator electrode pads. The adhesive can include a plurality of pores configured to allow the transport of moisture vapor. The one or more sensing electrodes and defibrillator electrode pads can include a plurality of pores configured to allow the transport of moisture vapor. The first defibrillator electrode pad the second defibrillator electrode pad can include a polyethylene terephthalate (PET) substrate with a conductive ink coating. The first defibrillator electrode pad can include a first conductive adhesive and a first conductive electrode. The second defibrillator electrode pad can include a second conductive adhesive and a second conductive electrode. The first and second conductive electrodes can have a solid construction. The first and second conductive electrodes can be made from a flexible sheet having a plurality of perforations. The first and second conductive electrodes can include a carbon vinyl film, Ag/AgCl coated carbon vinyl film, or Ag coated carbon vinyl film. The first and second conductive electrodes of the first and second defibrillator electrode pads can have a woven structure. The first and second conductive electrodes of the first and second defibrillator electrode pads can include carbon fiber. The first conductive adhesive and the second conductive adhesive can include a conductive hydrogel. The conductive hydrogel can include a salt. The first conductive adhesive and the second conductive adhesive can include an adhesive with a conductive filler. The conductive filler can include one or more of: carbon nanotubes, graphene, carbon black, silver particles, metal particles, and silver nanowires. The first patient engagement substrate can be configured to insulate between the one or more sensing electrodes and the first defibrillator electrode pad. The second patient engagement substrate can be configured to insulate between the sensing electrode and the second defibrillator electrode pad. The adhesive on the first and second patient engagement substrates can be non-conductive. The wearable defibrillator can further include an inclinometer configured to determine the position and orientation of the wearable defibrillator. The wearable defibrillator can further include a radio beacon configured to transmit the location of the wearable defibrillator. The wearable defibrillator can further include a GPS sensor. The wearable defibrillator can further include a wireless radio configured to wirelessly transmit data from the wearable defibrillator. The wireless radio can be configured to transmit data over a cellular network. The wearable defibrillator can further include a sensor configured to measure a mechanical stretch of a portion of the wearable defibrillator. The one or more capacitors can be configured to be reversibly and removably engaged with the wearable defibrillator. The energy source can be configured to be reversibly and removably engaged with the wearable defibrillator. The controller can be configured to be reversibly and removably engaged with the wearable defibrillator. The wearable defibrillator can further include a first adhesive release liner configured to cover the adhesive on the first patient engagement substrate. The wearable defibrillator can further include a second adhesive release liner configured to cover the adhesive on the second patient engagement substrate. The housing can be configured to receive a plurality of energy sources. The energy source can include a first modular battery and a second modular battery, the first and second modular batteries can be configured to be removably received within the housing. The wearable defibrillator can further include an external pacing module configured to provide a pacing signal to the patient, the external pacing module can be supported by the first or second patient engagement substrate. The wearable defibrillator can further include a skin contact module configured to sense removal of the first and/or second patient engagement substrate from the patient's skin. The skin contact module can be configured to generate an alarm and/or notification to a healthcare provider upon sensing removal of the first and/or second patient engagement substrate from the patient's skin. The wearable defibrillator can further include a cantilever coupled to the housing and the first patient engagement substrate. The housing can include a plurality of compartments containing the energy source, one or more capacitors, and controller. The wearable defibrillator can further include a flexible circuitry and one or more rigid printed circuit boards (PCBs) within the housing. The plurality of compartments can be in fluid communication within the housing. The plurality of compartments may not be in fluid communication with the other of the plurality of compartments. The plurality of compartments can be separate and configured to reversibly engage with the other of the plurality of compartments. The plurality of compartments can be connected with a plurality of waterproof connector segments. The housing can be configured to allow relative movement between the plurality of compartments of the housing. The relative movement can include flexing with a plane of the first patient engagement substrate. The housing can include an outer clam shell and a base. The outer clam shell can be ultrasonically welded to the base. The outer clam shell can be attached to the base with an adhesive. The outer clam shell can be attached to the base through chemical bonding. The one or more sensing electrodes of the first patient engagement substrate and the sensing electrode of the second patient engagement substrate and the first and second defibrillator electrode pads can be configured to sense impedance changes along a plurality of vectors of the patient, the controller can be configured to analyze the impedance changes along the plurality of vectors of the patient to measure a cardiac health of the patient. The first patient engagement substrates can include a patient engagement portion including the one or more sensing electrodes, the adhesive, and first defibrillator electrode pad. The first patient engagement substrate can include a moisture vapor transport above about 100 $g/m^2$ per day based on a surface area of the patient engagement portion through the patient engagement portion and the first vapor permeable layer. The first patient engagement substrate can include a moisture vapor transport above about 500 $g/m^2$ per day based on a surface area of the patient engagement portion through the patient engagement portion and the first vapor permeable layer. The first patient engagement substrate can include a moisture vapor transport above about 1000 $g/m^2$ per day based on a surface area of the patient engagement portion through the patient engagement portion and the first vapor permeable layer. The first patient engagement substrate can include a moisture vapor transport above about 1500 $g/m^2$ per day based on a surface area of the patient engagement portion through the patient engagement portion and the first vapor permeable layer. The second patient engagement substrate can include a second patient engagement portion including the sensing electrode, the second adhesive, and second defibrillator electrode pad. The first patient engagement substrate can include a moisture vapor transport above about 100 g/m² per day based on a surface area of the patient engagement portion through the second patient engagement portion and the second vapor permeable layer. The first patient engagement substrate can include a moisture vapor transport above about 500 g/m² per day based on a surface area of the patient engagement portion through the second patient engagement portion and the second vapor permeable layer. The first patient engagement substrate can include a moisture vapor transport above about 1000 g/m² per day based on a surface area of the patient engagement portion through the second patient engagement portion and the second vapor permeable layer. The first patient engagement substrate can include a moisture vapor transport above about 1500 g/m² per day based on a surface area of the patient engagement portion through the second patient engagement portion and the second vapor permeable layer. The first patient engagement substrate can have a preformed curvature. The preformed curvature can correspond to a shape of a human torso. The second patient engagement substrate can have a preformed curvature. The preformed curvature can correspond to a shape of a human chest. The wearable defibrillator can further include a cable forming an electrical communication between the first patient engagement substrate and the second patient engagement substrate. The cable can form the electrical communication between the sensing electrode of the second patient engagement substrate and the controller. The cable can form the electrical communication between the second defibrillator electrode pad and the one or more capacitors. The wearable defibrillator can further include a display indicator. The display indicator can be part of the first patient engagement substrate or second patient engagement substrate. The display indicator can be part of the one or more housings. The display indicator can be part of a cable between the first patient engagement substrate or second patient engagement substrate. The display indicator can be a light emitting diode (LED). The wearable defibrillator can further include a tactile feedback module. The tactile feedback module can be part of the first patient engagement substrate or second patient engagement substrate. The tactile feedback module can be part of the one or more housings. The tactile feedback module can be a vibration motor. The wearable defibrillator can further include one or more buttons on the one or more housings. The wearable defibrillator can further include a first connection between the housing and the first patient engagement substrate and a second flexible connection between the housing and the first patient engagement substrate, the first connection can be on a first end of the first patient engagement substrate and the second flexible connection can be on a second end of the first patient engagement substrate that opposes the first end of the first patient engagement substrate. The second flexible connection can allow for relative movement between the second end of the first patient engagement substrate and the housing. The wearable defibrillator can further include a first sensing electrode release liner configured to cover the one or more sensing electrodes on the first patient engagement substrate and a first defibrillator electrode pad release liner configured to cover the first defibrillator electrode pad. The wearable defibrillator can further include a second sensing electrode release liner configured to cover the one or more sensing electrodes on the second patient engagement substrate and a second defibrillator electrode pad release liner configured to cover the second defibrillator electrode pad. The housing can be supported by two or more patient engagement substrates. The wearable defibrillator can further include an electroactive polymer. The electroactive polymer can be configured to detect a change in a morphology of the first patient engagement substrate and/or second patient engagement substrate. The electroactive polymer can be configured to vibrate. The electroactive polymer can be configured to deform to change the morphology of the first and/or second patient engagement substrate. The wearable defibrillator can further include a flexible connection between the housing and the first patient engagement substrate configured to support the weight of the housing and components within the housing. The flexible connection can allow for relative movement between the housing and the first patient engagement substrate. The flexible connection can further include one or more electrical connections between the housing and the first patient engagement substrate. The flexible connection can include a removable and reversible connection. The one or more housings each can have a clam shell configuration sealed with an adhesive. The one or more housings each can have a clam shell configuration sealed with ultrasonic welding. The one or more housings each can have a clam shell configuration sealed through chemical bonding. The controller can be configured to analyze an impedance between one or more of: the one or more sensing electrodes, the first defibrillator electrode pad, the second defibrillator electrode pad, and the sensing electrode. The controller can further be configured to measure the impedance using two or more discrete frequencies. The two or more discrete frequencies can include a high frequency measurement and a low frequency measurement. The controller can further be configured to analyze the high frequency measurement and low frequency measurement to determine a power of the therapeutic shock for the patient based on the impedance. The wearable defibrillator can further include a temperature sensor.

In general, in one embodiment, a method of monitoring and defibrillating a patient's heart, including adhering to a first skin surface portion of the patient a first patient engagement substrate including a first plurality of sensing electrodes and a first defibrillator electrode pad, the first defibrillator electrode pad in electrical communication with an electrical energy source sufficient to provide a defibrillating shock, the first patient engagement substrate part of a wearable defibrillator including a fluid transport element configured to transport fluid away from the first skin surface portion of the patient to allow the wearable external defibrillator to be worn continuously; adhering to a second skin surface portion of the patient a second patient engagement substrate including a sensing electrode and a second defibrillator electrode pad, the second defibrillator electrode pad in electrical communication with the electrical energy source sufficient to provide the defibrillating shock, the second patient engagement substrate part of the wearable defibrillator, the wearable defibrillator including one or more sensors adapted to detect one or more of the pulse, oxygen content of the blood, impedance, galvanic skin impedance, temperature, breathing rate, heart sounds, and heart rate of the patient; measuring patient data corresponding to a cardiac signal or other characteristic of the patient with the first plurality of sensing electrodes, the sensing electrode of the second patient engagement substrate, and/or the sensors of the wearable defibrillator; and analyzing the patient data to determine if the patient has an arrhythmia.

This and other embodiments can include one or more of the following features. The method can further include upon detection of an arrhythmia detecting one or more of the pulse, oxygen content of the blood, impedance, galvanic skin impedance, temperature, breathing rate, heart sounds, and heart rate of the patient using one or more sensors on the wearable defibrillator; and analyzing the detected one or more of the pulse, oxygen content of the blood, breathing rate, heart sounds, and heart rate of the patient to confirm the presence or absence of the arrhythmia. The method can further include sensing impedance changes along a plurality of vectors of the patient with the one or more sensing electrodes of the first patient engagement substrate and the sensing electrode of the second patient engagement substrate and the first and second defibrillator electrode pads. The method can further include comparing the impedance changes to a patient baseline and/or a database to measure a cardiac health of the patient. The method can further include measuring electrical data corresponding to a cardiac signal of the patient with the first plurality of sensing electrodes and the sensing electrode of the second patient engagement substrate. The method can further include detecting one or more of the breathing rate, heart sounds, and heart rate of the patient with a microphone on the wearable defibrillator. The method can further include recording patient movement with an accelerometer integrated with the wearable defibrillator upon detection of an arrhythmia; and analyzing the recorded patient movement to confirm the presence or absence of the arrhythmia. The method can further include detecting the oxygen content of the blood with a pulse oximeter on the wearable defibrillator. Detecting the oxygen content of the blood with a pulse oximeter on the wearable defibrillator can include measuring the oxygen content of the blood of the patient at a point on a chest of the patient. The method can further include measuring a transthoracic impedance between the first defibrillator electrode pad and the second defibrillator electrode pad. The first defibrillator electrode pad can include two separate electrodes, can further include measuring an impedance between the two separate electrodes of the first defibrillator electrode pad. The method can further include analyzing the impedance between the two separate electrodes of the first defibrillator electrode pad to determine whether the two separate electrodes of the first defibrillator electrode pad are in sufficient electrical contact with the skin to deliver an electrical shock. The second defibrillator electrode pad can include two separate electrodes, can further include measuring an impedance between the two separate electrodes of the second defibrillator electrode pad. The method can further include analyzing the impedance between the two separate electrodes of the second defibrillator electrode pad to determine whether the two separate electrodes of the second defibrillator electrode pad are in sufficient electrical contact with the skin to deliver an electrical shock. The method can further include delivering an electrical shock after determining that the patient has an arrhythmia. The method can further include analyzing the measured electrical data corresponding to the cardiac signal of the patient for bradycardia, atrial fibrillation, asystole, heart blocks, pauses, ventricular tachycardia, ventricular fibrillation, tachycardia with aberrancy, or a supraventricular tachycardia (SVT). The method can further include continuously wearing the wearable defibrillator for greater than about 24 hours. The method can further include continuously wearing the wearable defibrillator for greater than about 5 days. The method can further include continuously wearing the wearable defibrillator for greater than about 7 days. The method can further include continuously wearing the wearable defibrillator for greater than about 10 days. The method can further include continuously wearing the wearable defibrillator for greater than about 14 days.

In general, in one embodiment, a method for refurbishing a wearable defibrillator including receiving a wearable defibrillator including an energy source, a controller, and a memory containing a patient data set collected while the wearable defibrillator was worn by a patient; copying the patient data set from the memory to a computer network or system external to the wearable defibrillator; erasing the patient data set from the memory of the wearable defibrillator; recharging or replacing the energy source of the wearable defibrillator; and running a diagnostic test on the wearable defibrillator after erasing the patient data set and recharging or replacing the energy source.

This and other embodiments can include one or more of the following features. The wearable defibrillator can be any of the wearable defibrillators described herein. The wearable defibrillator can further include one or more sensing electrodes configured to engage with a patient's skin to detect a cardiac signal; a defibrillator electrode pad configured to engage with the patient's skin and to deliver an electrical therapy to the patient; a patient engagement substrate including an adhesive, the one or more sensing electrodes, and the defibrillator electrode pad; and one or more capacitors in electrical communication with the energy source and the defibrillator electrode pad, wherein the controller is configured to detect the cardiac signal with the sensing electrodes and to charge the one or more capacitors with the energy source followed by discharging the one or more capacitors to deliver a therapeutic shock through the defibrillator electrode pad to the patient while the patient engagement substrate is engaged with the patient. The wearable defibrillator can include one or more modules containing the one or more capacitors, energy source, and controller. The wearable defibrillator can include a module containing the energy source, and replacing the energy source includes replacing the module containing the energy source. The diagnostic test can include testing the one or more capacitors, memory, energy source, and controller. The wearable defibrillator can further include one or more housings containing one or more of the controller, memory, capacitors, and energy source. The controller and memory can be included in a first controller housing, the energy source can be included in a first energy source housing, and the capacitors can be included in a first capacitor housing and a second capacitor housing. The method can further include removing the controller and memory from the first controller housing. The method can further include removing the energy source from the first energy source housing. The method can further include removing the one or more capacitors from the first capacitor housing and the second capacitor housing. The diagnostic test can include testing the one or more capacitors, memory, energy source, and controller after removal from the one or more housings. The method can further include engaging a data transfer cable with a connector in electrical communication with the memory. The method can further include after running the diagnostic test, placing the controller and memory in a second controller housing. The method can further include after running the diagnostic test, placing the one or more capacitors in a new first capacitor housing and a new second capacitor housing. The method can further include after running the diagnostic test, placing the energy source in a second energy source housing. The method can further include engaging the second controller housing, new first capacitor housing, new second capacitor housing, and second energy source housing with a patient engagement substrate to form a refurbished wearable defibrillator. The method can further include sealing the one or more housings to prevent water ingress. The wearable defibrillator can be configured to support the one or more housings within a waterproof enclosure. The method can further include removing the housing from the waterproof enclosure after receiving the wearable defibrillator. The method can further include engaging a data transfer cable with an exterior connection of the one or more housings. Copying can include a wireless data transfer between the memory and the computer network or system. Copying can include a wired data connection to transfer the patient data set between the memory and the computer network or system. The method can further include after running the diagnostic test, placing the housing within a second waterproof enclosure. The method can further include engaging the housing with the second waterproof enclosure with a patient engagement substrate to form a refurbished wearable defibrillator. The refurbished wearable defibrillator can include one or more sensing electrodes configured to engage with a patient's skin to detect a cardiac signal; a defibrillator electrode pad configured to engage with the patient's skin and to deliver an electrical therapy to the patient; the patient engagement substrate including an adhesive, the one or more sensing electrodes, and the defibrillator electrode pad; and one or more capacitors in electrical communication with the energy source and the defibrillator electrode pad, wherein the controller is configured to detect the cardiac signal with the sensing electrodes and to charge the one or more capacitors with the energy source followed by discharging the one or more capacitors to deliver a therapeutic shock through the defibrillator electrode pad to the patient while the patient engagement substrate is engaged with the patient, wherein the one or more capacitors, energy source, and controller are enclosed within one or more housings. The method can further include forming one or more electrical connections between the one or more housings and the one or more sensing electrodes and defibrillator electrode pads of the refurbished wearable defibrillator. The method can further include packaging the refurbished wearable defibrillator. The method can further include sending the refurbished wearable defibrillator to a second patient. The method can further include receiving the refurbished wearable defibrillator containing a second patient data set collected while the refurbished wearable defibrillator was worn by the second patient. The method can further include copying the second patient data sent from the memory to a computer network or system external to the refurbished wearable defibrillator; and erasing the patient data set from the memory of the refurbished wearable defibrillator. The method can further include replacing or refurbishing the one or more housings in the refurbished wearable defibrillator. The method can further include replacing or refurbishing the one or more housings and reusing the one or more capacitors five or more times. The method can further include replacing or refurbishing the one or more housings and reusing the one or more capacitors ten or more times. The method can further include replacing or refurbishing the one or more housings and reusing the one or more capacitors fifteen or more times. The method can further include replacing or refurbishing the one or more housings and reusing the one or more capacitors twenty or more times. The energy source can include a rechargeable battery. The method can further include recharging the rechargeable battery. The energy source can include a battery. The method can further include replacing the battery. The patient data set can include data from the patient continuously wearing the wearable defibrillator for greater than about 24 hours. The patient data set can include data from the patient continuously wearing the wearable defibrillator for greater than about 5 days. The patient data set can include data from the patient continuously wearing the wearable defibrillator for greater than about 7 days. The patient data set can include data from the patient continuously wearing the wearable defibrillator for greater than about 10 days. The patient data set can include data from the patient continuously wearing the wearable defibrillator for greater than about 14 days.

In general, in one embodiment, a method for providing instructions for placing a wearable defibrillator on a patient, the method including providing instructions on where to put a first patient engagement substrate of the wearable defibrillator on a torso of the patient, the first patient engagement substrate including one or more sensing electrodes, adhesive, and a first defibrillator electrode pad, the instructions including where to put the one or more sensing electrodes and first defibrillator electrode pad on the chest of the patient; providing instructions on where to put a second patient engagement substrate of the wearable defibrillator, the second patient engagement substrate including a sensing electrode, adhesive, and a second defibrillator electrode pad, the instructions including where to put the one or more sensing electrodes and second defibrillator electrode pad; verifying a first patient engagement substrate placement on the torso of the patient including the placement of the one or more sensing electrodes and first defibrillator electrode pad; and verifying a second patient engagement substrate placement on the chest of the patient including the sensing electrode and second defibrillator electrode pad.

This and other embodiments can include one or more of the following features. The instructions can be provided to the patient. The person applying the wearable defibrillator can be the patient. The instructions can be provided to a person applying the wearable defibrillator to the patient. The person applying the wearable defibrillator can be a health care provider. The wearable defibrillator can further include a first sensing electrode release liner configured to cover the one or more sensing electrodes on the patient engagement substrate, a first defibrillator electrode pad release liner configured to cover the first defibrillator electrode pad, and a first adhesive release liner configured to cover the adhesive on the first patient engagement substrate; and a second sensing electrode release liner configured to cover the one or more sensing electrodes on the second patient engagement substrate and a second defibrillator electrode pad release liner configured to cover the second defibrillator electrode pad, and a second adhesive release liner configured to cover the adhesive on the second patient engagement substrate. The method can further include providing instructions to sequentially remove the first sensing electrode release liner, the first defibrillator electrode pad release liner, and the first adhesive release liner. The method can further include providing instructions to sequentially remove the second sensing electrode release liner, the second defibrillator electrode pad release liner, and the second adhesive release liner. The wearable defibrillator can further include a primary patient engagement substrate release liner configured to cover a first portion of the patient engagement substrate; a secondary patient engagement substrate release liner configured to cover a second portion of the patient engagement substrate; a primary second patient engagement substrate release liner configured to cover a first portion of the second patient engagement substrate; and a secondary second patient engagement substrate release liner configured to cover a second portion of the second patient engagement substrate. The method can further include providing instructions to sequentially remove the primary patient engagement substrate release liner, secondary patient engagement substrate release liner, primary second patient engagement substrate release liner, and secondary second patient engagement substrate release liner. The method can further include providing instructions to shave, clip, trim, chemically remove, or otherwise depilate, and clean the skin of the patient. The method can further include measuring an impedance between the first and second defibrillator electrode pad. The method can further include measuring an impedance between a plurality of the one or more sensing electrodes. The method can further include analyzing the impedance between the first and second defibrillator electrode pad and the impedance between a plurality of the one or more sensing electrodes to verifying the correct placement of the first patient engagement substrate and the second patient engagement substrate. Verifying placement can include determining a location of a plurality of low power radios integrated with the wearable defibrillator.

In general, in one embodiment, a wearable device including one or more sensing electrodes configured to engage with a patient's skin to detect a signal, the one or more sensing electrodes configured to be in continuous electrical communication with the patient's skin; a patient engagement substrate including an adhesive, one or more sensing electrodes, and a fluid transport element configured to transport fluid away from the skin to allow the wearable device to be worn continuously; one or more compartments supported by the patient engagement substrate, the one or more compartments configured to reversibly receive and support one or more of: an energy source, one or more capacitors, and a controller; and an electrical connector configured to removably and reversibly engage with one or more of: the energy source, one or more capacitors, and the controller, the electrical connector supported by the patient engagement substrate and/or the one or more compartments.

This and other embodiments can include one or more of the following features. The wearable device can further include a second patient engagement substrate including an adhesive, one or more sensing electrodes, and a fluid transport element. The adhesive can include a plurality of pores configured to allow the transport of vapor. The patient engagement substrate can be configured to be worn continuously during movement and showering activities for greater than about 24 hours. The patient engagement substrate can be configured to be worn continuously during movement and showering activities for greater than about 5 days. The patient engagement substrate can be configured to be worn continuously during movement and showering activities for greater than about 10 days.

In general, in one embodiment, a method for detecting symptoms associated with sleep apnea including measuring one or more of a heart rate, a breathing rate, and a breathing pattern of the patient with a wearable device including one or more sensing electrodes and a sensor configured to measure the breathing rate and pattern of the patient, the wearable device adhesively attached to a portion of the skin of the patient; and analyzing the one or more of the measured heart rate, oxygen saturation, ECG rhythm, ECG morphology, ECG amplitude, chest movement, breathing rate, and breathing pattern to detect a symptom or indication of sleep apnea in the patient.

This and other embodiments can include one or more of the following features. The method can further include upon detection of the symptom or indication of sleep apnea in the patient, generating and providing a stimulus to the patient. Providing a stimulus can include a vibration, an electrical shock, a visual alert, or auditory alarm.

In general, in one embodiment, a method of detecting symptoms associated with a cardiac health of a patient including measuring one or more of a heart rate, a breathing rate, a breathing pattern of the patient, an impedance across and through a chest and thoracic cavity of the patient, and a size of blood vessels within a body of the patient like an inferior vena cava, blood pressure waveform, lung sounds, patient posture and activity, and pulse oxygenation with a wearable device including one or more sensing electrodes and one or more sensors configured to measure the heart rate, breathing rate and pattern of the patient, the trans-thoracic impedance of the patient, and the size of the blood vessels in the body, blood pressure, wherein the wearable device is adhesively attached to a portion of the skin of the patient; and analyzing the one or more of the measured heart rate, oxygen saturation, ECG rhythm, ECG morphology, ECG amplitude, chest movement, breathing rate, breathing pattern, trans-thoracic impedance, blood pressure and blood pressure waveform in different body postures, and size of the blood vessels in the body to detect a symptom or indication of cardiac disease in the patient.

This and other embodiments can include one or more of the following features. The method can further include upon detection of the symptom or indication of heart failure in the patient, generating and providing a stimulus to the patient. The stimulus can be one or more of: an electrical shock, a vibration, a visual alert, or an auditory alert to the patient or physician. The method can further include upon detection of the symptom or indication of heart failure in the patient, saving a patient data to memory for later analysis or wirelessly transmitting the patient data to a computer for analysis. The method can further include analyzing the one or more of the measured parameters to determine a derived parameter for the patient for one or more of: ejection fraction, cyanosis, pulse quality, dyspnea, orthopnea, peripheral or pulmonary edema, right heart failure, left heart failure, nocturia, and cardiac arrhythmias, pulsus alternans, S3 cardiac sound, S4 cardiac sound, and splitting in S1 and S2 heart sounds. The derived parameters can include pulmonary edema, ejection fraction, cyanosis, pulse quality, dyspnea, orthopnea, or nocturia. The measurements being used to detect the symptom or indication of cardiac disease can include cardiac arrest and myocardial infarction. The measurements being used to detect the symptom or indication of cardiac disease can include heart failure, cardiomyopathies, heart blocks, atrial and ventricular arrhythmias. Pulmonary edema can be determined using chest impedance by measuring multiple vectors across the chest from various leads which allows assessment of fluid status in multiple different segments of the thoracic cavity. The method can further include analyzing the heart sounds measured by a microphone to determine the presence or absence of one or more of: rales or rhonchi, the presence of S3 and S4 heart sounds, and pathologies such as splitting in the S1 and S2 heart sounds. Ejection fraction can be determined using ultrasound and localized impedance changes to determine trending information of blood flow over time as a proxy for ejection fraction. Cyanosis can be determined using pulse oxygenation and impedance status to determine changes in blood oxygenation. Pulse quality can be determined using Doppler ultrasound delivered and can be measured by the wearable device together with closely spaced impedance sensors to determine changes in the shape of the pulse wave to indicate changes in cardiac function, including pulsus alternans. Dyspnea can be determined using a combination of accelerometer to determine patient posture and pulse oxygenation with impedance to determine the breathing pattern including accounting for recent activity of the patient to determine whether dyspnea is at rest. Dyspnea can be determined using a combination of accelerometer to determine patient posture and pulse oxygenation with impedance to determine the breathing pattern including accounting for recent activity of the patient to determine whether dyspnea is at rest. Orthopnea can be determined using ultrasound to determine blood pressure together with accelerometer to determine patient posture can give an estimate of orthostasis. Nocturia can be determined using number of times the patient gets up during sleep as a proxy for nocturia.

In general, in one embodiment, a wearable device including a patient engagement substrate including an adhesive, one or more sensors, a first fluid transport element configured to transport fluid away from the skin to allow the wearable device to be worn continuously, and a first vapor permeable layer, the one or more sensors adapted to detect one or more of a pulse, a cardiac signal, oxygen content of the blood, impedance, galvanic skin impedance, temperature, breathing rate, heart sounds, and heart rate of a patient; and a controller configured to receive data collected by the one or more sensors and analyze the data to determine if the patient exhibits a symptom associated with sleep apnea.

This and other embodiments can include one or more of the following features. The wearable device can further be configured to provide a stimulus to the patient upon detection of a symptom associated with sleep apnea. The stimulus can include a vibration, an electrical shock, a visual alert, electronic notification, or auditory alarm. The controller can be configured to apply an algorithm to the data collected by the one or more sensors. The algorithm can adapt to the specific patient wearing the device.

In general, in one embodiment, a wearable device including a patient engagement substrate including an adhesive, one or more sensors, a first fluid transport element configured to transport fluid away from the skin to allow the wearable device to be worn continuously, and a first vapor permeable layer, the one or more sensors adapted to detect one or more of a pulse, a cardiac signal, oxygen content of the blood, impedance, galvanic skin impedance, temperature, breathing rate, heart sounds, and heart rate of a patient; and a controller configured to receive data collected by the one or more sensors and analyze the data to determine if the patient exhibits a symptom associated with heart failure. The wearable device can further be configured to provide a stimulus to the patient upon detection of a symptom associated with heart failure. The stimulus can include a vibration, an electrical shock, a visual alert, electronic notification, or auditory alarm. The controller can be configured to apply an algorithm to the data collected by the one or more sensors. The algorithm can adapt to the specific patient wearing the device. The one or more sensors can include one or more of: accelerometer, ECG sensing electrodes, pulse oximeter, microphone, magnetometer, impedance sensors, and galvanic skin impedance sensor. The controller can further be configured to perform any of the previously described methods.

In general, in one embodiment, a system including any of the previously mentioned wearable defibrillators; and a fitting tool including a first complementary surface and a second complementary surface, the first complementary surface adapted to engage with a complementary surface of the one or more housings of the first patient engagement substrate and the second complementary surface adapted to engage with a complementary surface of the second patient engagement substrate.

This and other embodiments can include one or more of the following features. The fitting tool can further include a plurality of straps configured to secure the first patient engagement substrate and the second patient engagement substrate against a skin of the patient. The methods can further include providing a fitting tool including a first complementary surface and a second complementary surface, the first complementary surface adapted to engage with a complementary surface of the one or more housings of the first patient engagement substrate and the second complementary surface adapted to engage with a complementary surface of the second patient engagement substrate. The method can further include providing instructions for wearing the fitting tool. The method can further include providing instructions for engaging the first complementary surface with the complementary surface of the one or more housings of the first patient engagement substrate to position the first patient engagement substrate on the torso of the patient. The method can further include providing instructions for engaging the second complementary surface with the complementary surface of the second patient engagement substrate to position the second patient engagement substrate on the chest of the patient. The method can further include applying an algorithm to analyze the one or more of the measured heart rate, oxygen saturation, ECG rhythm, ECG morphology, ECG amplitude, chest movement, breathing rate, and breathing pattern to detect the symptom or indication of sleep apnea in the patient. The algorithm can be a fixed algorithm. The algorithm can be an adaptive algorithm that adapts to the patient. The method can further include changing a sampling frequency of any of the one or more sensing electrodes and the sensor of the wearable device based on the algorithm. Changing the sampling frequency can be triggered by a predetermined characteristic collected by the one or more sensing electrodes and the sensor. The method can further include applying an algorithm to analyze the one or more of the measured heart rate, oxygen saturation, ECG rhythm, ECG morphology, ECG amplitude, chest movement, breathing rate, breathing pattern, trans-thoracic impedance, blood pressure and blood pressure waveform in different body postures, and size of the blood vessels in the body to detect the symptom or indication of cardiac disease in the patient. The algorithm can be a fixed algorithm. The algorithm can be an adaptive algorithm that adapts to the patient. The method can further include changing a sampling frequency of any of the one or more sensing electrodes and the sensor of the wearable device based on the algorithm. Changing the sampling frequency can be triggered by a predetermined characteristic collected by the one or more sensing electrodes and the sensor.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 7A-7B illustrate an exterior view and exploded view, respectively, of a patient engagement substrate that is part of a wearable defibrillator in accordance with some embodiments.

FIG. 14 is a flow chart of a method of monitoring and defibrillating a patient's heart in accordance with some embodiments.

FIG. 36 illustrates an electrode configuration with microneedles in accordance with some embodiments.

FIG. 42 is a flow chart illustrating a method of providing instructions for placing the wearable defibrillators described herein.

DETAILED DESCRIPTION

Figure 1:
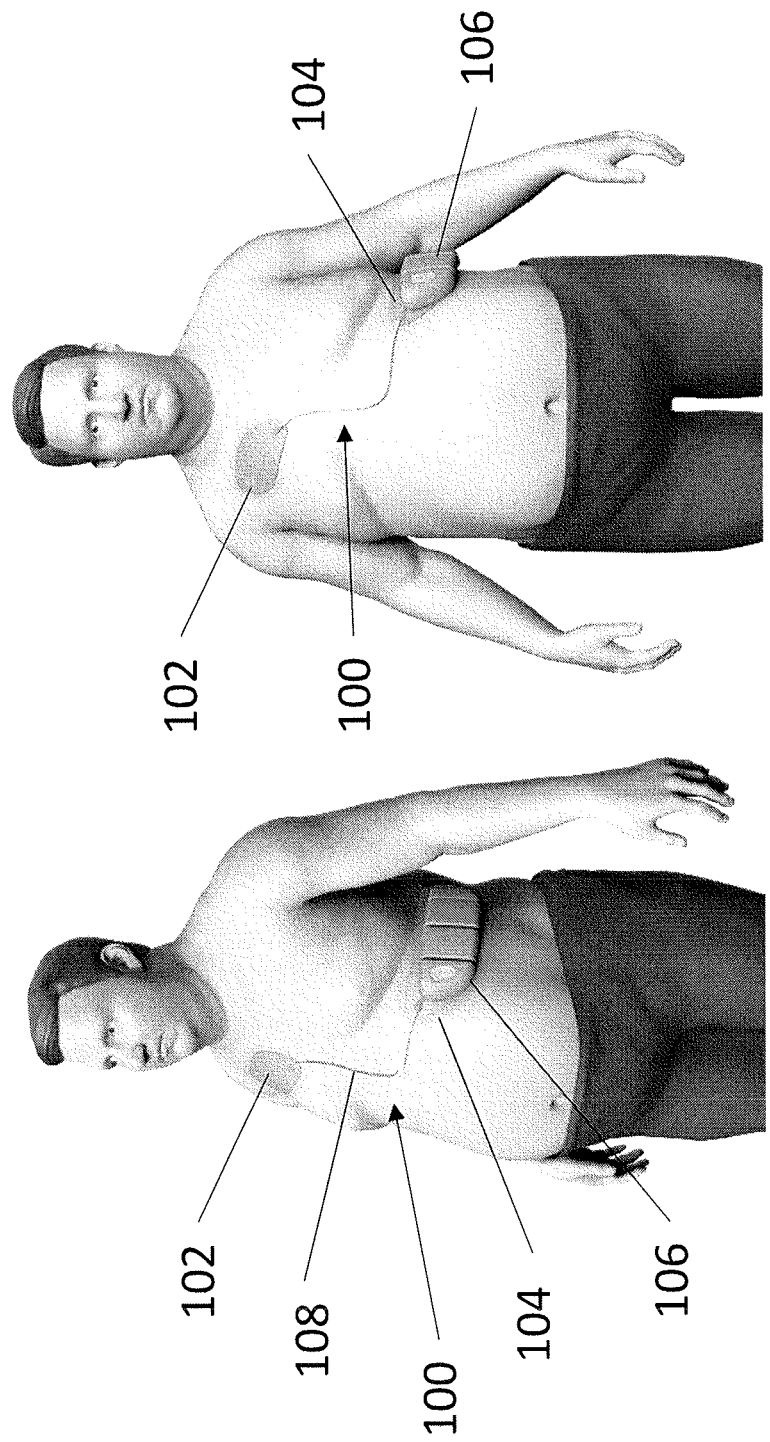
FIG. 1 illustrates an embodiment of a wearable defibrillator on a patient in accordance with some embodiments.

Wearable defibrillators are disclosed herein that are configured for long term wear. The wearable defibrillators can include a plurality of different sensors and electrodes to measure and analyze the condition of the wearer of the defibrillator and to deliver a therapeutic electrical shock or other stimulus to the wearer. Methods for using the wearable defibrillators and methods for processing the wearable defibrillators are also disclosed herein.

Wearable external defibrillators are provided herein. The wearable defibrillators can include one or more sensing electrodes configured to engage with a patient's skin to detect a cardiac signal. The wearable defibrillators can include a first defibrillator electrode pad configured to engage with the patient's skin and to deliver an electrical therapy to the patient. The wearable defibrillators can include a first patient engagement substrate including an adhesive, the first defibrillator electrode pad, a first fluid transport element configured to transport fluid away from the skin to allow the wearable external defibrillator to be worn continuously, and a first vapor permeable layer. The first defibrillator electrode pad can be configured to be in continuous contact with the patient's skin. The wearable defibrillator can include a second patient engagement substrate including a second defibrillator electrode pad, a second adhesive, a second fluid transport element in fluid communication with the second patient engagement substrate configured to transport fluid away from the skin to allow the wearable external defibrillator to be worn continuously, and a second vapor permeable layer. The wearable defibrillators include an energy source, one or more capacitors in electrical communication with the energy source and the first defibrillator electrode pad and the second defibrillator electrode pad, and a controller configured to detect the cardiac signal with the one or more sensing electrodes and the sensing electrode of the second patient engagement substrate. The controller can also be adapted to charge the one or more capacitors with the energy source followed by discharging the one or more capacitors to deliver a therapeutic shock through the first defibrillator electrode pad and the second defibrillator electrode pad to the patient while the first and second patient engagement substrates are engaged with the patient. The energy source, one or more capacitors, and controller can be enclosed within one or more housings.

The one or more sensing electrodes can be separate sensors from the first and second patient engagement substrates or can be included in the first and second patient engagement substrates. In some embodiments the first patient engagement substrate includes the one or more sensing electrodes. In one example the first patent engagement substrate comprises two or more sensing electrodes. In some embodiments the second patient engagement substrate comprises a sensing electrode. In some embodiments the cardiac signal can also be sensed through the defibrillator electrode pads. For example, the first defibrillator electrode pad and second defibrillator electrode pad are adapted to detect the cardiac signal.

The defibrillator electrode pads can be in continuous direct contact with the patient's skin or in electrical contact through a conductive material, such as a conductive hydrogel or gel. The continuous contact between the defibrillator electrode pads and the patient's skin allows the device to deliver the therapeutic shock or therapy to the patient on command. The layered construction and moisture vapor transport properties of the wearable defibrillator devices described herein improve contact between the skin and the device that can allow improved comfort and for long term wear of the device.

The wearable defibrillator can include electrodes and adhesive that can be modified to improve the long term wearability of the defibrillator. A layered construction can be used to improve fluid transport away from the skin to improve the wearability of the defibrillator.

The wearable external defibrillator can be configured to be worn continuously during movement and showering activities for greater than about 24 hours. The wearable external defibrillator can be configured to be worn continuously during movement and showering activities for greater than about 5 days. The wearable external defibrillator can be configured to be worn continuously during movement and showering activities for greater than about 7 days. The wearable external defibrillator can be configured to be worn continuously during movement and showering activities for greater than about 10 days.

FIG. 1 illustrates a wearable defibrillator 100 on a patient. The wearable defibrillator 100 includes an upper patch or upper patient engagement substrate 102 and a lower patch or lower patient engagement substrate 104. The lower patient engagement substrate 104 supports one or more housings 106 that contain the device electronics. A cable 108 provides electrical communication between the upper patch 102 and lower patch 104. Each of the upper and lower patient engagement substrates include a defibrillator electrode pad and one or more ECG sensing electrodes. The ECG sensing electrodes can provide patient data to the electronics on board the device 100 and upon determination of a treatable arrhythmia a therapeutic electrical shock can be provided to the patient through the defibrillator electrode pads on the patient engagement substrates 102, 104.

The one or more housings can include a first controller housing with the controller included in the first controller housing. The one or more housings can include a first energy source housing with the energy source included in the first energy source housing. The one or more housings can include a first capacitor housing and a second capacitor housing with the capacitors included in the first capacitor housing and the second capacitor housing.

The first controller housing can include a first controller housing electrical connection. The first energy source housing can include a first energy source housing electrical connection. The first capacitor housing can include a first capacitor electrical connection and the second capacitor housing can includes a second electrical connection. The housing electrical connections can engage within the flexible circuit within the patch. The wearable defibrillator can include a mechanical connection between each of the first controller housing, first energy source housing, first capacitor housing, and second capacitor housing.

The wearable defibrillator can include a flexible circuitry. The flexible circuity can include one or more rigid printed circuit boards (PCBs). The flexible circuity can be within the patient engagement substrate and/or within one or more of the housings. The flexible circuitry can be adapted to receive the first controller housing electrical connection, the first energy source housing electrical connection, the first capacitor electrical connection, and the second electrical connection. The flexible circuitry can be in electrical communication with the first controller housing, first energy source housing, first capacitor housing, and second capacitor housing.

The flexible circuitry provides electrical communication between the first controller housing and the first energy source housing, first capacitor housing, and second capacitor housing. The flexible circuitry can be supported by the first patient engagement substrate between the first vapor permeable layer and the first defibrillator electrode pad.

In some embodiments the first patient engagement substrate is adapted to support the one or more housings. In some embodiments the second patient engagement substrate is adapted to support the one or more housings.

The first patient engagement substrate and second patient engagement substrate can be configured to be worn during showering activities.

The vapor permeable layer can be made out of flexible material. In some embodiments the vapor permeable layer is a fabric with a woven or non-woven construction. A portion of the first vapor permeable layer can represent an exterior surface of the first patient engagement surface. A portion of the second vapor permeable layer can represent an exterior surface of the second patient engagement surface. The exterior surfaces of the first patient engagement substrate and the second patient engagement substrate can be moisture vapor permeable. The exterior surfaces of the first patient engagement substrate and the second patient engagement substrate can have a moisture vapor transport above about 10 g/m$^2$ per day based on a surface area of the patient engagement substrate. The exterior surfaces of the first patient engagement substrate and the second patient engagement substrate can have a moisture vapor transport above about 1000 g/m² per day based on a surface area of the patient engagement substrate. The exterior surfaces of the first patient engagement substrate and the second patient engagement substrate can have a moisture vapor transport above about 2000 g/m² per day based on a surface area of the patient engagement substrate. The exterior surfaces of the first patient engagement substrate and the second patient engagement substrate can have a moisture vapor transport above about 3000 g/m² per day based on a surface area of the patient engagement substrate. The exterior surfaces of the first patient engagement substrate and the second patient engagement substrate can have a moisture vapor transport above about 4000 g/m² per day based on a surface area of the patient engagement substrate. The exterior surfaces of the first patient engagement substrate and the second patient engagement substrate can have a moisture vapor transport above about 5000 g/m² per day based on a surface area of the patient engagement substrate. The exterior surfaces of the first patient engagement substrate and the second patient engagement substrate can have a moisture vapor transport above about 6000 g/m² per day based on a surface area of the patient engagement substrate. The exterior surfaces of the first patient engagement substrate and the second patient engagement substrate can have a moisture vapor transport above about 7000 g/m² per day based on a surface area of the patient engagement substrate. The exterior surfaces of the first patient engagement substrate and the second patient engagement substrate can have a moisture vapor transport above about 8000 g/m² per day based on a surface area of the patient engagement substrate. The exterior surfaces of the first patient engagement substrate and the second patient engagement substrate can have a moisture vapor transport above about 9000 g/m² per day based on a surface area of the patient engagement substrate. The exterior surfaces of the first patient engagement substrate and the second patient engagement substrate can have a moisture vapor transport above about 10000 g/m² per day based on a surface area of the patient engagement substrate.

In some cases the exterior surfaces of the first patient engagement substrate and the second patient engagement substrate can be air permeable. In some embodiments the exterior surfaces of the first patient engagement substrate and the second patient engagement substrate are waterproof. The exterior surfaces of the first and second patient engagement substrates can be hydrophobic. In some cases the exterior surfaces of the first and second patient engagement substrates are water resistant. Examples of vapor permeable layers include: Gore Tex®, water proof fabrics, water resistant fabrics, water repellant fabrics, fabrics with a hydrophobic surface, waterproof non-woven fabrics, etc. Other examples of vapor permeable layers include laminated membranes, multi-layer structures, materials with ePTFE (expanded polytetrafluoroethylene) coatings, polyurethanes, etc.

The first fluid transport element and second fluid transport element can be configured to transport fluid away from the skin. The fluid transport element can be a wicking material that improves fluid transport from the side of the patient engagement substrate that contacts the skin and the outer vapor permeable surface of the wearable defibrillator. The fluid transport element can have a flexible sheet like configuration. The fluid transport element can have a woven or non-woven configuration. Examples of fluid transport materials include cotton, polyester, cellulose, reticulated polyurethane foam, and non-woven constructions.

The wearable defibrillators can include a support chassis disposed between the one or more housings and the first defibrillator electrode pad. The support chassis can be adapted to spread a shear load of the one or more housings across a dominant surface of the support chassis. The support chassis can have a sheet like configuration. In some embodiments multiple support chassis layers can be used in the patient engagement substrate. One support chassis layer could be made out of a more flexible material and another support chassis material that is more rigid could be attached or engaged with the support chassis layer. The support chassis can have a flexible or semi-rigid structure. Examples of support chassis materials include PVC, EVA, polyethylene, nylon, polyurethane, etc. In some embodiments the support chassis layer may have poor fluid transport properties. A plurality of openings or pores can be included in the support chassis material to improve fluid movement across the support chassis layer.

The wearable defibrillators can include a structural ring or other support structure to improve the spread of the weight of the device across the surface area of the patient engagement substrate. The structural rings can be used in combination with the support chassis to support any heavier or rigid components engaged with the patient engagement substrate, such as the housings containing the electronics modules. The structural rings can also provide an opening to accommodate the electrical connection between the electronics components in the one or more housings and a flexible circuit within the patient engagement substrate. The support rings can include a rigid component and flexible component. The support rings can be bonded or attached directly to the support chassis layer. The structural rings can help prevent the patient engagement substrate and prevent or reduce buckling of the patient engagement substrate from the weight of the housings and electronics components. The structural rings can help keep the patient engagement substrate relatively flat and to reduce buckling and separation between the patient engagement substrate and the skin of the patient. The structural rings can include perforations or pores to allow moisture to pass through the structural rings. The structural rings can also include a perforations to allow the structural rings to flex but not buckle. Examples of materials that can be used in the structural rings include nylon, polyethylene, ABS, polypropylene, PET, and other thermoplastic materials that can be molded or cut from sheets.

A variety of sensors and modules can be included within the one or more housings of the wearable defibrillator. The sensors and modules can be included on a PCB within the housing or in the layered construction of the patient engagement substrates, such as the conductive gels. The controller or processor of the wearable defibrillator can be configured to analyze data recorded by any of the sensors and modules described herein. In one example the wearable defibrillator includes a temperature sensor. In one example the wearable defibrillator includes a pulse oximeter configured to measure an oxygen content of a blood of the patient at a point on a chest of the patient. In one example the wearable defibrillator includes an ultrasound transceiver or transducer configured to transmit and/or receive ultrasonic signals. In one example the wearable defibrillator includes a Doppler radar configured to transmit a microwave signal and receive a returned microwave signal. In one example the wearable defibrillator includes an inclinometer configured to determine the position and orientation of the wearable defibrillator. In one example the wearable defibrillator includes a radio beacon configured to transmit the location of the wearable defibrillator. In one example the wearable defibrillator includes a GPS sensor. In one example the wearable defibrillator includes an accelerometer. In one example the wearable defibrillator includes a microphone. In one example the wearable defibrillator includes a wireless radio configured to wirelessly transmit data from the wearable defibrillator. The wireless radio can be configured to transmit data over a cellular network or Wi-Fi network. In one example the wearable defibrillator includes a sensor configured to measure a mechanical stretch of a portion of the wearable defibrillator. In one example the wearable defibrillator can include a magnetometer. In one example the wearable defibrillator can include impedance sensors, such as galvanic skin impedance sensors.

In one example the wearable defibrillator includes a tactile feedback module. The tactile feedback module can be part of the first patient engagement substrate or second patient engagement substrate. The tactile feedback module can be part of the one or more housings. In one example the tactile feedback module is a vibration motor.

In one example the wearable defibrillator includes an external pacing module configured to provide a pacing signal to the patient. The external pacing module can be supported by the first or second patient engagement substrate.

In one example the wearable defibrillator includes a skin contact module configured to sense removal of the first and/or second patient engagement substrate from the patient's skin. The skin contact module can be configured to generate an alarm and/or notification to a healthcare provider upon sensing removal of the first and/or second patient engagement substrate from the patient's skin.

The wearable defibrillators can include a connector plug on the housing with a plurality of electrical connections. The plurality of electrical connections can include a first defibrillator electrode pad connection and a second defibrillator electrode pad connection. The first defibrillator electrode pad connection and the second defibrillator electrode pad connection can be configured to be in electrical communication with the one or more capacitors and the first and second defibrillator electrode pads. The plurality of electrical connections can also include a plurality of sensing electrode connections. The plurality of sensing electrode connections can be each configured to be in electrical communication with the controller and one of the one or more sensing electrodes. The wearable defibrillator can include an enclosure configured to surround the housing with an enclosure connection having a first side with a complementary structure configured to engage with the connector plug on the housing. A second side of the enclosure connection can be configured to engage with a patient engagement substrate connector on the first patient engagement substrate. The patient engagement substrate connector can be in electrical communication with the one or more capacitors and the first and second defibrillator electrode pads.

In some embodiments the adhesive can include a plurality of pores configured to allow the transport of vapor.

In some embodiments ECG sensing electrodes and defibrillator electrode pads can include a plurality of pores configured to allow the transport of vapor. The pores can improve the fluid transport properties of the electrodes. The size, shape, and number of the plurality of pores can be configured to minimize the transport of liquid droplets.

In some embodiments the defibrillator electrode pads can include a conductive adhesive and a conductive electrode. In one example the conductive electrodes can have a solid construction. In another example the conductive electrodes can be made from a flexible sheet having a plurality of perforations. Examples of conductive electrode materials include a carbon vinyl film, Ag/AgCl coated carbon vinyl film, polyethylene terephthalate (PET) films, Ag coated carbon vinyl film, electrodes with a conductive ink, PET coated with carbon, PET films with conductive coatings, PET coated with Ag/AgCl, PET coated with Ag, etc.

The conductive ink can be applied to the electrode substrate with a desired thickness. Generally, the thicker the conductive ink coating the higher the conductivity. The thickness of the conductive ink can be uniform in some embodiments. The conductive ink can be depleted while sending a direct current to the patient through the defibrillator electrode pads. The conductive ink can be provided on the electrode substrate with a thickness sufficient to last through providing a defibrillating shock. In embodiments that use a conductive electrode substrate, like a carbon vinyl substrate, the underlying electrode substrate is conductive and can continue to provide current even in areas where the conductive ink has been depleted.

In another example the conductive electrodes of the defibrillator electrode pads can have a woven structure. In one example the conductive electrode can include carbon fiber.

In some embodiments the conductive adhesive is a conductive hydrogel. In some embodiments the conductive adhesive can include a salt. In some embodiments the conductive adhesive is an adhesive with a conductive filler. The conductive filler can include one or more of: carbon nanotubes, graphene, carbon black, silver particles, metal particles, and silver nanowires.

The first and second patient engagement substrates can be configured to insulate between the sensing electrodes, the defibrillator electrode pad, and other portions of the patient engagement substrate. In one example an adhesive on the first and second patient engagement substrates is non-conductive and can be used to insulate the electrodes.

In some embodiments the electronics components can be configured to be reversibly and removably engaged with a portion of the wearable defibrillator. The one or more capacitors can be configured to be reversibly and removably engaged with the wearable defibrillator. The energy source can be configured to be reversibly and removably engaged with the wearable defibrillator. The controller/processor can be configured to be reversibly and removably engaged with the wearable defibrillator.

In some embodiments the housing includes a plurality of compartments containing the energy source, one or more capacitors, and controller. The wearable defibrillator can include a flexible circuitry and one or more rigid printed circuit boards (PCBs) within the housing. The plurality of compartments can be in fluid communication within the housing. In some cases the plurality of compartments may not be in fluid communication with the other of the plurality of compartments. In some cases the plurality of compartments are separate and configured to reversibly engage with the other of the plurality of compartments. In some embodiments the plurality of compartments are connected with a plurality of waterproof connector segments.

The housing can be configured to allow relative movement between the plurality of compartments of the housing. The relative movement can include flexing with a plane of the first patient engagement substrate.

The housing can include an outer clam shell and a base. The outer clam shell and base can be secured together with mechanical or chemical fixation. In one example the outer claim shell can be attached and sealed to the base with screws and a gasket, plastic snap hooks and a gasket, or other mechanical fixation structures. The outer clam shell can be ultrasonically welded to the base. The outer clam shell can be attached to the base with an adhesive. The outer clam shell can be attached to the base through chemical bonding. In some embodiments the one or more housings each have a clam shell configuration sealed with an adhesive. In some embodiments the one or more housings each have a clam shell configuration sealed through chemical bonding. In some examples ultrasonic welding can be used to secure the outer clam shell to the base.

In some embodiments the one or more sensing electrodes of the first patient engagement substrate and the sensing electrode of the second patient engagement substrate and the first and second defibrillator electrode pads can be configured to sense impedance changes along a plurality of vectors of the patient. The controller can be configured to analyze the impedance changes along the plurality of vectors of the patient to measure a cardiac health of the patient.

In some embodiments the controller is configured to analyze an impedance between one or more of: the one or more sensing electrodes, the first defibrillator electrode pad, the second defibrillator electrode pad, and the sensing electrode. The controller can also be configured to measure the impedance using two or more discrete frequencies. For example, the two or more discrete frequencies can include a high frequency measurement and a low frequency measurement. The controller can analyze the high frequency measurement and low frequency measurement to determine a power of the therapeutic shock for the patient based on the impedance.

The moisture vapor transmission rate of the patient engagement substrate can be configured to transport moisture from the skin. The moisture vapor transport properties can also be measured across each of the patient engagement substrates. The ability of the patient engagement substrate to move moisture/vapor from the patient engagement portion (e.g., adhesive, sensing electrode gel, and defibrillator electrode pad gel) of the wearable defibrillator through the device and across the outer surface on the side of the patient engagement substrate opposing the adhesive and gels (e.g., vapor permeable layer) can be measured. The upper and lower patient engagement substrates can have similar moisture vapor transport properties. The moisture vapor transmission rate can be the average moisture vapor transmission across the total surface area of the patient engagement surface. In some embodiments the first or second patient engagement substrate includes a moisture vapor transport above about 10 g/m$^2$ per day based on a surface area of the patient engagement portion through the patient engagement portion and the first or second vapor permeable layer. In some embodiments the first or second patient engagement substrate includes a moisture vapor transport above about 50 g/m$^2$ per day based on a surface area of the patient engagement portion through the patient engagement portion and the first or second vapor permeable layer. In some embodiments the first or second patient engagement substrate includes a moisture vapor transport above about 100 g/m$^2$ per day based on a surface area of the patient engagement portion through the patient engagement portion and the first or second vapor permeable layer. In some embodiments the first or second patient engagement substrate includes a moisture vapor transport above about 150 g/m$^2$ per day based on a surface area of the patient engagement portion through the patient engagement portion and the first or second vapor permeable layer. In some embodiments the first or second patient engagement substrate includes a moisture vapor transport above about w00 g/m$^2$ per day based on a surface area of the patient engagement portion through the patient engagement portion and the first or second vapor permeable layer. In some embodiments the first or second patient engagement substrate includes a moisture vapor transport above about 500 g/m$^2$ per day based on a surface area of the patient engagement portion through the patient engagement portion and the first or second vapor permeable layer. In some embodiments the first or second patient engagement substrate includes a moisture vapor transport above about 1000 g/m$^2$ per day based on a surface area of the patient engagement portion through the patient engagement portion and the first or second vapor permeable layer. In some embodiments the first or second patient engagement substrate includes a moisture vapor transport above about 1500 g/m$^2$ per day based on a surface area of the patient engagement portion through the patient engagement portion and the first or second vapor permeable layer.

In some embodiments the lower or first patient engagement substrate has a preformed curvature. The preformed curvature can correspond to a shape of a human torso. In some embodiments the upper or second patient engagement substrate has a preformed curvature. The preformed curvature of the upper patient engagement substrate can correspond to a shape of a human chest.

A cable can form an electrical communication between the first patient engagement substrate and the second patient engagement substrate. For example the cable forms the electrical communication between the sensing electrode of the second patient engagement substrate and the controller. The cable can also form an electrical communication between the second defibrillator electrode pad and the one or more capacitors.

The wearable defibrillator can include a display indicator. The display indicator can be part of the first patient engagement substrate or second patient engagement substrate. The display indicator can be part of the one or more housings. The display indicator can be part of a cable between the first patient engagement substrate or second patient engagement substrate. In one example the display indicator is a light emitting diode (LED).

The wearable defibrillators can include one or more buttons on the one or more housings alone or in combination with a display. The buttons can be a mechanical switch, button, or capacitive switch.

Figure 2A:
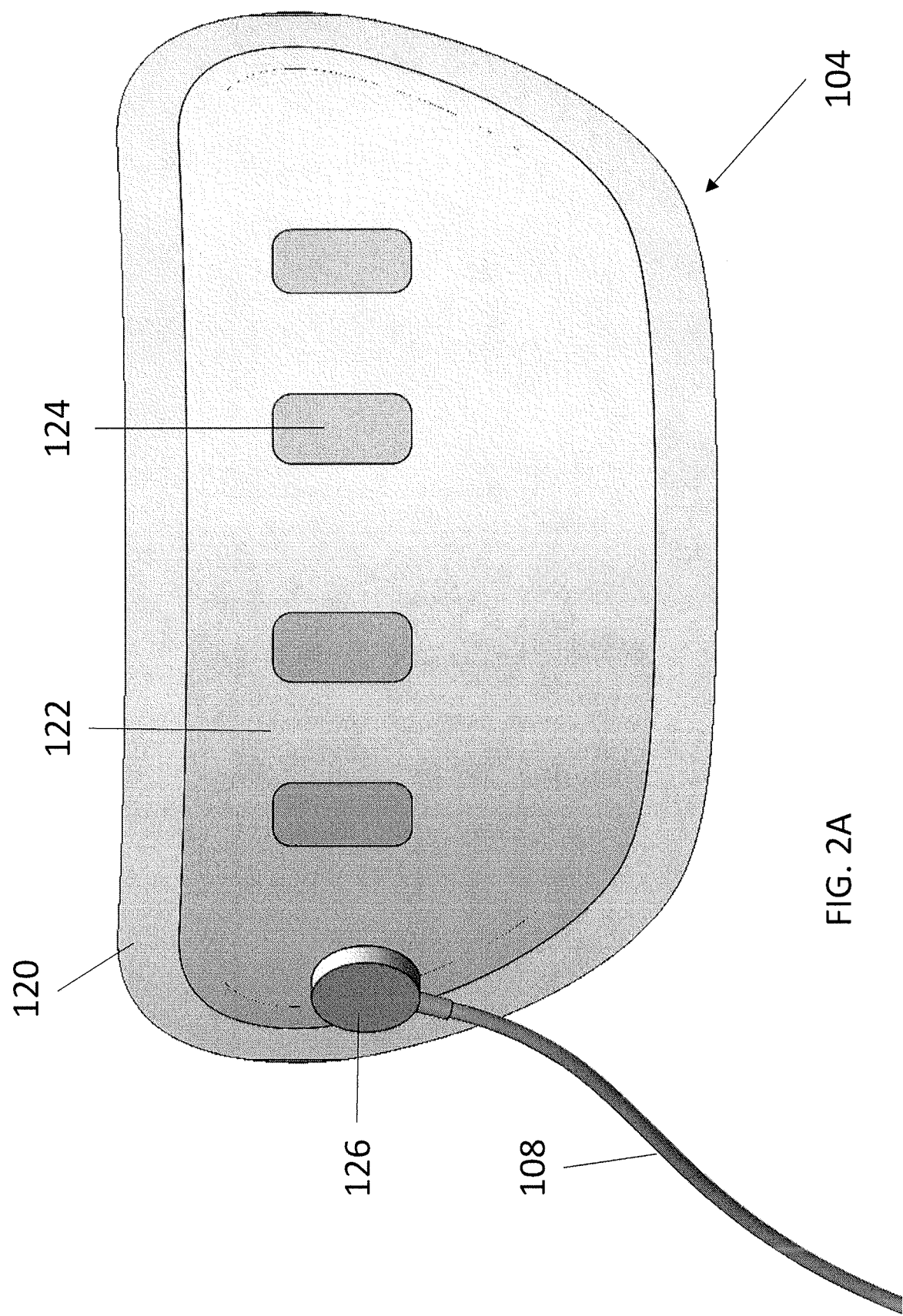
FIGS. 2A-2D illustrate various views of a patient engagement substrate that is part of a wearable defibrillator in accordance with some embodiments.

FIGS. 2A-2D illustrate various views of the lower patient engagement substrate 104. FIG. 2A illustrates a top exterior of the lower patient engagement substrate 104 without the one or more housings 106 engaged to the lower patient engagement substrate 104. The lower patient engagement substrate 104 includes a border layer 120, a vapor permeable layer 122, a plurality of structural rings 124 at openings of the vaper permeable layer 122, and a cable connection 126 between the cable 108 and an interior of the patient engagement substrate. The border layer 120 can be ultrasonically welded or adhered to seal the edges of the patient engagement substrate to prevent water ingress to the interior of the patient engagement substrate from the sides of the patient engagement substrate. The border layer 120 can be welded to the vapor permeable layer 122 to form a seal. The border layer 120 can also include an adhesive that can adhere the patient engagement substrate to the skin of the patient.

Figure 2B:
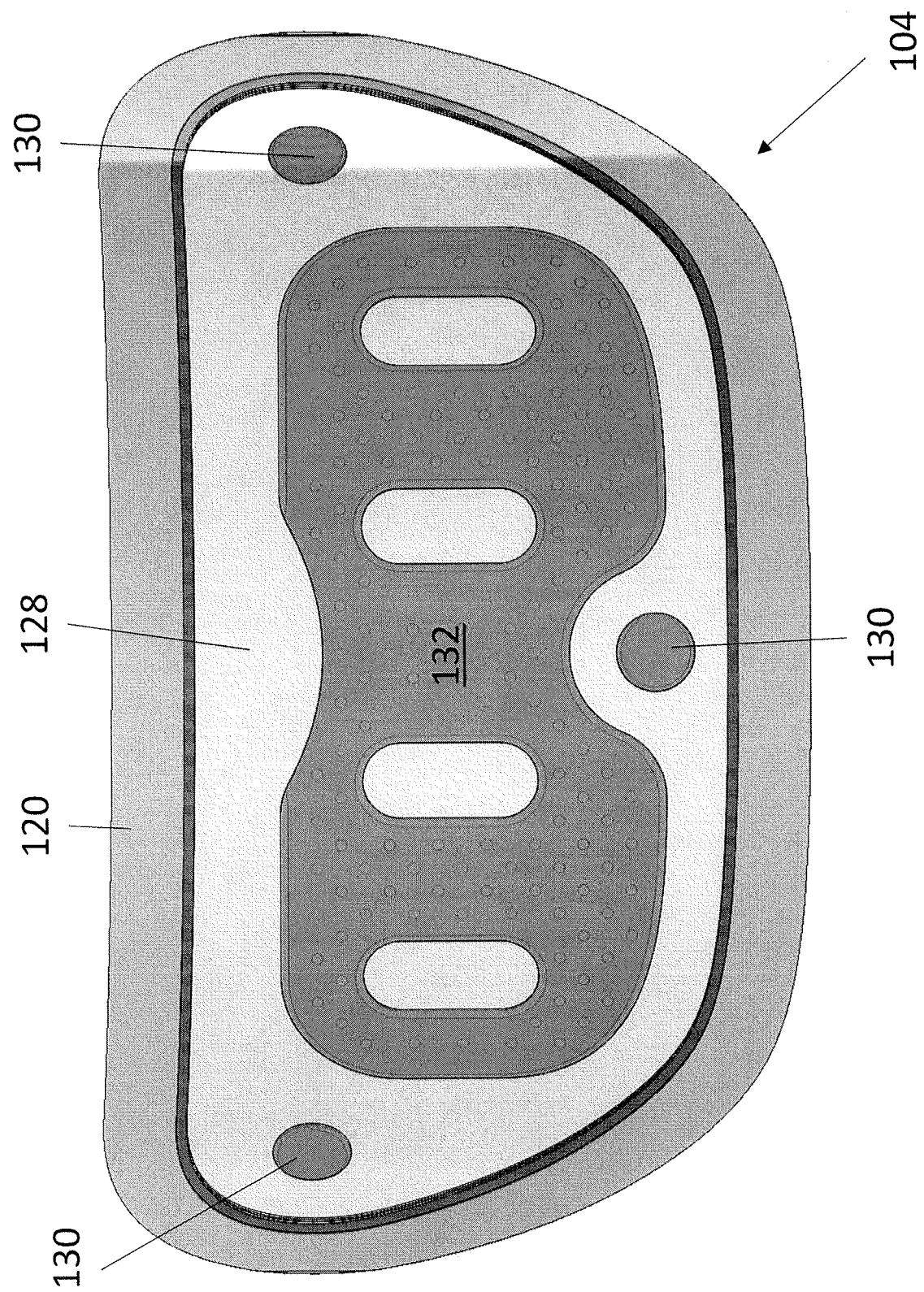

FIG. 2B illustrates a bottom exterior of the lower patient engagement substrate 104 adapted to contact the skin of the patient. The lower patient engagement substrate 104 includes an adhesive 128 adapted to engage with the skin for long term wear, a plurality of ECG sensing electrode conductive gels 130, and a defibrillator electrode pad gel 132. The ECG sensing electrode conductive gels 130 are in electrical communication with the ECG sensing electrodes. The defibrillator electrode pad gel 132 is in electrical communication with the defibrillator electrode pad to deliver a therapeutic shock upon detection of a treatable arrhythmia. The ECG sensing electrode conductive gels 130 and the defibrillator electrode pad gel 132 are conducive gels that are adapted for long term wear of the device.

Figure 2C:
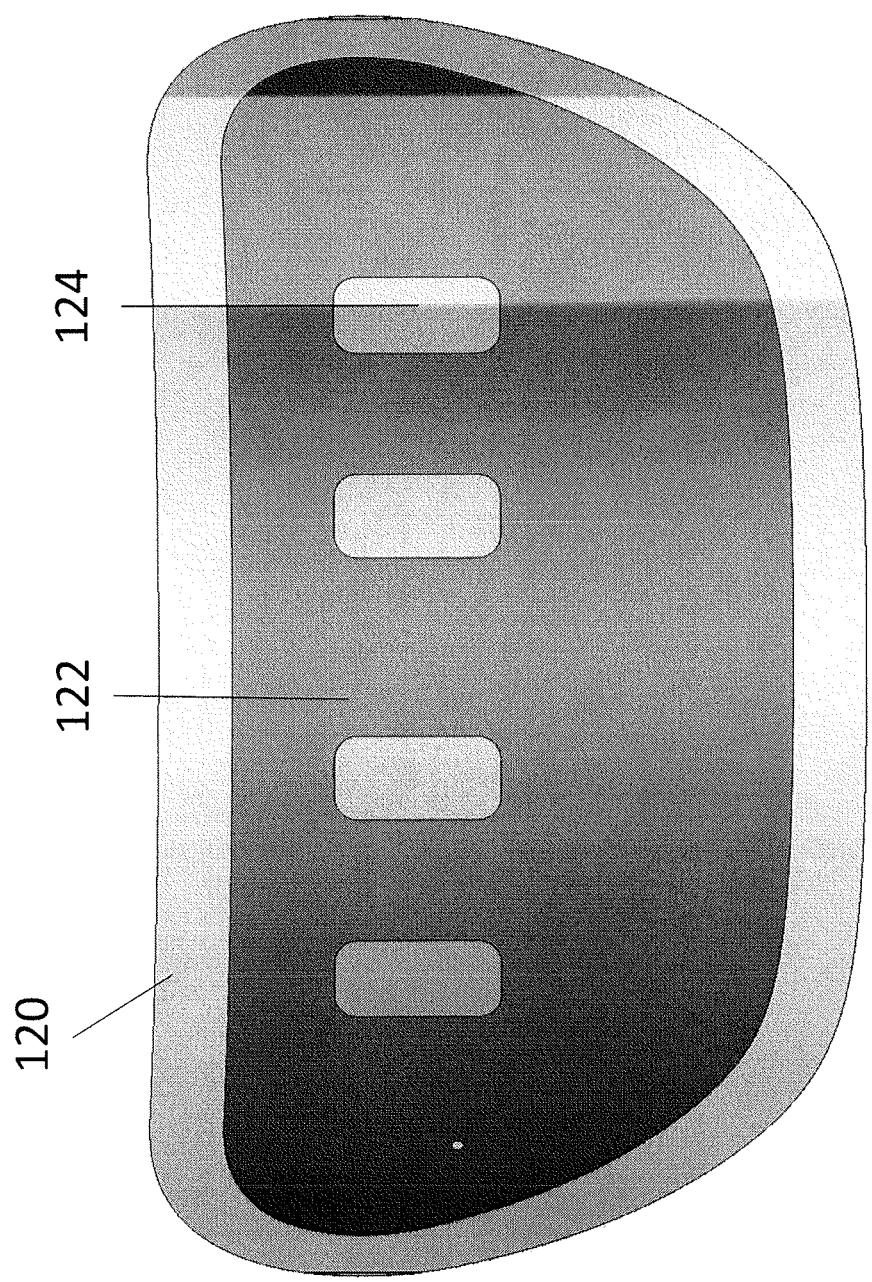
Figure 2D:
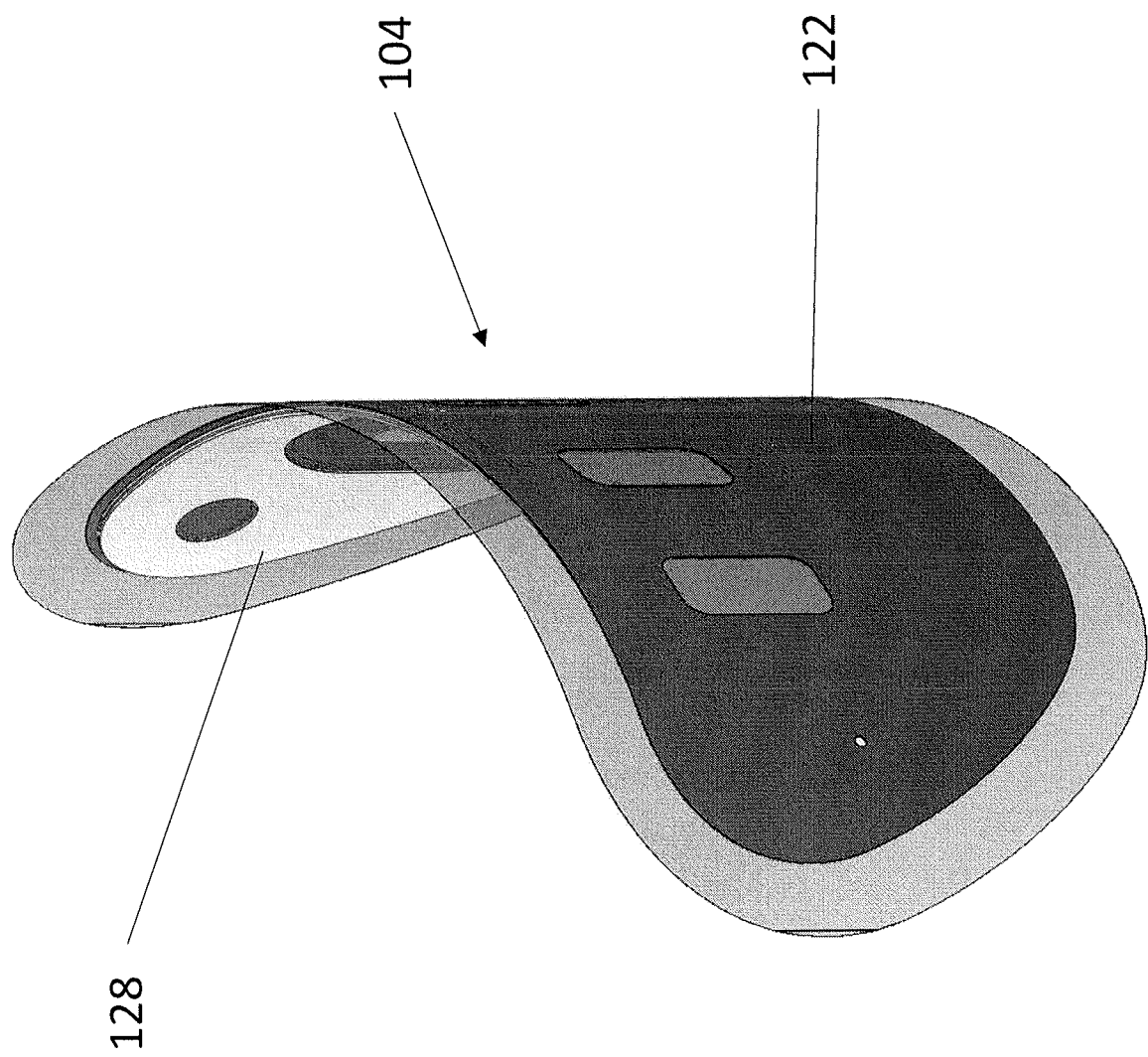

FIG. 2C illustrates the lower patient engagement surface 104 without the cable 108. FIG. 2D illustrates the lower patient engagement surface 104 having a preformed curvature. Some or all of the components in the lower patient engagement surface 104 can be assembled with a preformed curvature or processed during assembly to include a preformed curvature. The preformed curvature can be modeled after the anatomy of a human torso to improve compatibility with the lower patient engagement surface and the body of the patient. The preformed curvature can also reduce residual stresses in the device during use and improve the comfort of the device and other long term wear features of the wearable defibrillator.

Figure 3A:
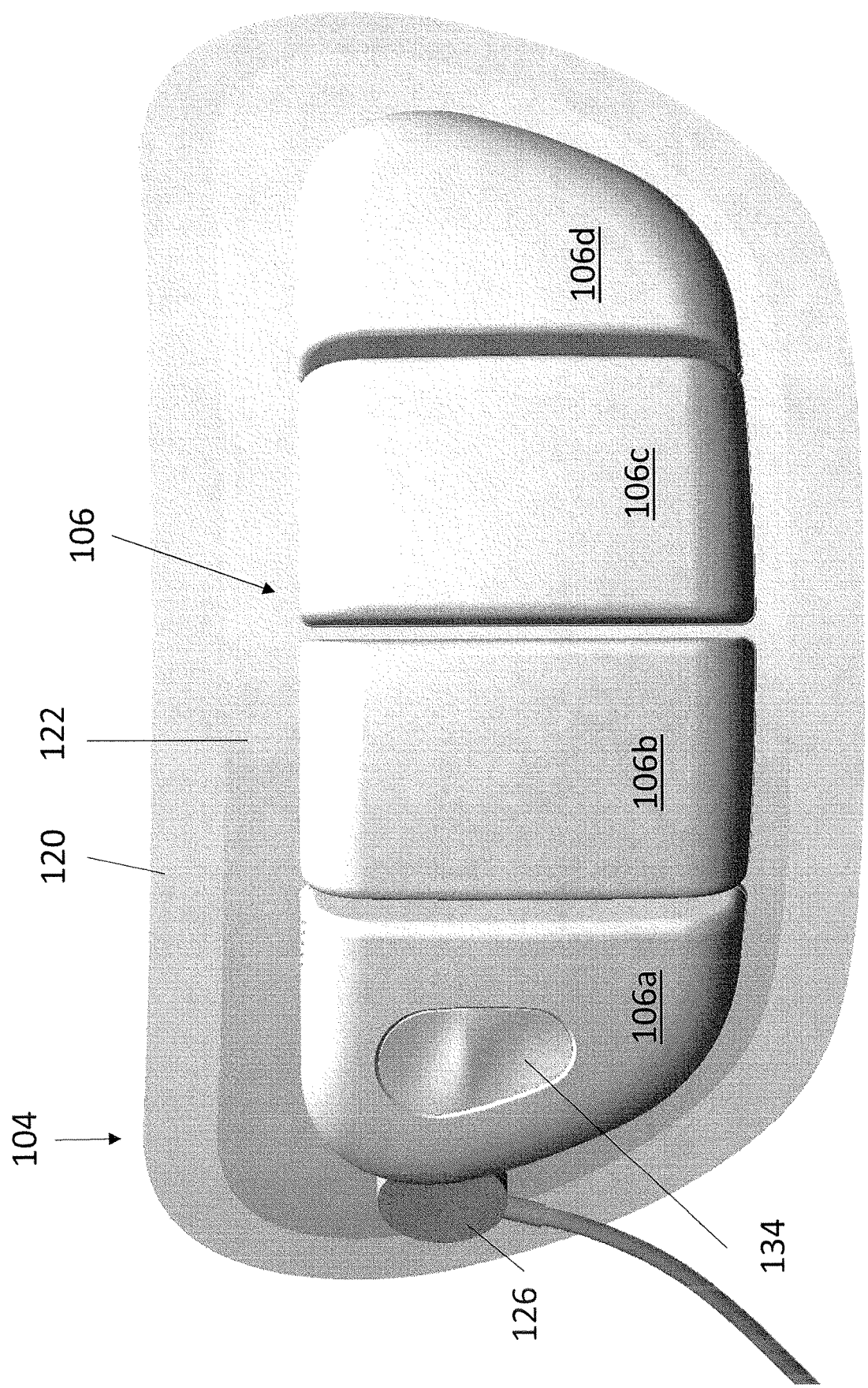
FIGS. 3A-3C illustrate an exterior view and two exploded views, respectively, of a patient engagement substrate and a plurality of housings in accordance with some embodiments.

FIG. 3A illustrates the lower patient engagement substrate 104 and one or more housings 106. The one or more housings are illustrated as housings 106a, 106b, 106c, and 106d. The housing 106a includes a button/display 134. The housing 106a can enclose and support the controller and memory 154. The housings 106b, 106c can enclose and support capacitors 156, 158 of the device 100. The housing 106d can support the energy source 160, such as a battery.

Figure 3B:
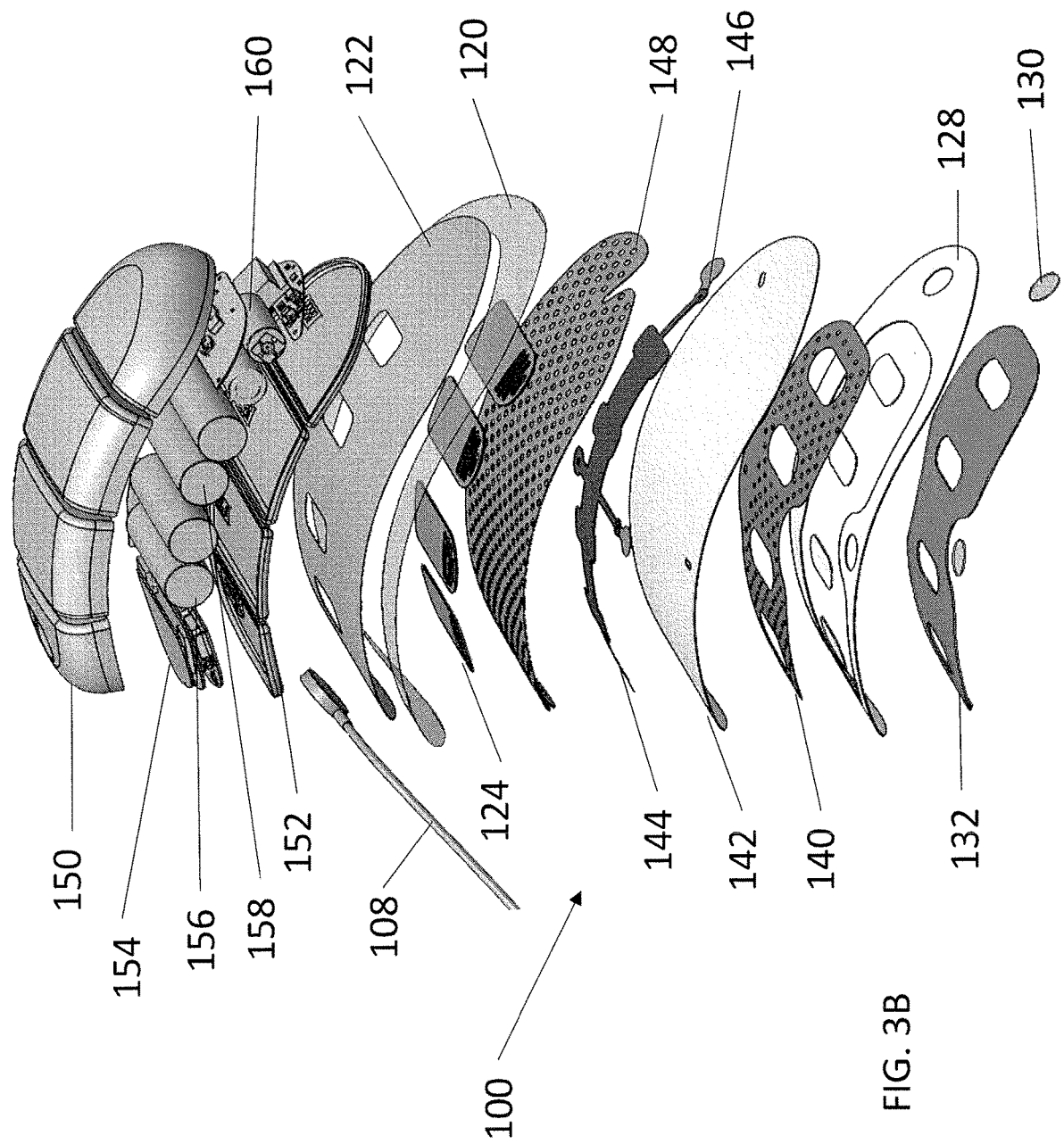
Figure 3C:
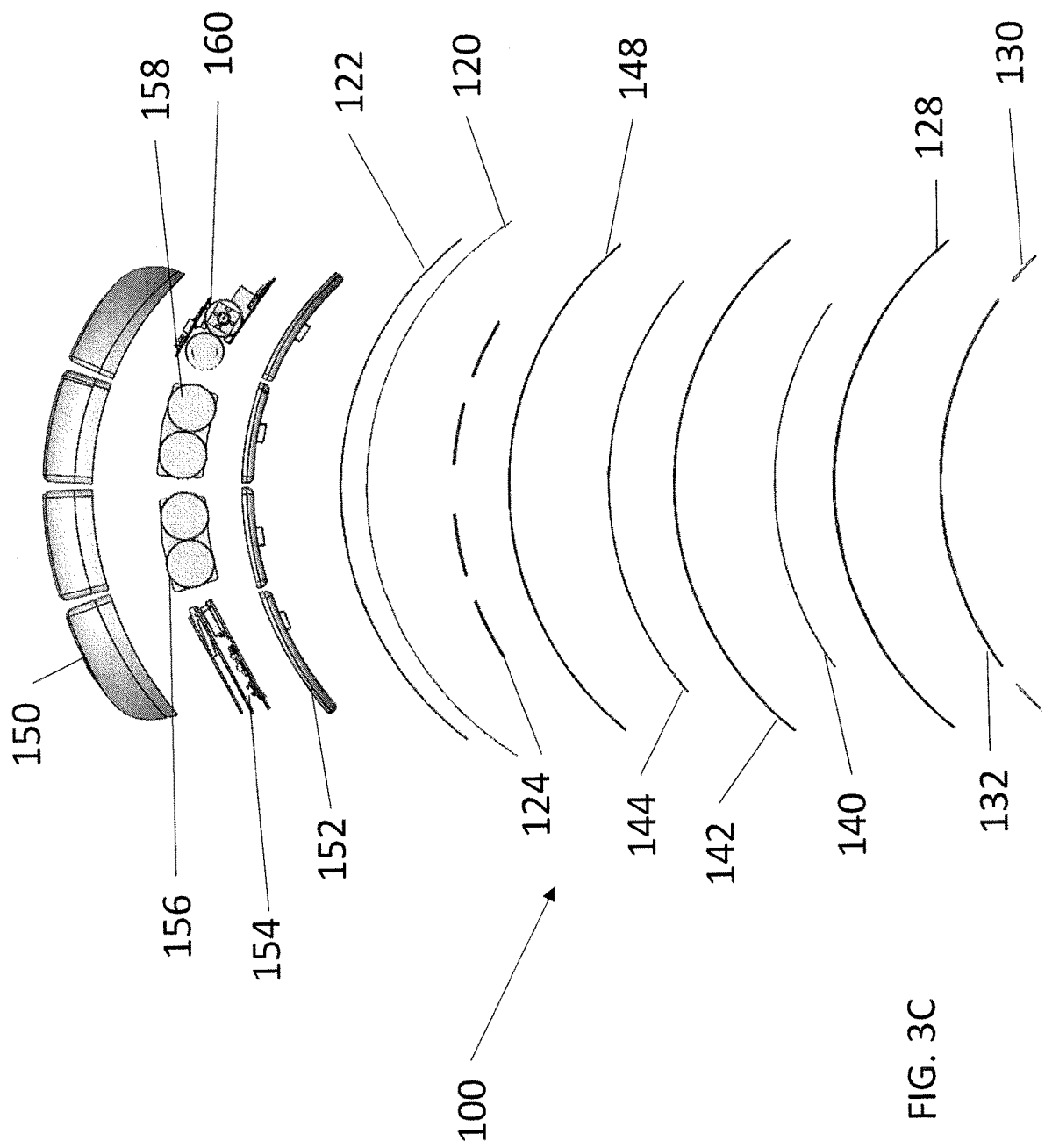

FIG. 3B illustrates an exploded view of the wearable defibrillator 100. The wearable defibrillator 100 can include an adhesive 128, ECG sensing electrode conductive gels 130, and defibrillator electrode pad gel 132. The adhesive 128 includes openings to accommodate the shapes of the ECG sensing electrode conductive gels 130 and defibrillator electrode pad gel 132. The defibrillator electrode pad gel 132 can have a shape that matches the shape of the defibrillator electrode pad 140. Electrical energy can be delivered through the defibrillator electrode pad 140 and defibrillator electrode pad gel 132 to provide a therapeutic electrical shock to the patient. The device can include a fluid transport layer 142 such as a wicking layer. The wicking layer can improve the movement of moisture from the surface of the wearable defibrillator 100 having the gels that contacts the skin through the device. Improved moisture management with the surface of the device that contacts the skins can improve the comfort of the device to the wearer. The wearable defibrillator can include a flexible circuit 144 with a plurality of ECG sensing electrodes 146. The ECG sensing electrodes 146 can be in electrical communication with the ECG sensing electrode conductive gels 130. The wearable defibrillator can include a support chassis 148 that can spread the shear force from the weight of the one or more housings 106 across a larger surface area of the device. The support chassis can improve adhesion between the adhesive 128 and conductive gels 130, 312 and the skin to support the weight of the one or more housings and electrical components. The illustrated support chassis includes a plurality of openings to improve fluid transport across the support chassis 148. The illustrated wearable defibrillator includes the border layer 120, the vapor permeable layer 122, and the plurality of structural rings 124 at openings of the vapor permeable layer 122. The border layer 120 can form a seal between the vapor permeable layer 122 and the adhesive 128 and conductive gels 130, 132. The structural rings 124 can be configured to allow electrical connections to pass through them from the flexible circuit 144 to one or more housings 106. The structural rings 124 can be engaged with or attached to the support chassis 148 to improve the ability of the device to spread the shear weight of the one or more housings across the support chassis 148 and the surface area of the patient engagement substrate. The one or more housings include an upper shell 150 and lower shell 152 that form a plurality of compartments or individual housings that receive the electrical components of the wearable defibrillator 100. A first compartment of the housing 106 includes a controller and memory 154. A second compartment of the housing 106 includes a first capacitor module 156 and a third compartment of the housing 106 includes a second capacitor module 158. A fourth compartment of the housing 106 includes the energy source 160, shown as a battery. FIG. 3C illustrates a cross-sectional view of the wearable defibrillator 100 that shows the preformed curvature of the patient engagement substrate 104.

Figure 4:
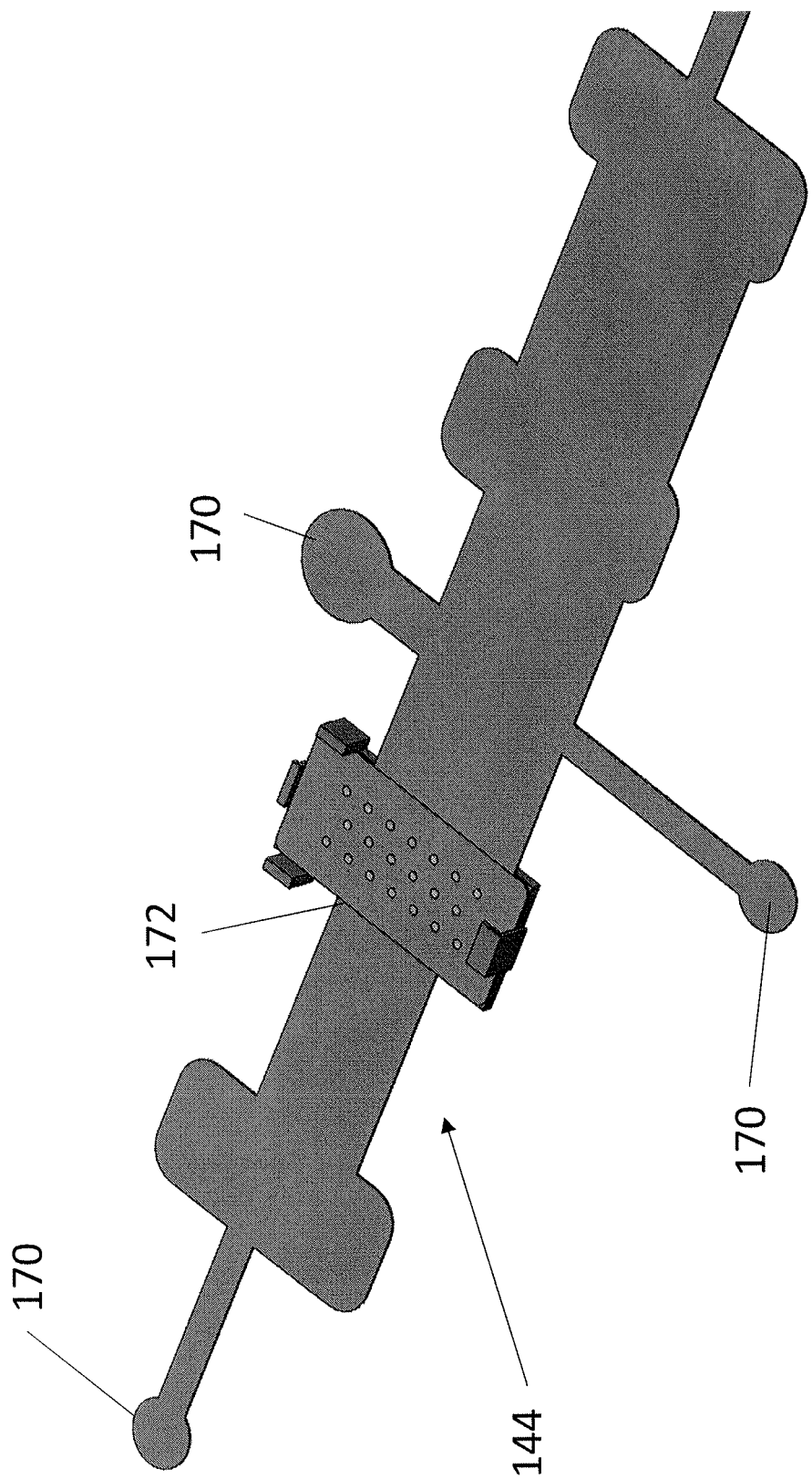
FIG. 4 illustrates a flexible circuit that can be used in the wearable defibrillators described herein.

FIG. 4 is an enlarged view of a portion of the flexible circuit 144. The flexible circuit includes a plurality of connections 170 that can be used to engage with and receive signals from the ECG sensors 146. The flexible circuit 144 can include a connector 172 that can engage with a complementary section of the one or more housings 106 to form electrical communication between the flexible circuit 144 and one or more housings 106, such as the connector shown in FIG. 9B. The flexible circuit 144 can be in electrical communication with the defibrillator electrode pad and the ECG sensors. The flexible circuit 144 can include a separate connection for each of the one or more housings.

Figure 5A:
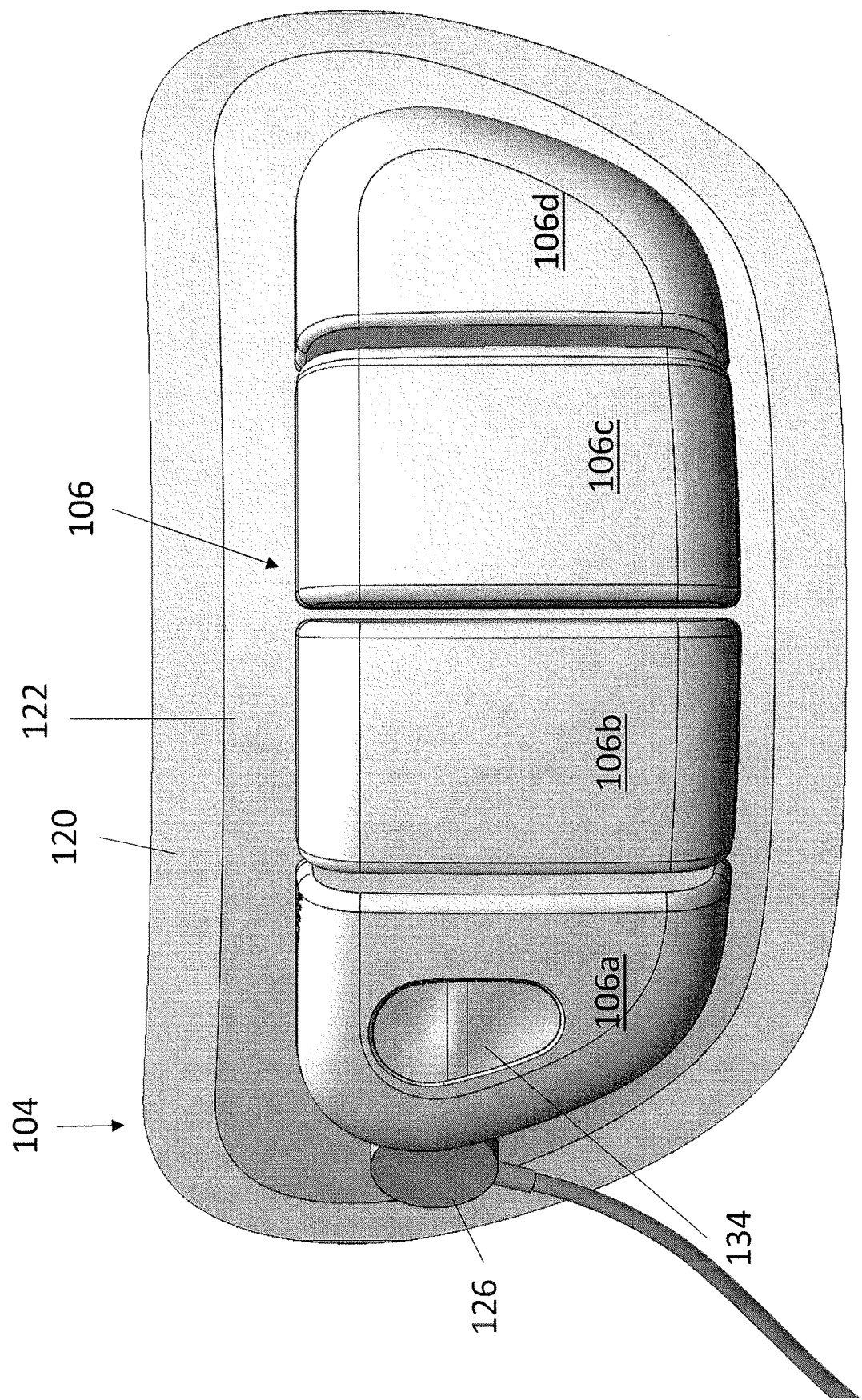
FIGS. 5A-5C illustrate an exterior view and two exploded views, respectively, of a patient engagement substrate and a plurality of housings in accordance with some embodiments.
Figure 5B:
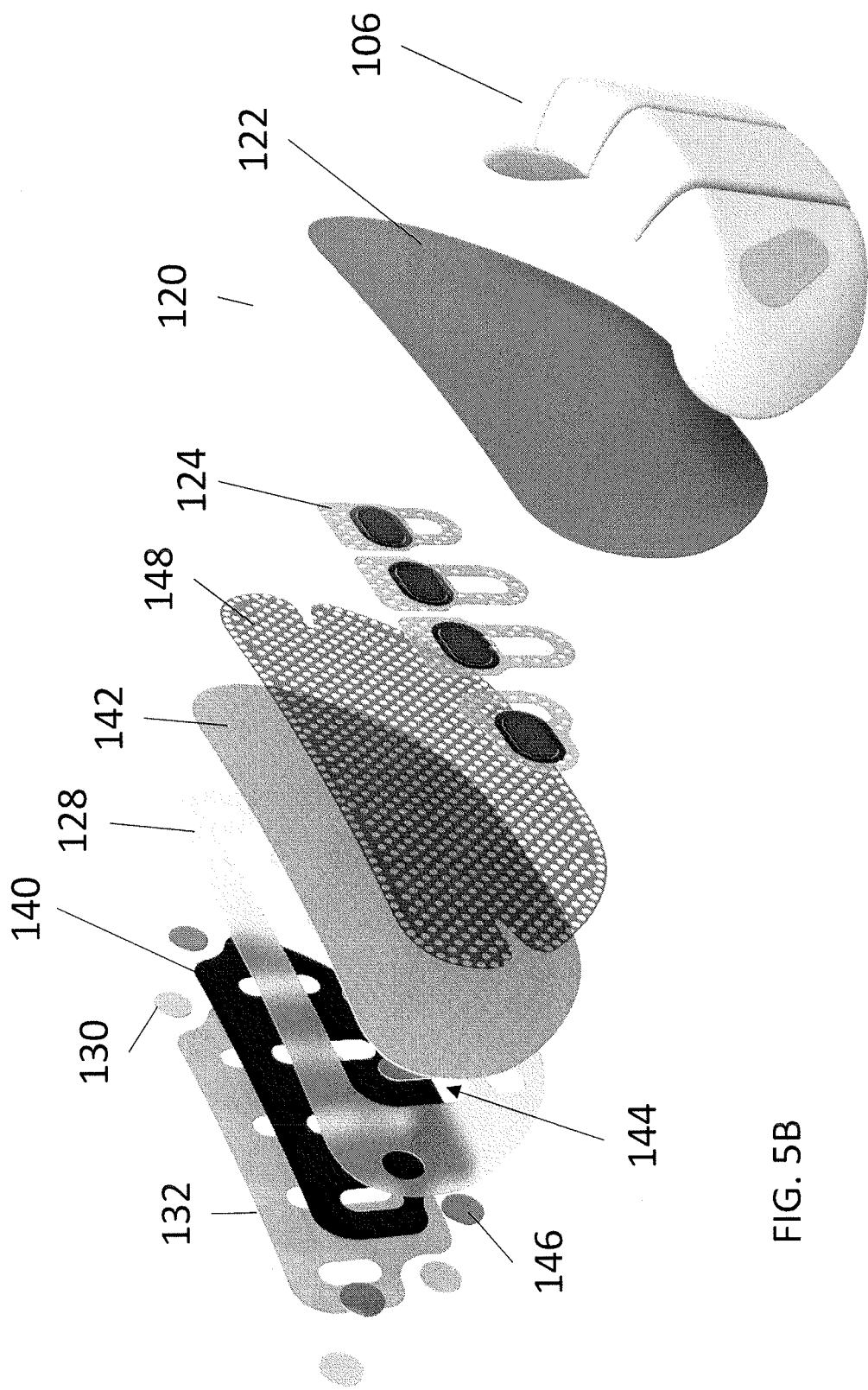
Figure 5C:
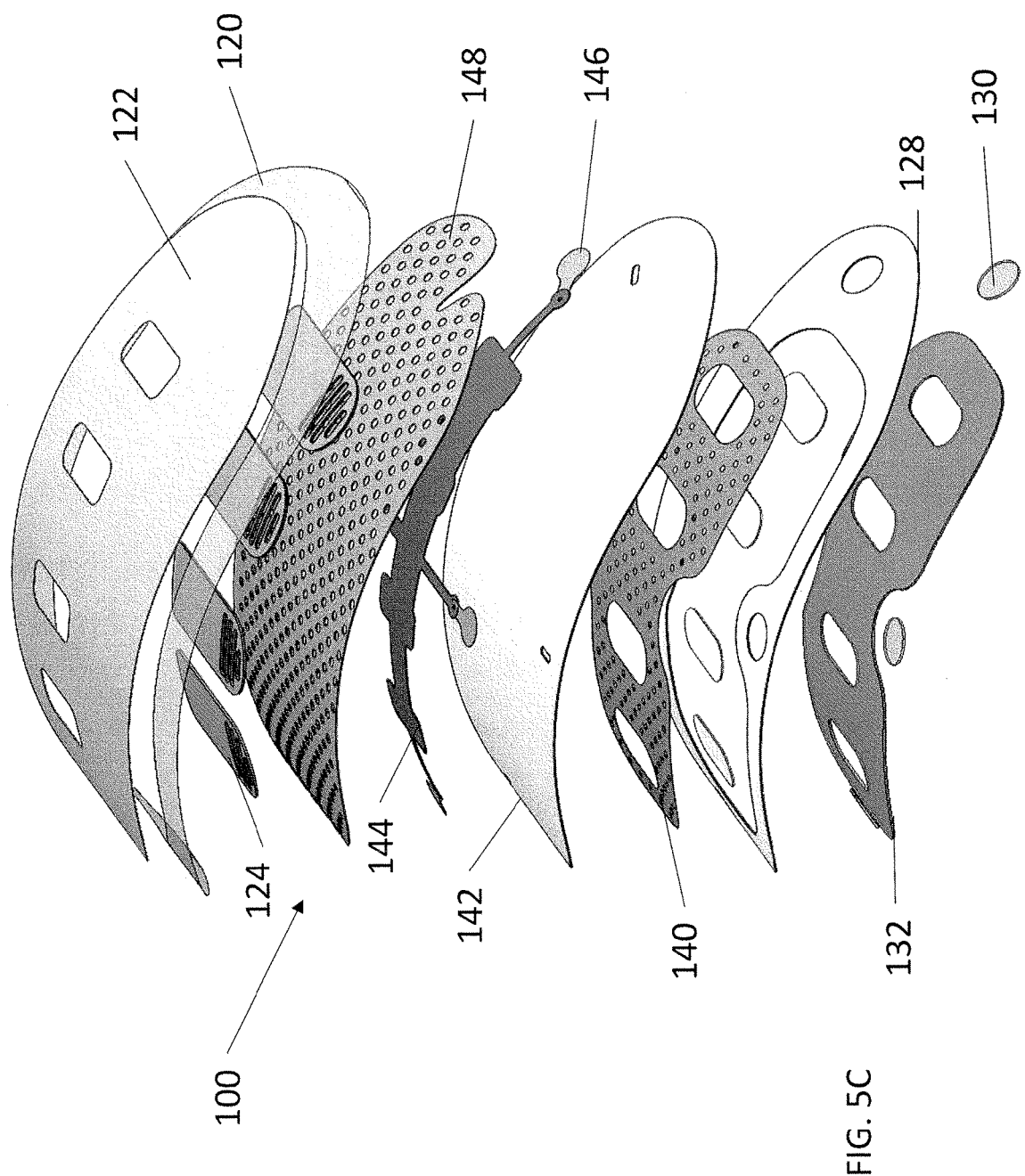

FIGS. 5A-5C illustrate a lower patient engagement substrate 104 in accordance with some embodiments. A button 134 is illustrated as a switch in the housing 106a. The housing 106 can also include a display as part of one of the housings 106a, 106b, 106c, and 106d. The illustrated lower patient engagement substrate 104 includes a different footprint and complementary shapes for the defibrillator electrode gel 132, defibrillator electrode 140, and adhesive 128. The housings 106a, 106b, 106c, and 106d are mechanically connected but electrically separated. The housings 106a, 106b, 106c, and 106d are illustrated with a preformed curvature that can match the torso anatomy. The housings 106a, 106b, 106c, and 106d also can bend relative to each other to accommodate different curvatures of the patient torso.

Figure 6:
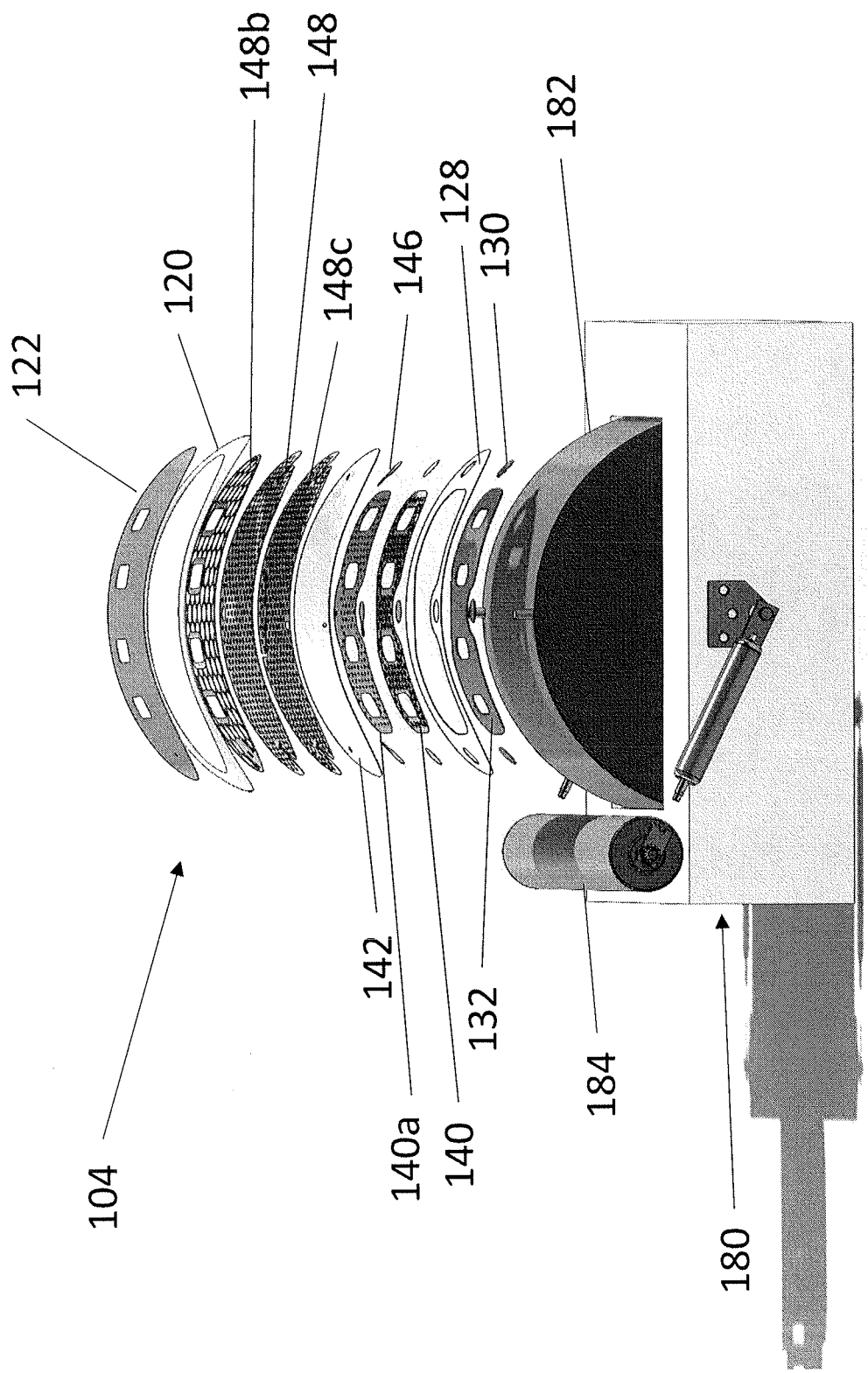
FIG. 6 illustrates a method for forming a portion of a wearable defibrillator with a patient engagement substrate having a preformed curvature in accordance with some embodiments.

FIG. 6 illustrates an apparatus 180 and process for forming the preformed curvature on the patient engagement substrate. FIG. 6 illustrates the components of a lower patient engagement substrate 104 although a similar process can be used for any of the patient engagement substrates and components described herein. The apparatus 180 includes a curved surface 182 with a curvature designed to mimic the curvature of a typical human torso. The apparatus 180 also includes a roller 184 adapted to apply pressure to the components of the patient engagement substrate to conform the components of the patient engagement substrate to the curvature of the curved surface 182. The illustrated lower patient engagement substrate 104 includes multiple adhesive bonding layers 140a, 148b, and 148c. The adhesive bonding layers have a plurality of openings that match the layers they are joining, such as the chassis layer 148 and the defibrillator electrode pad 140. The chassis layer 148 includes the structural rings for the housings. The illustrated lower patient engagement substrate 104 includes a multiple layer defibrillator electrode configuration with defibrillator electrode pad 140. The flexible circuit 144 is not shown in FIG. 6 but it can be included between the fluid transport element 142 and the support chassis 148 or between other layers of the patient engagement substrate. The patient engagement substrate can be built layer by layer on the apparatus 180. The roller 184 can be used to apply the curvature to each individual layer as it is added and/or it can be used to apply the curvature to the assembled patient engagement substrate 104. The apparatus 180 can be used to apply a preformed curvature to the patient engagement substrates such that they can have a residual stress that can improve conformity of the patient engagement substrate to the patient anatomy, such as the torso.

Figure 7A:
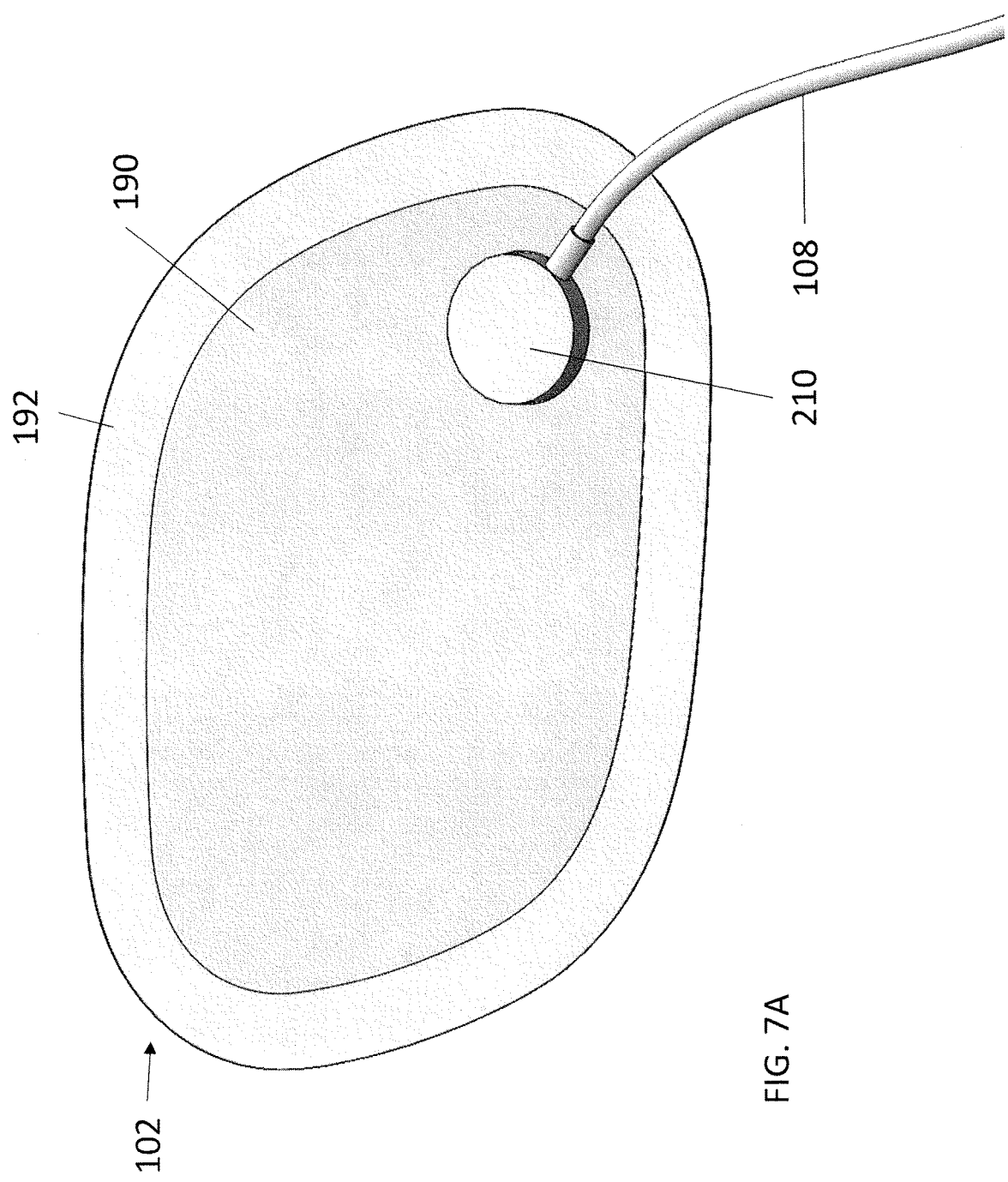

FIGS. 7A and 7B illustrate an upper patch or upper patient engagement substrate 102 in accordance with some embodiments. The upper patient engagement substrate 102 can have a generally similar construction to the lower patient engagement substrate 104. Typically, the footprint of the upper patient engagement substrate 102 can be smaller than the footprint of the lower patient engagement substrate 104 when the one or more housings are supported by the lower patient engagement substrate 104. The upper patient engagement substrate 102 can be adapted to adhere to the upper chest of the patient as shown in FIG. 1. The upper patient engagement substrate 102 has an outer surface that includes a vapor permeable membrane 190 and a border 192. The upper patient engagement substrate 102 also includes a support chassis 194, a flexible circuit 196 with an ECG sensing electrode 198, a fluid transport element 200 like a wicking layer, a defibrillator electrode pad 202, ECG sensing electrode gel 204, a defibrillator electrode pad gel 206, and adhesive 208. The upper patient engagement substrate 102 is illustrated with a single ECG sensing electrode 198. In some embodiments the upper patient engagement substrate can include two or more ECG sensing electrodes. The defibrillator pad electrodes can also be used to detect cardiac signals and work as ECG sensing electrodes. The cable 108 can engage with the upper patient engagement substrate 102 through a connector 210 to be in electrical communication with the flexible circuit 196. Data from the ECG sensing electrodes can be sent via the cable 108 to the controller and electronics in the one or more housings 106. Upon detection of a treatable arrhythmia, the controller can charge the capacitors with the energy source. After the capacitors are charged a therapeutic electrical shock can be provided to the defibrillator electrode pad 202.

Figure 8:
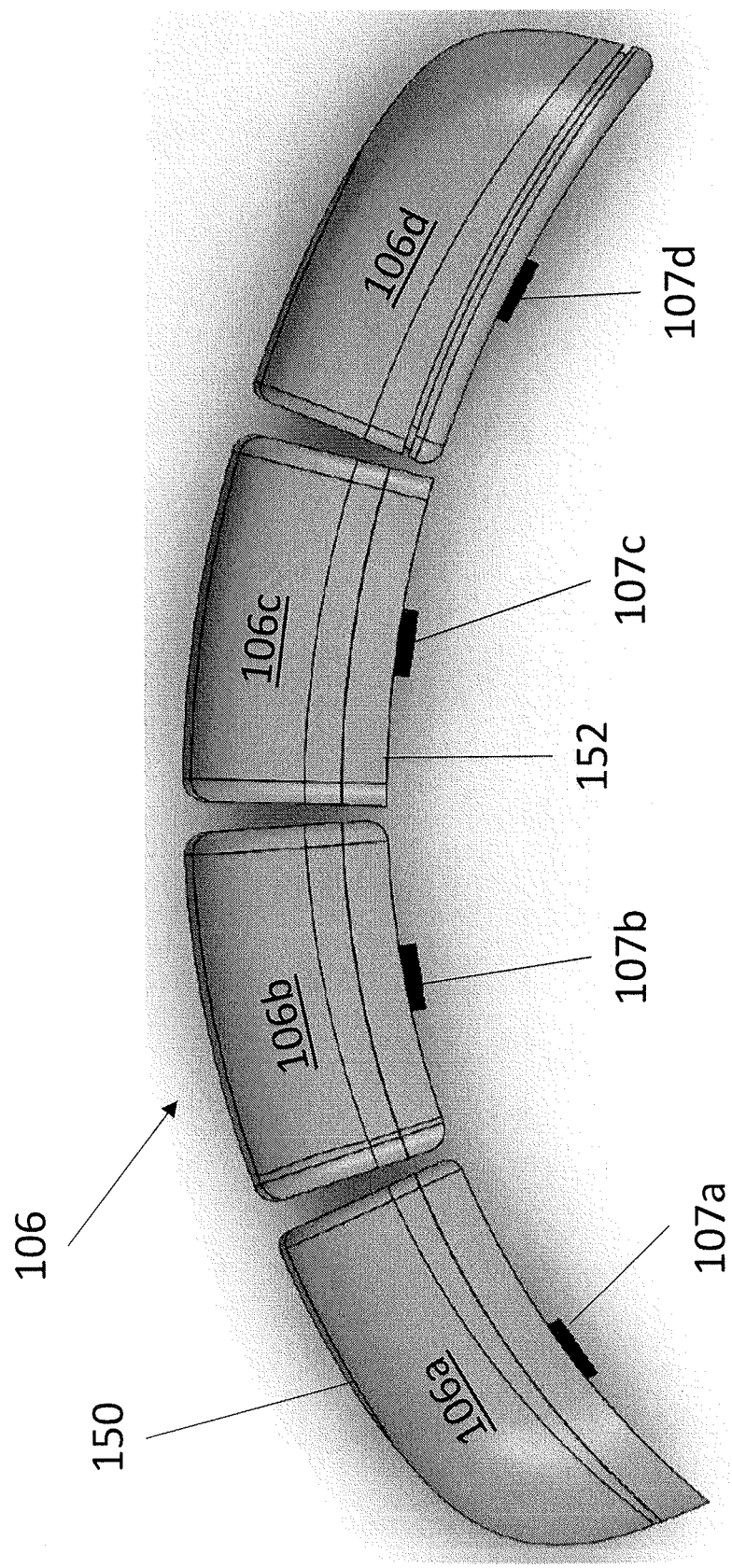
FIG. 8 illustrates a side-view of a plurality of housings that can be incorporated into the wearable defibrillators described herein.

FIG. 8 illustrates a side-view of a plurality of housings 106a, 106b, 106c, and 106d. The housings 106 are formed from an upper shell 150 and lower shell 152 that form separate interior portions for the plurality of housings 106a, 106b, 106c, and 106d of the wearable defibrillator. The housing 106a includes an electrical connector 107a adapted to electrically communicate with the flexible circuit 144. The housing 106b includes an electrical connector 107b adapted to electrically communicate with the flexible circuit 144. The housing 106c includes an electrical connector 107c adapted to electrically communicate with the flexible circuit 144. The housing 106d includes an electrical connector 107d adapted to electrically communicate with the flexible circuit 144. In one example the housing 106a can enclose and support the controller and memory 154. The electrical connection 107a can facilitate the transmission of signals between the controller and memory 154 and other device hardware via the flexible circuit 144. The housings 106b, 106c can enclose and support capacitors 156, 158 of the device 100. The electrical connections 107b, 107c can facilitate the transmission of signals between the capacitors 156, 158 and other device hardware via the flexible circuit 144. The housing 106d can support the energy source 160, such as a battery. The electrical connection 107d can facilitate the transmission of signals between the battery and other device hardware via the flexible circuit 144. In one example the controller and memory 154 receive and analyze signals from the ECG sensing electrodes to determine if a treatable arrhythmia is present. Upon detection of the treatable arrhythmia the controller 154 can send a signal to the energy source 160 to charge the capacitors 156, 158 via the flexible circuit 144. After the capacitors 156, 158 have been charged to a sufficient level the controller 154 can instruct the capacitors 156, 158 to discharge the electrical energy through the flexible circuit 144 to the defibrillator electrode pads 140, 202. The housing 106 is illustrated with four housings 106a, 106b, 106c, and 106d containing the controller and memory 154, capacitors 156, 158, and energy source 160; however, alternate configurations can be used that use more or less housings to support the electronics such as the controller and memory 154, capacitors 156, 158, and energy source 160. For example, the electronics could be stored in a single housing, two separate housings, three separate housings, five separate housings, or six or more separate housings.

Figure 9A:
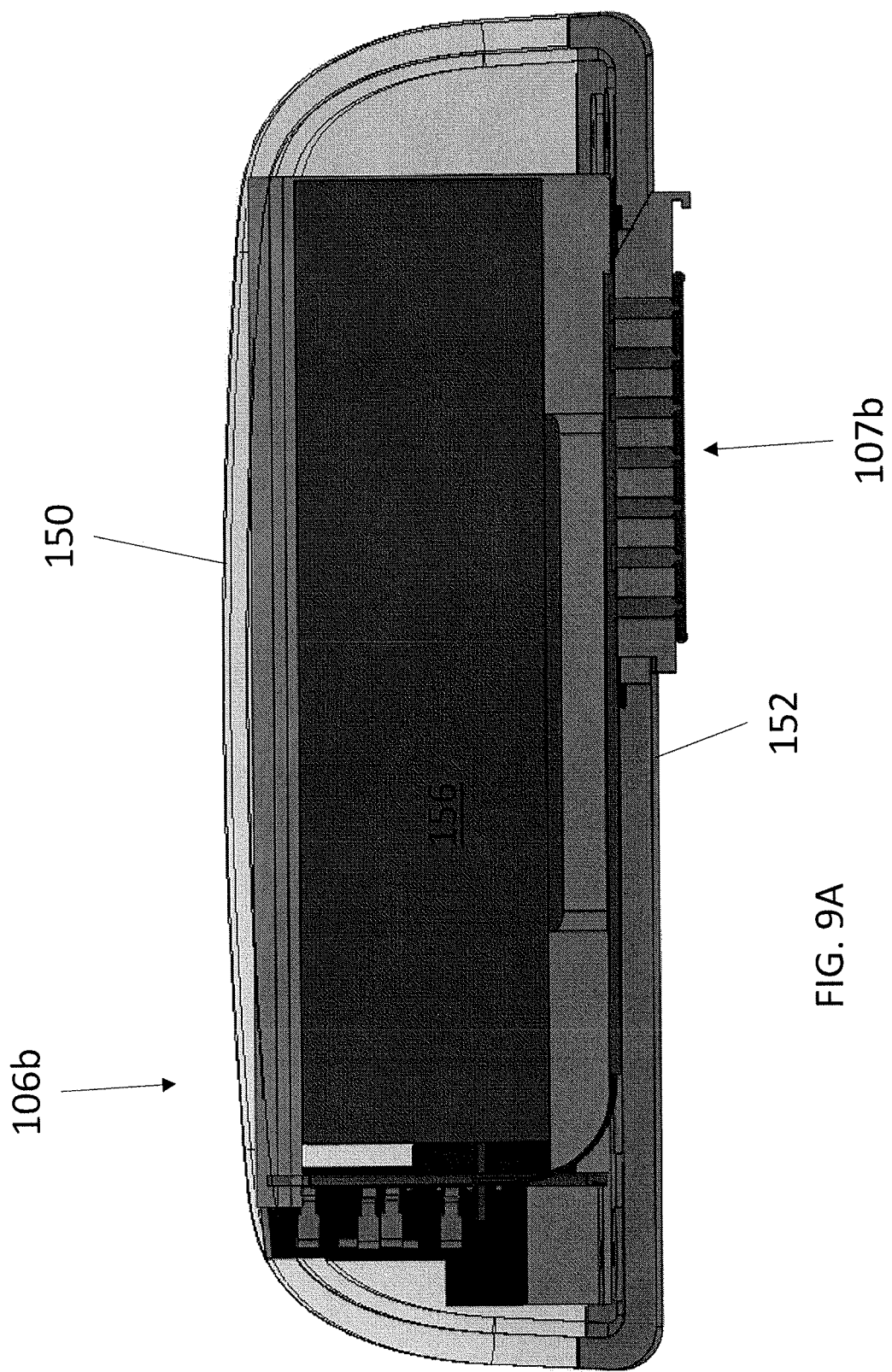
FIGS. 9A-9C illustrate a side view, bottom view, and cross-sectional view of a housing containing a capacitor in accordance with some embodiments.
Figure 9B:
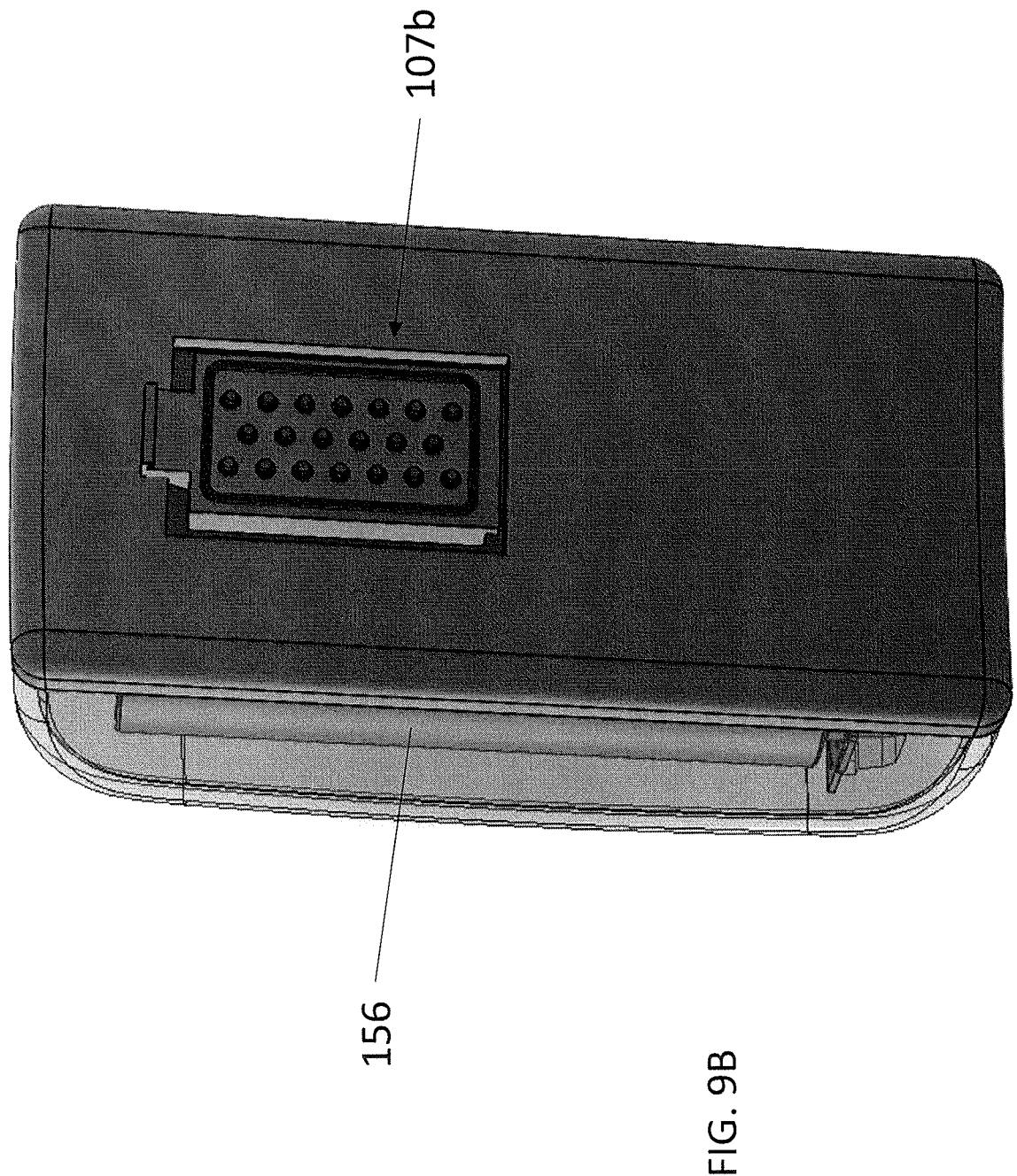
Figure 9C:
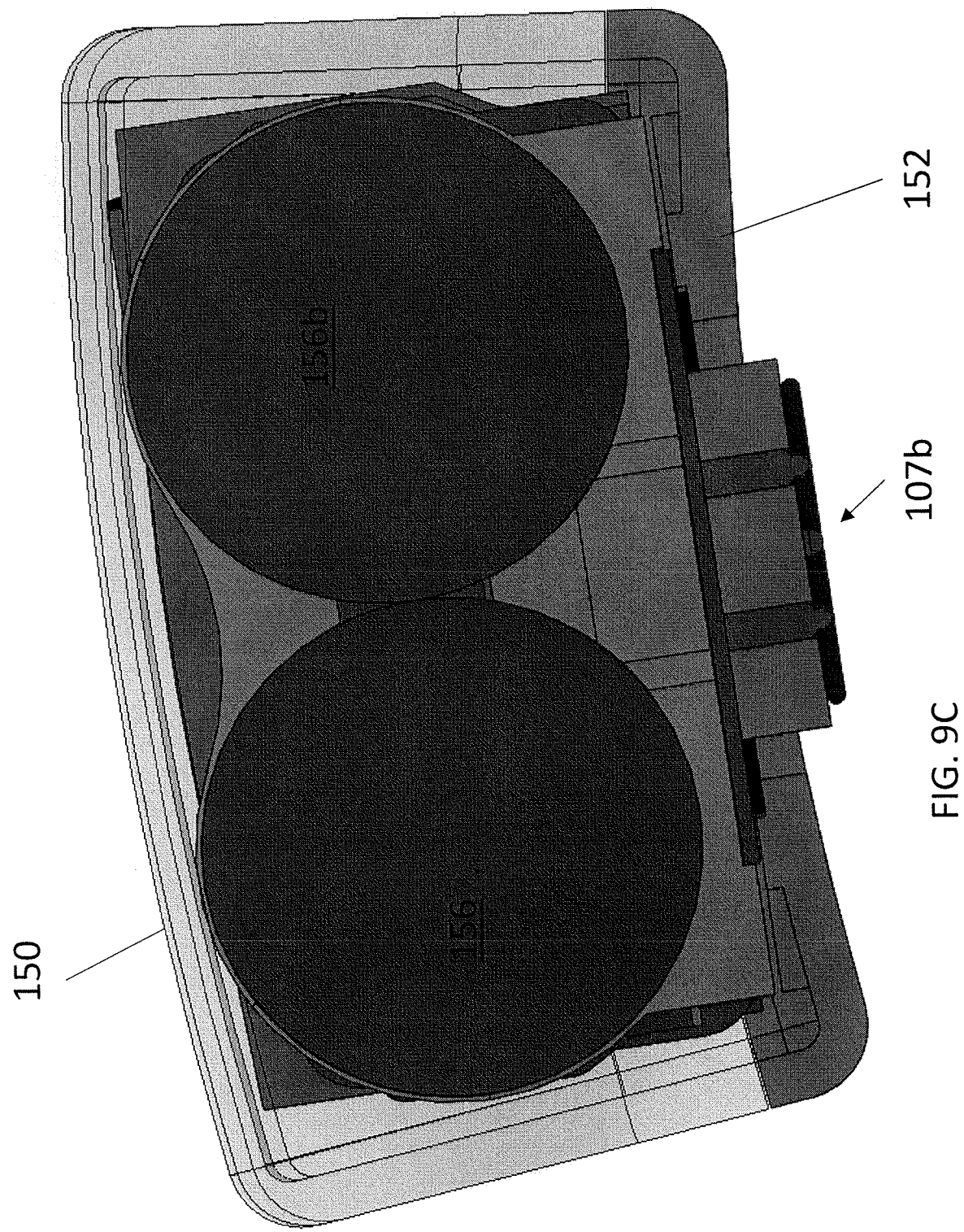

FIGS. 9A-9C illustrate a housing 106b containing a capacitor 156 in accordance with some embodiments. The housing 106b includes an upper shell 150 and lower shell 152 with capacitors 156 inside. The housing 106b includes electrical connection 107b. The illustrated electrical connection 107b can engage with a complementary structure on the flexible circuit 144, such as the connector 172 shown in FIG. 4. The illustrated capacitor configuration includes two capacitors 156, 156b. In some embodiments a single capacitors can be included within the housing 107b. In other embodiments multiple capacitors can be included the housing 107b.

Figure 10A:
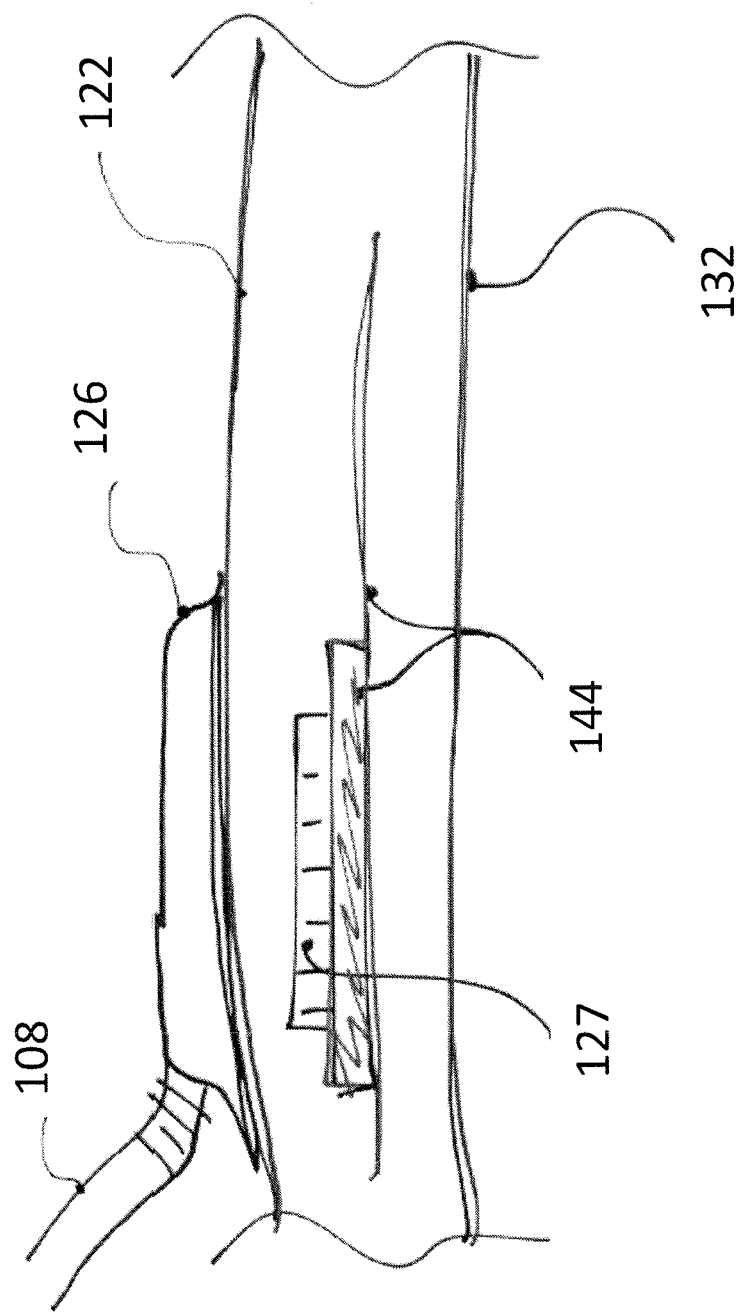
FIGS. 10A-10C illustrate electrical connections that can be used in embodiments of the wearable defibrillators described herein.

FIG. 10A is a schematic illustration of the electrical connection between the cable 108 and the patient engagement substrate. The flexible circuit 144 has a cable connection receptacle 127 engaged with or integral to the flexible circuit 144. The cable connection receptacle 127 has a complementary structure to receive the cable connection 126 of the cable 108. The cable 108 can electrically communicate with the flexible circuit 144 when the cable connection 126 is engaged with the cable connection receptacle 127.

Figure 10B:
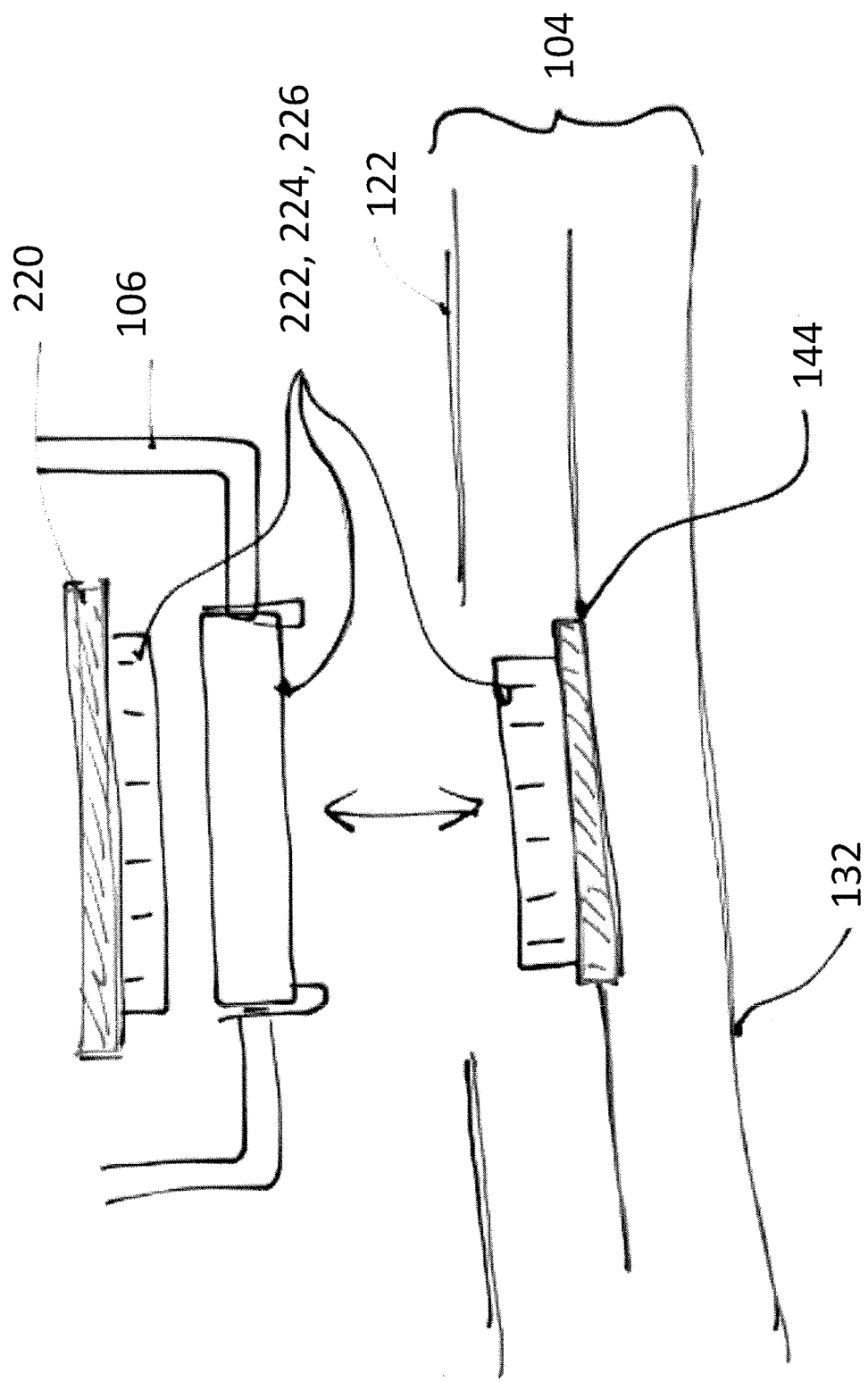

FIG. 10B illustrates a schematic example of an electrical connection between a circuit board 220 within the housing 106 and the lower patient engagement substrate 104 in accordance with some embodiments. The circuit board 220 can have a connector 222 that engages with an electrical connector 224 of the housing 106 that engages with an electrical connector 226 of the flexible circuit 144. The electrical connection formed between the electrical connector 224 and electrical connector 226 can be reversible or permanent. The configuration of the electrical connectors can vary based on the voltage, current, and number of desired electrical connections. For example, larger and more rugged electrical connections can be used between the housings containing the capacitors to facilitate providing the voltage and current associated with a therapeutic shock to the patient.

Figure 10C:
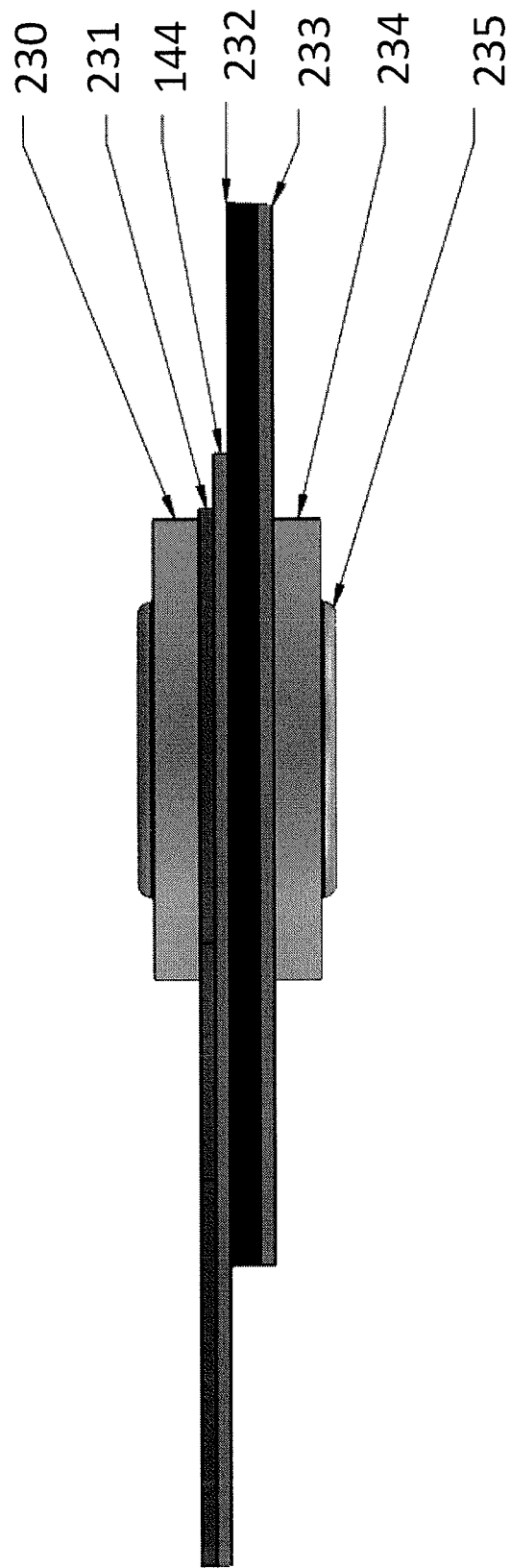

FIG. 10C illustrates an example of an electrical connection that can be made between the flexible circuit 144, and defibrillator electrodes 140/202 or ECG electrodes 146/198.

The electrical connection can include a conductive washer 230, exposed copper 231 on the flexible circuit 144, an electrode substrate 232, a silver base layer 233 of the defibrillator electrode 140/202, a conductive washer 234, and a conductive eyelet 235 contacting both washers 230/234. The conductive washer 230 is in direct electrical contact with the exposed copper 231 of the flexible circuit 144. The conductive washer 234 is in direct electrical contact with the silver base layer 233 of the defibrillator electrode 140/202. The conductive eyelet 235 forms a direct electrical contact between the conductive washers 230/234. The electrical connection illustrated in FIG. 10C can improve the current/voltage load between the capacitors 156/158 and the defibrillator electrodes 140/202.

Figure 11A:
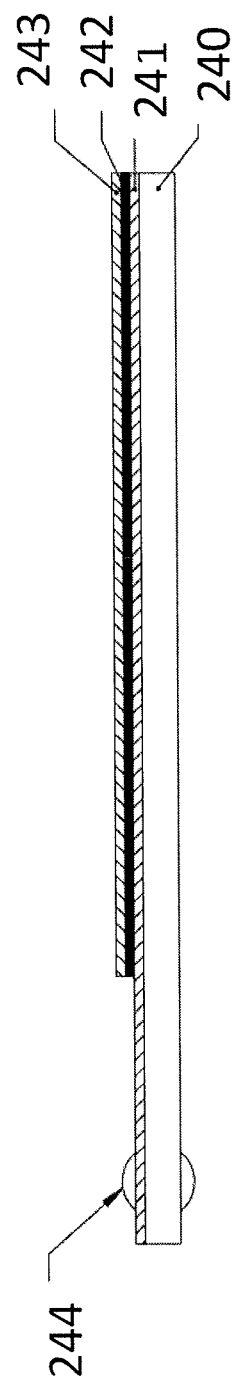
FIG. 11A-11B illustrate electrode configurations that can be used in embodiments of the wearable defibrillators described herein.
Figure 11B:
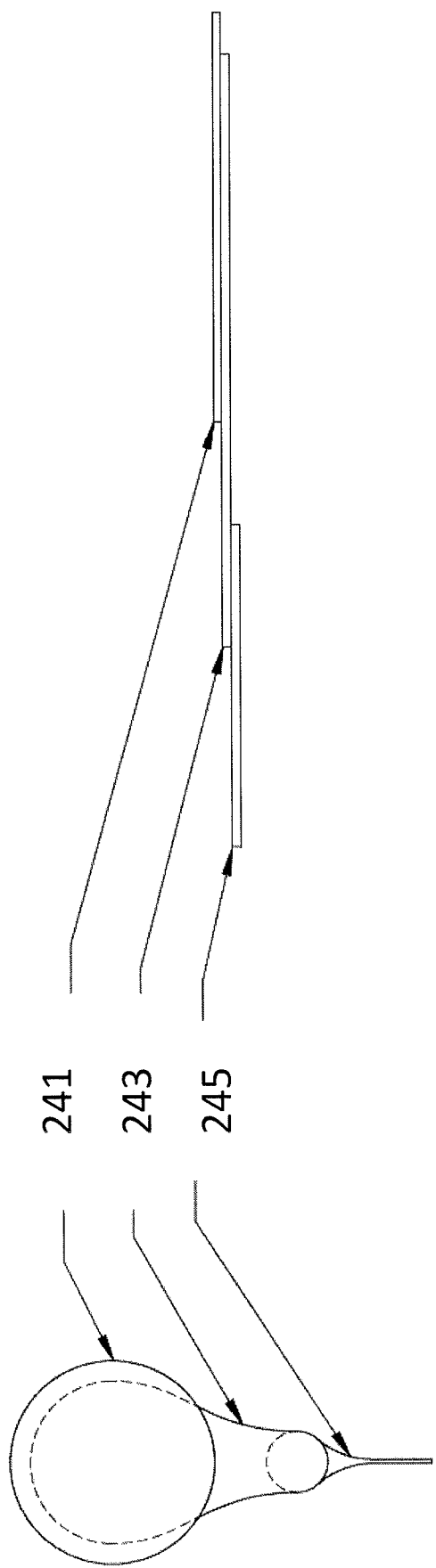

FIG. 11A-11B illustrate electrode configurations that can be used in embodiments of the wearable defibrillators described herein. FIG. 11A illustrates a portion of an electrode. The electrode can include a PET substrate 240, a silver base layer 241, carbon intermediate layer 242, and silver/silver chloride layer 243. The electrode construction can include an electrode termination to the silver base layer 244. FIG. 11B is a different view of a portion of an electrode construction. The electrode construction includes a silver base layer 241, silver/silver chloride layer 243, and copper flex line 245.

Figure 12:
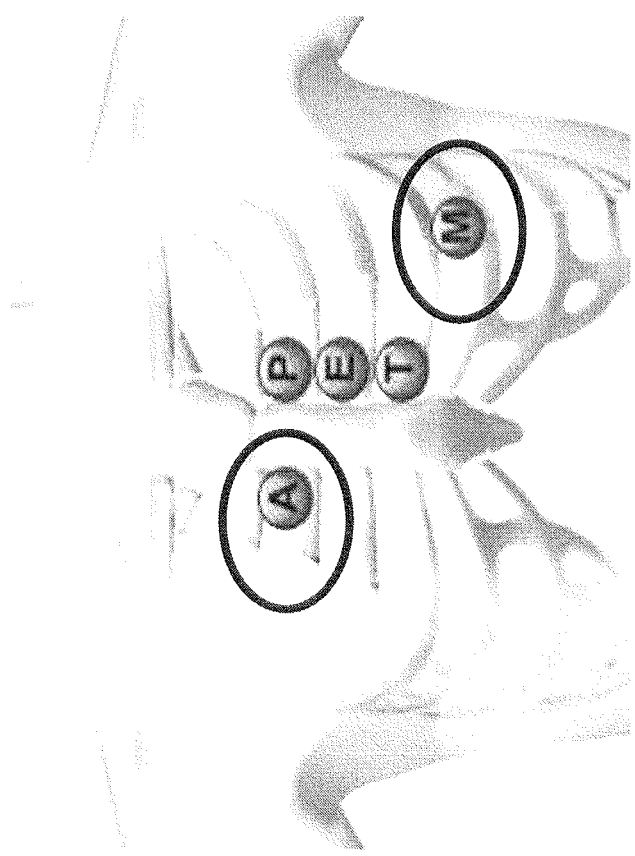
FIG. 12 illustrates an example of anatomical locations for sensing electrodes.

FIG. 12 illustrates an example of anatomical locations for sensing electrodes. The wearable defibrillators described herein can include sensing electrodes configured to contact the anatomical locations illustrated in FIG. 12.

Figure 13:
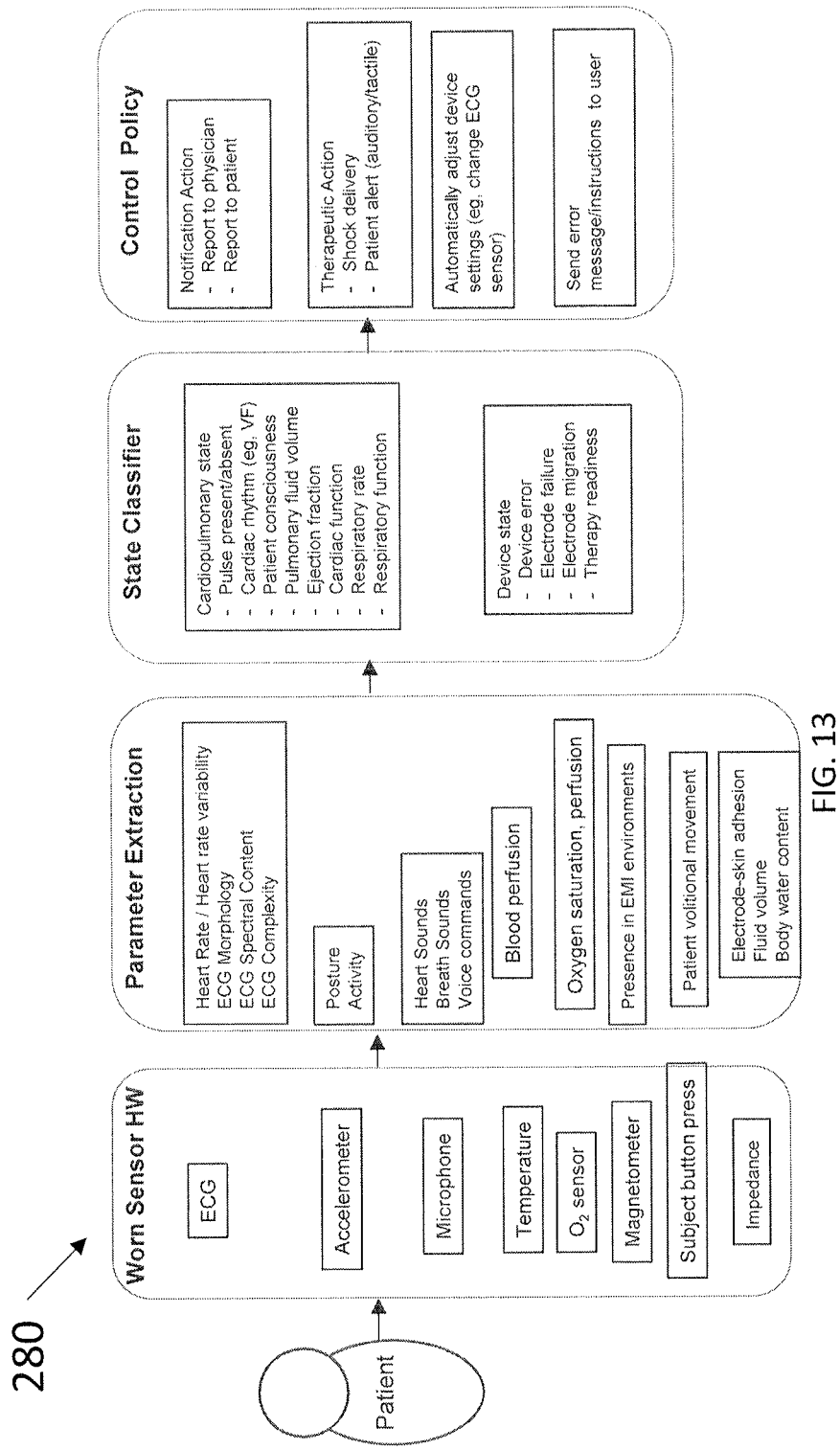
FIG. 13 illustrates a schematic flow chart for how the wearable defibrillators described herein can be used by the patient.

FIG. 13 illustrates a schematic flow chart 280 for how the wearable defibrillators described herein can be used by the patient. Sensors on the device, such as ECG, accelerometer, microphone, temperature, oxygen sensor like a pulse oximeter, magnetometer, impedance, and buttons can extract a plurality of patient parameters. Examples of the plurality of patient parameters include: heart rate, heart rate variability, ECG morphology, ECG spectral content, ECG complexity, posture, activity, heart sounds, breath sounds, voice commands, blood perfusion, oxygen saturation perfusion, presence in EMI environments, patient volitional movement, patient consciousness, fluid volume, body water content, and electrode skin adhesion. The controller can analyze the extracted parameters to determine if a treatment is necessary. Examples of state classifiers that can be determined by the device and controller include: cardiopulmonary state and device state. The determination of the cardiopulmonary state can include determination of: pulse present/absent, cardiac rhythm (e.g., VF), patient consciousness, pulmonary fluid volume, ejection fraction, cardiac function, respiratory rate, and respiratory function. Examples of the device state that can be determined include a device error, electrode failure, electrode migration, and therapy readiness. The controller can analyze the extracted parameters to determine if a notification action is necessary, such as a report to the physician or other healthcare provider or a report to a patient. The controller can further analyze the extracted parameters to determine if a therapeutic action is necessary, such as a shock delivery or patient alert (auditory, visual, tactile). Other examples of actions include adjusting the device settings, providing error messages, and sending instructions to the user. Adjusting the device settings can be done automatically, such as changing an ECG sensor.

FIG. 14 illustrates a method 300 of monitoring and defibrillating a patient's heart in accordance with some embodiments. The method 300 includes adhering to a first skin surface portion of the patient a first patient engagement substrate comprising a first plurality of sensing electrodes and a first defibrillator electrode pad, the first defibrillator electrode pad in electrical communication with an electrical energy source sufficient to provide a defibrillating shock, the first patient engagement substrate part of a wearable defibrillator comprising a fluid transport element configured to transport fluid away from the first skin surface portion of the patient to allow the wearable external defibrillator to be worn continuously 302; adhering to a second skin surface portion of the patient a second patient engagement substrate comprising a sensing electrode and a second defibrillator electrode pad, the second defibrillator electrode pad in electrical communication with the electrical energy source sufficient to provide the defibrillating shock, the second patient engagement substrate part of the wearable defibrillator, the wearable defibrillator including one or more sensors adapted to detect one or more of the pulse, oxygen content of the blood, impedance, galvanic skin impedance, temperature, breathing rate, heart sounds, and heart rate of the patient 304; measuring patient data corresponding to a cardiac signal of the patient with the first plurality of sensing electrodes, the sensing electrode of the second patient engagement substrate, and/or the sensors of the wearable defibrillator 306; and analyzing the patient data to determine if the patient has an arrhythmia 308.

The methods can further include upon detection of an arrhythmia detecting one or more of the pulse, oxygen content of the blood, impedance, galvanic skin impedance, temperature, breathing rate, heart sounds, and heart rate of the patient using one or more sensors on the wearable defibrillator and analyzing the detected one or more of the pulse, oxygen content of the blood, breathing rate, heart sounds, and heart rate of the patient to confirm the presence or absence of the arrhythmia. The methods described herein can include delivering an electrical shock after determining that the patient has an arrhythmia. The use of analyzing additional patient data in addition to the electrical data like the ECG of the patient can further confirm the absence or presence of a treatable arrhythmia. The increased confidence that the patient has a treatable arrhythmia prior to delivering a therapeutic shock reduces the likelihood of a false positive.

The methods described herein can include sensing impedance changes along a plurality of vectors of the patient with the one or more sensing electrodes of the first patient engagement substrate and the sensing electrode of the second patient engagement substrate and the first and second defibrillator electrode pads. A combination of the ECG sensing electrodes and signals recorded by the defibrillator electrode pads can be analyzed.

The impedance changes can be compared to a patient baseline and/or a database to measure a cardiac health of the patient.

The methods described herein can include measuring electrical data corresponding to a cardiac signal of the patient with the first plurality of sensing electrodes and the sensing electrode of the second patient engagement substrate.

Any of the sensors of the wearable defibrillator can be used to measure and analyze characteristics associated with the health of the patient. The methods described herein can include detecting one or more of the breathing rate, heart sounds, and heart rate of the patient with a microphone on the wearable defibrillator.

The methods described herein can include recording patient movement with an accelerometer integrated with the wearable defibrillator upon detection of an arrhythmia and analyzing the recorded patient movement to confirm the presence or absence of the arrhythmia. Utilizing additional data measured using the sensors on the wearable defibrillator can reduce the likelihood of a false positive determination of a treatable arrhythmia.

The methods described herein can include detecting the oxygen content of the blood with a pulse oximeter on the wearable defibrillator. Detecting the oxygen content of the blood with a pulse oximeter on the wearable defibrillator can include measuring the oxygen content of the blood of the patient at a point on a chest of the patient.

The methods described herein can include measuring a transthoracic impedance (TTI). The transthoracic impedance can be measured using any of the conductive parts of the wearable defibrillator, including the upper patient engagement ECG sensing electrode, the upper patient engagement defibrillator electrode pad, the lower patient engagement ECG electrodes, and the lower patient engagement defibrillator electrode pad. In some embodiments the transthoracic impedance can be measured between the first defibrillator electrode pad and the second defibrillator electrode pad. In some embodiments the transthoracic impedance can be measured simultaneously between multiple different sensing electrodes and defibrillator electrode pads.

The transthoracic impedance can provide information on the impedance of the body, the electrode-skin interface between the upper patch and the skin and the lower patch and the skin, and the electrode patch itself. The transthoracic impedance frequency can be used to measure specific impedances. The body can be modeled as mostly resistive. The electrode-skin interface can be modeled as a resistor and a capacitor in parallel. The electrode patch can be modeled as mostly resistive. At higher measurement frequencies, the resistance across the capacitive component of the electrode-skin interface can be minimized to get a clearer picture of the true body TTI. At lower frequencies, the capacitive component of the electrode-skin interface starts to dominate and you get a clearer picture of the TTI for the contact area of the electrode on the skin. A high-frequency TTI measurement (~32 kHz) can provide data about the power level to use for the therapeutic electrical shock. The lower frequency measurement (~8 kHz and lower) can provide information about how well the patch is contacting the skin, especially with continuous or periodic monitoring and analyzing for changes from a baseline value. The methods described herein can include monitoring both high and low frequencies while the device is worn by the patient. The measurements can be made at certain intervals over the duration that that the device is worn by the patient. The TTI measurements can provide data that can be used to determine the total energy delivery for the specific patient based on the TTI of their body. The TTI measurements can be used to provide information as to the quality of the engagement between the skin and the patient engagement substrates. For example, if part of the patch is peeling off and the defibrillator electrode pad is in partial contact with the skin then the electrical energy delivered to the defibrillator electrode pad can be increased such that a sufficient amount of electrical energy is provided to the patient. If the TTI is below a threshold value that indicates a high level of peel-off for the patient engagement substrate then an alarm can be provided to the user that the contact between the patient engagement substrate and skin needs to be improved. Peel-off or poor contact between the patient engagement substrate (e.g., poor contact between the defibrillator electrode pad and the skin) and the skin can result in a smaller surface area to provide the electrical energy to the skin, which can result in more energy lost to the skin and also an increased risk of skin burning.

The methods described herein can include measuring an impedance between two separate electrodes making up the first or second defibrillator electrode pad. The methods described herein can include analyzing the impedance between the two separate electrodes of the first defibrillator electrode pad to determine whether the two separate electrodes of the first defibrillator electrode pad are in sufficient electrical contact with the skin to deliver an electrical shock. The methods described herein can include measuring an impedance between the two separate electrodes of the second defibrillator electrode pad. The methods described herein can include analyzing the impedance between the two separate electrodes of the second defibrillator electrode pad to determine whether the two separate electrodes of the second defibrillator electrode pad are in sufficient electrical contact with the skin to deliver an electrical shock.

The methods described herein can include analyzing the measured electrical data corresponding to the cardiac signal of the patient for bradycardia, atrial fibrillation, asystole, heart blocks, pauses, ventricular tachycardia, ventricular fibrillation, tachycardia with aberrancy, or a supraventricular tachycardia (SVT).

The methods can include continuously wearing the wearable defibrillator for greater than about 24 hours. The methods can include continuously wearing the wearable defibrillator for greater than about 5 days. The methods can include continuously wearing the wearable defibrillator for greater than about 7 days. The methods can include continuously wearing the wearable defibrillator for greater than about 10 days. The methods can include continuously wearing the wearable defibrillator for greater than about 14 days.

The devices described herein can be used to monitor a patient for symptoms associated with heart failure or monitoring the cardiac health of the patient. In some embodiments the wearable defibrillators can be modified to be adapted to monitor a patient for heart failure and/or to determine a cardiac health of the patient. For example a single patient engagement substrate can be used in the heart failure monitoring device. The capacitors can be omitted in the heart failure monitoring device. The controller and energy source can be adapted to power and process the sensors used to detect the symptoms associated with heart failure. In some embodiments a wearable device for treating a patient to monitor for symptoms associated with heart failure are provided. The wearable devices can include a patient engagement substrate comprising an adhesive, one or more sensors, a first fluid transport element configured to transport fluid away from the skin to allow the wearable device to be worn continuously, and a first vapor permeable layer, the one or more sensors adapted to detect one or more of a pulse, a cardiac signal, oxygen content of the blood, impedance, galvanic skin impedance, temperature, breathing rate, heart sounds, and heart rate of the patient; and a controller configured to receive data collected by the one or more sensors and analyze the data to determine if the patient exhibits a symptom associated with heart failure.

The wearable device can be adapted to perform any of the heart failure monitoring methods described herein. The wearable devices can be configured to provide a stimulus to the patient upon detection of a symptom associated with heart failure. Examples of the stimulus include a vibration, an electrical shock, a visual alert, electronic notification, or auditory alarm. Any of the sensors described herein can be used with the device to detect the symptoms associated with heart failure in the patient wearing the device. Examples of the one or more sensors include one or more of: accelerometer, ECG sensing electrodes, pulse oximeter, microphone, magnetometer, impedance sensors, and galvanic skin impedance sensor. The controller can be configured to apply an algorithm to the data collected by the one or more sensors. The controller can be configured to apply an algorithm to the data collected by the one or more sensors. In some embodiments the algorithm adapts to the specific patient wearing the device. The controller can be adapted to modify the frequency of the sampling of the sensor data to efficiently receive and analyze the collected data. The controller can be adapted to selectively turn sensors on and off based on the relevant data collected with each sensor for the specific heart failure symptoms and the specific patient characteristics. The controller can be adapted to change the sensitivity of each of the sensors for the specific heart failure symptoms and the specific patient characteristics. The one or more sensors can be onboard the device or part of the patient engagement substrate or separate from the patient engagement substrate. For example, a wireless sensor can transmit data wirelessly to the device or a wired sensor can transmit data via a wired connection to the device. The wearable device can be adapted to transmit data wirelessly over a computer network to communicate with or provide information via a companion smart phone application.

Figure 15A:
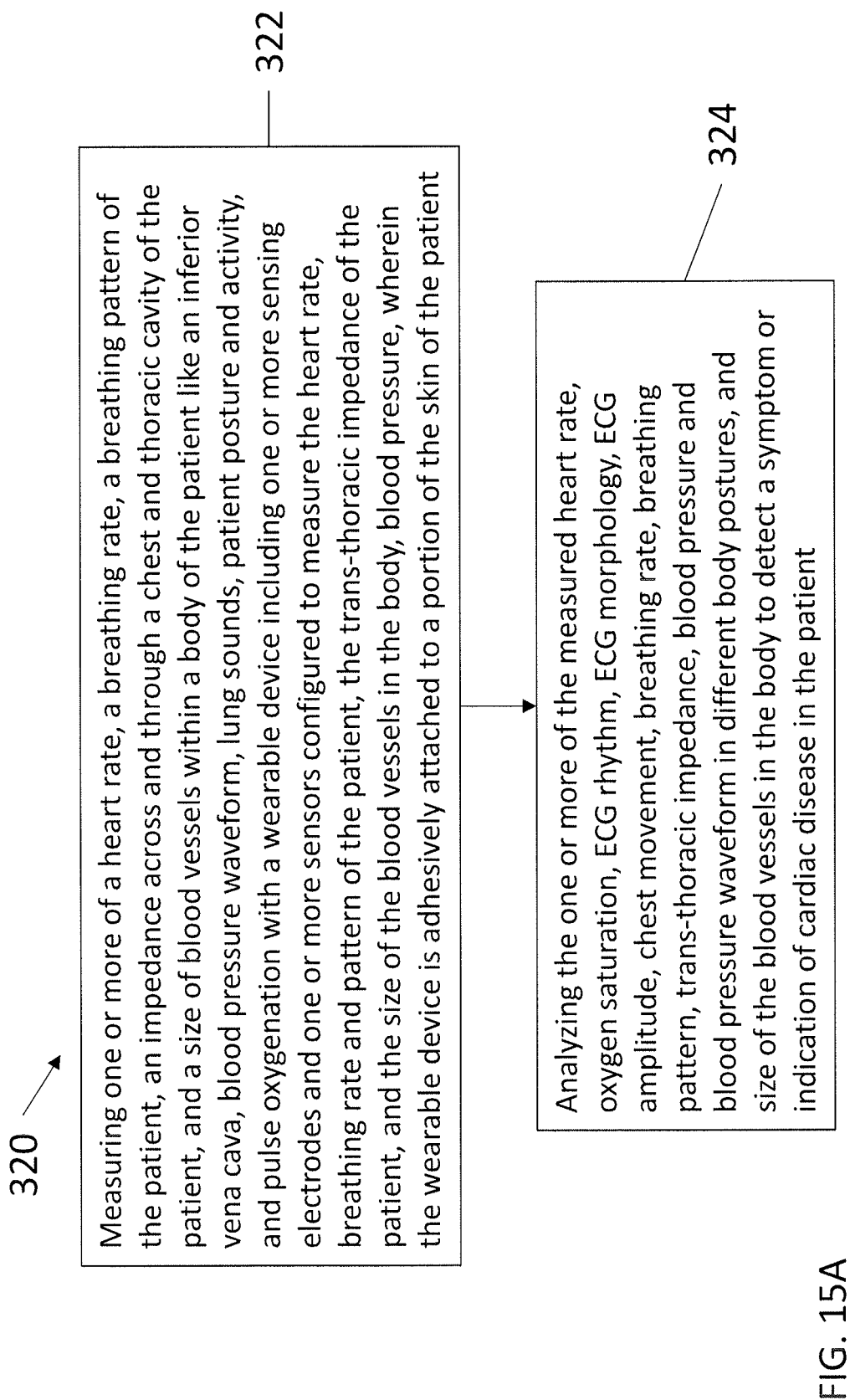
FIG. 15A is a flow chart of a method of monitoring a patient's heart to detect a symptom or indication of cardiac disease in the patient in accordance with some embodiments.
Figure 15B:
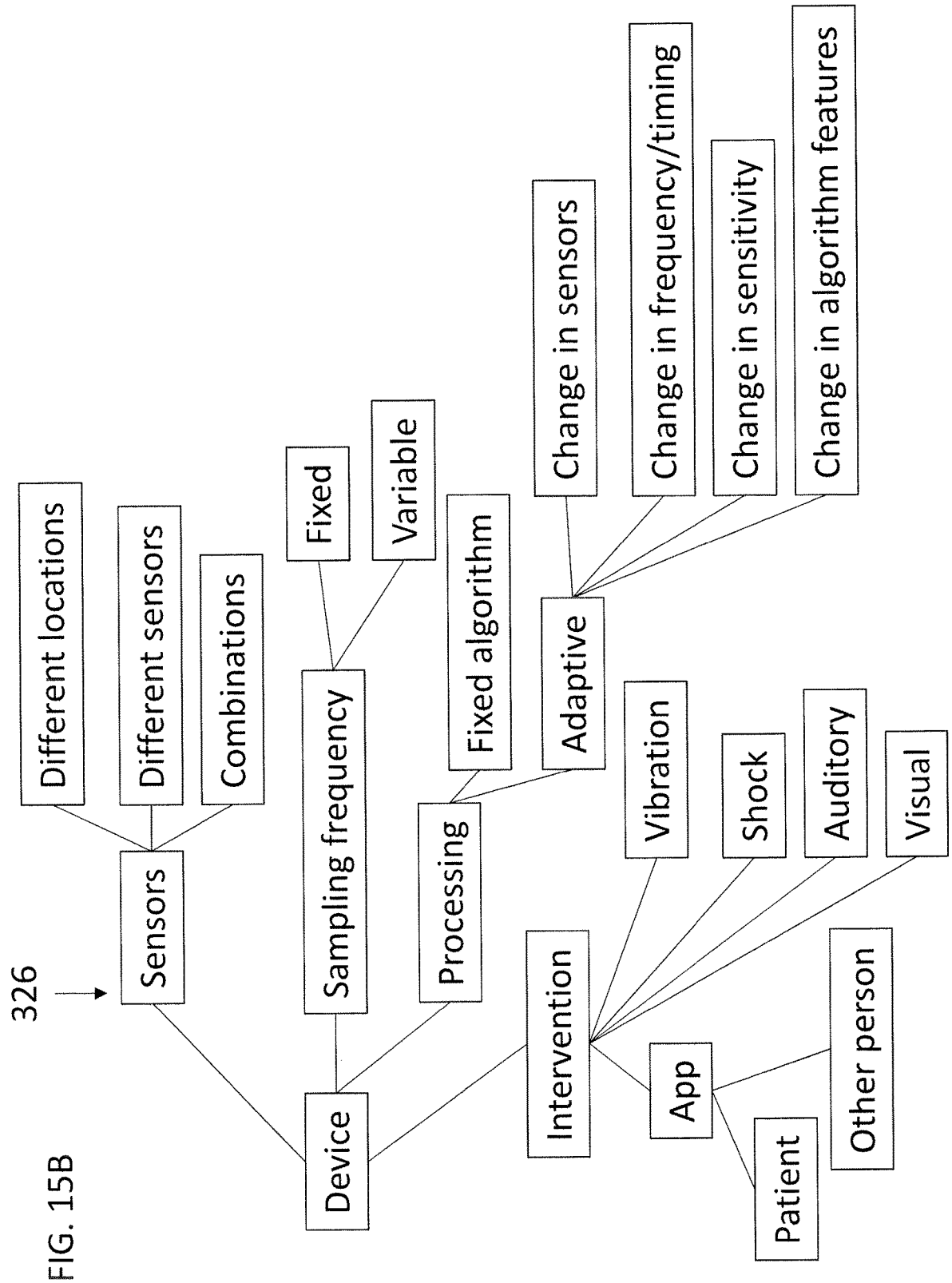
FIG. 15B illustrates a schematic flow chart of a method of detecting symptoms associated with heart failure in accordance with some embodiments.

FIG. 15B illustrates a schematic 326 of how the devices described herein can be used to detect symptoms associated with heart failure or to measure the cardiac health of the patient. The device can obtain data from the patient from sensors on board the device or in communication with the device. The sensors can be placed at different locations, can include different sensors, and a combination of different sensors. The device can modify the sampling frequency of any of the sensors. The sampling frequency can be fixed or can be variable. The device controller can process the collected data using a fixed algorithm or an adaptive algorithm. The adaptive algorithm can adapt to the specific patient using the device. The adaptive algorithm can analyze and make changes in the sensors, changes in the frequency/timing of the sampling, changes in the sensitivity of the sensors, and changes to the algorithm features. If the device detects a symptom associated with a cardiac health of the patient or other data of interest the device can provide an intervention to the patient. Examples of interventions include a vibration alert, a shock, an auditory alert, and a visual alert. Visual alerts can be provided through the device or as part of a hand held computer application like a smartphone application or tablet computer application. The alerts can be provided directly to the patient, a healthcare provider, family member, or other person based on the user preferences or severity of the detected medical issue.

FIG. 15A is a flow chart of a method 320 of monitoring a patient's heart to detect a symptom or indication of cardiac disease in the patient in accordance with some embodiments. The method 320 includes measuring one or more of a heart rate, a breathing rate, a breathing pattern of the patient, an impedance across and through a chest and thoracic cavity of the patient, and a size of blood vessels within a body of the patient like an inferior vena cava, blood pressure waveform, lung sounds, patient posture and activity, and pulse oxygenation with a wearable device including one or more sensing electrodes and one or more sensors configured to measure the heart rate, breathing rate and pattern of the patient, the trans-thoracic impedance of the patient, and the size of the blood vessels in the body, blood pressure, wherein the wearable device is adhesively attached to a portion of the skin of the patient 322; analyzing the one or more of the measured heart rate, oxygen saturation, ECG rhythm, ECG morphology, ECG amplitude, chest movement, breathing rate, breathing pattern, trans-thoracic impedance, blood pressure and blood pressure waveform in different body postures, and size of the blood vessels in the body to detect a symptom or indication of cardiac disease in the patient 324.

In some embodiments the methods include upon detection of the symptom or indication of heart failure in the patient, generating and providing a stimulus to the patient. Examples of the stimulus include one or more of: an electrical shock, a vibration, or an auditory alerts to the patient or physician.

The method can include upon detection of the symptom or indication of heart failure in the patient, saving a patient data to memory for later analysis or wirelessly transmitting the patient data to a computer for analysis.

The measurements being used to detect the symptom or indication of cardiac disease can include cardiac arrest and myocardial infarction. The measurements being used to detect the symptom or indication of cardiac disease can include heart failure, cardiomyopathies, heart blocks, atrial and ventricular arrhythmias.

Pulmonary edema can be determined using chest impedance by measuring multiple vectors across the chest from various ECG sensors and leads which allows assessment of fluid status in multiple different segments of the thoracic cavity.

The methods can further include analyzing the heart sounds measured by a microphone to determine the presence or absence of one or more of: rales or rhonchi, the presence of S3 and S4 heart sounds, and pathologies such as splitting in the S1 and S2 heart sounds.

The methods can also include analyzing the one or more of the measured parameters to determine a derived parameter for the patient for one or more of: ejection fraction, cyanosis, pulse quality, dyspnea, orthopnea, peripheral or pulmonary edema, right heart failure, left heart failure, nocturia, and cardiac arrhythmias, pulsus alternans, S3 cardiac sound, S4 cardiac sound, and splitting in S1 and S2 heart sounds. Examples of the derived parameters include pulmonary edema, ejection fraction, cyanosis, pulse quality, dyspnea, orthopnea, or nocturia. The ejection fraction can be determined using ultrasound and localized impedance changes to determine trending information of blood flow over time as a proxy for ejection fraction. Cyanosis can be determined using pulse oxygenation and impedance status to determine changes in blood oxygenation. Pulse quality can be determined using Doppler ultrasound delivered and measured by the wearable device together with closely spaced impedance sensors to determine changes in the shape of the pulse wave to indicate changes in cardiac function, including pulsus alternans. Dyspnea can be determined using a combination of accelerometer to determine patient posture and pulse oxygenation with impedance to determine the breathing pattern including accounting for recent activity of the patient to determine whether dyspnea is at rest. Dyspnea can be determined using a combination of accelerometer to determine patient posture and pulse oxygenation with impedance to determine the breathing pattern including accounting for recent activity of the patient to determine whether dyspnea is at rest. Orthopnea is determined using ultrasound to determine blood pressure together with accelerometer to determine patient posture can give an estimate of orthostasis. Nocturia can be determined using number of times the patient gets up during sleep as a proxy for nocturia.

Figure 16:
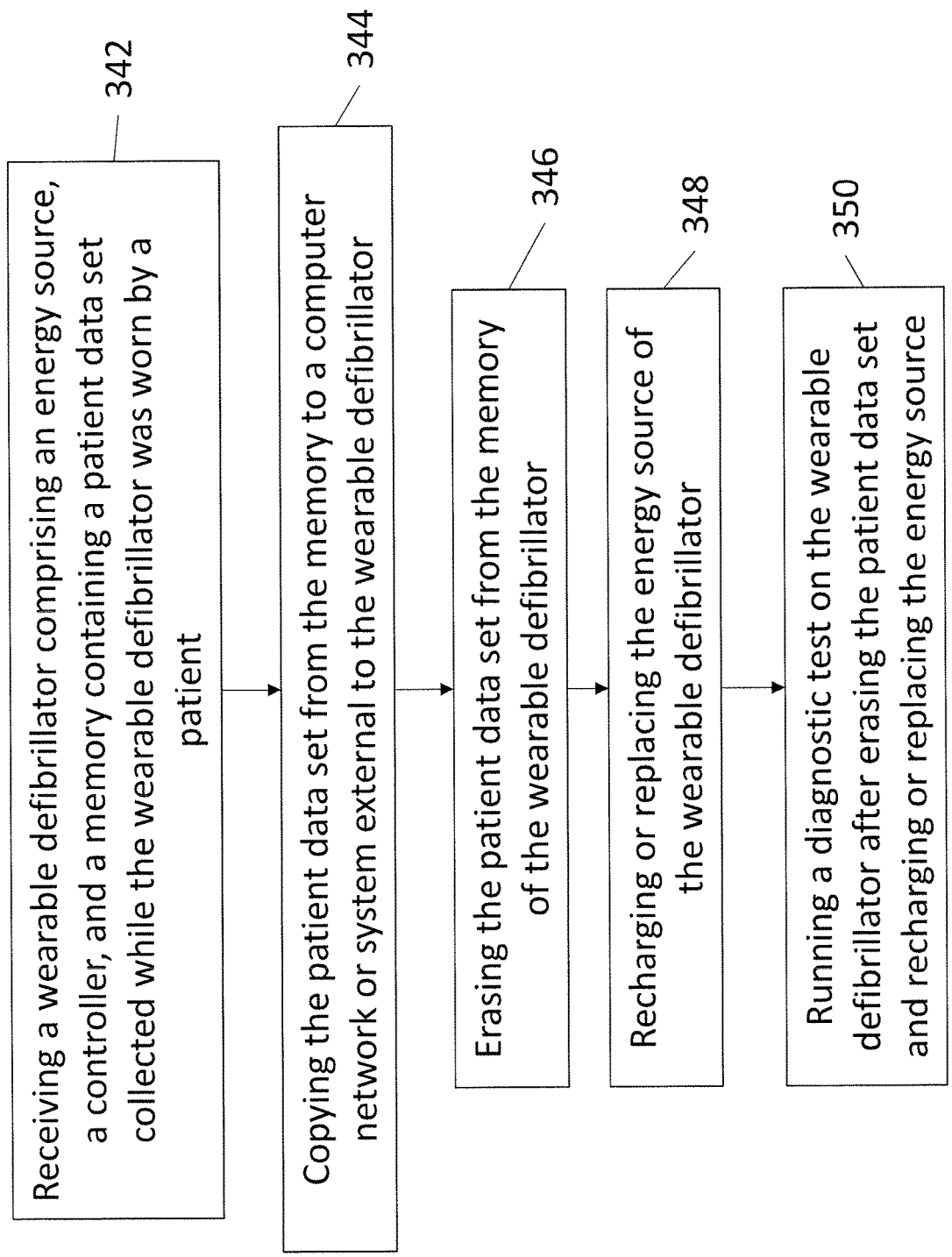
FIG. 16 is a flow chart of a method of refurbishing a wearable defibrillator in accordance with some embodiments.

FIG. 16 is a flow chart of a method 340 of refurbishing a wearable defibrillator in accordance with some embodiments. The wearable defibrillator that is refurbished can be any of the wearable defibrillators described herein. FIG. 16 shows a method 340 for refurbishing a wearable defibrillator that includes: receiving a wearable defibrillator comprising an energy source, a controller, and a memory containing a patient data set collected while the wearable defibrillator was worn by a patient 342; copying the patient data set from the memory to a computer network or system external to the wearable defibrillator 344; erasing the patient data set from the memory of the wearable defibrillator 346; recharging or replacing the energy source of the wearable defibrillator 348; and running a diagnostic test on the wearable defibrillator after erasing the patient data set and recharging or replacing the energy source 350. FIGS. 17-20 illustrates examples of refurbishing methods for the wearable defibrillators described herein. At a high level the refurbishment includes receiving data from the wearable defibrillator and refurbishing the electronics and any other expensive parts. Re-using the refurbished expensive components of the device can help lower the overall device cost. The more expensive device components typically include the electronics, such as the controller/processor, memory, capacitors, and energy source. The energy source can be replaced or recharged in the refurbished wearable defibrillator. After the electronics are refurbished the electronics can be used in a refurbished wearable defibrillator. New patient engagement substrates can be used in the refurbished wearable defibrillators.

In some embodiments the wearable defibrillator includes one or more modules containing the one or more capacitors, energy source, and controller. The refurbishment methods described herein can include replacing the energy source by replacing the module containing the energy source. Additional examples of refurbishment of the energy source include replacing the battery or recharging a rechargeable battery.

The diagnostic test can include testing the one or more capacitors, memory, energy source, and controller.

In some embodiments the refurbishment methods include refurbishing a wearable defibrillator that includes one or more housings containing one or more of the controller, memory, capacitors, and energy source. The controller and memory can be included in a first controller housing. The energy source can be included in a first energy source housing. The capacitors can be included in a first capacitor housing and a second capacitor housing. The refurbishment methods can include removing the controller and memory from the first controller housing. The refurbishment methods can include removing the energy source from the first energy source housing. The refurbishment methods can include removing the one or more capacitors from the first capacitor housing and the second capacitor housing. The diagnostic test can include testing the one or more capacitors, memory, energy source, and controller after removal from the one or more housings. After the electronics components have been removed from their respective housings they can be tested, refurbished, and placed in new housings.

The refurbishment methods can include engaging a data transfer cable with a connector in electrical communication with the memory. The refurbishment methods can include after running the diagnostic test, placing the controller and memory in a second controller housing. The refurbishment methods can include after running the diagnostic test, placing the one or more capacitors in a new first capacitor housing and a new second capacitor housing. The refurbishment methods can include after running the diagnostic test, placing the energy source in a second energy source housing. The refurbishment methods can include sealing the one or more housings to prevent water ingress. The refurbishment methods can include engaging the second controller housing, new first capacitor housing, new second capacitor housing, and second energy source housing with a patient engagement substrate to form a refurbished wearable defibrillator.

In some embodiments the wearable defibrillator can configured to support the one or more housings within a waterproof enclosure. The refurbishment methods can include removing the housing from the waterproof enclosure after receiving the wearable defibrillator. The refurbishment methods can include after running the diagnostic test, placing the housing within a second waterproof enclosure. The refurbishment methods can include engaging the housing with the second waterproof enclosure with a patient engagement substrate to form a refurbished wearable defibrillator.

The refurbishment methods can include engaging a data transfer cable with an exterior connection of the one or more housings. Copying can include a wired data connection to transfer the patient data set between the memory and the computer network or system. Copying can also include a wireless data transfer between the memory and a computer network or system.

The refurbished wearable defibrillator can be refurbished to include any of the wearable defibrillator configurations described herein. The refurbished one or more housings can be electrically connected to the flexible circuit, ECG sensing electrodes, and defibrillator electrode pads.

After refurbishment the refurbished wearable defibrillator can be packaged. After refurbishment the refurbished wearable defibrillator can be sent or provided to a second patient. The data collection and refurbishment steps described herein can be applied to the refurbished wearable defibrillator after it has been used by the second patient and returned. The methods can include receiving the refurbished wearable defibrillator containing a second patient data set collected while the refurbished wearable defibrillator was worn by the second patient. The methods can include copying the second patient data sent from the memory to a computer network or system external to the refurbished wearable defibrillator and erasing the patient data set from the memory of the refurbished wearable defibrillator. These steps can be repeated each time the wearable defibrillator or refurbished wearable defibrillator is returned after use by the patient.

The electronics components used in the wearable defibrillator can be refurbished multiple times. The one or more housings and associated electronics can be replaced or refurbished in the refurbished wearable defibrillator. In some embodiments the refurbishment methods include replacing or refurbishing the one or more housings and reusing the one or more capacitors five or more times. In some embodiments the refurbishment methods include replacing or refurbishing the one or more housings and reusing the one or more capacitors ten or more times. In some embodiments the refurbishment methods include replacing or refurbishing the one or more housings and reusing the one or more capacitors fifteen or more times. In some embodiments the refurbishment methods include replacing or refurbishing the one or more housings and reusing the one or more capacitors twenty or more times.

The patient data set can include data from the patient continuously wearing the wearable defibrillator for greater than about 24 hours. The patient data set includes data from the patient continuously wearing the wearable defibrillator for greater than about 5 days. The patient data set includes data from the patient continuously wearing the wearable defibrillator for greater than about 7 days. The patient data set includes data from the patient continuously wearing the wearable defibrillator for greater than about 10 days. The patient data set includes data from the patient continuously wearing the wearable defibrillator for greater than about 14 days.

The refurbishment process can vary based on the type of housings used to hold the electronics components. In some embodiments the electronics components can be removed from the housings and placed in new housings as part of the refurbishment process (see FIGS. 17A-17D). In some embodiments the housings including the electronics can be covered with the covers being replaced as part of the refurbishment process with the electronics components staying inside the housings.

Figure 17C:
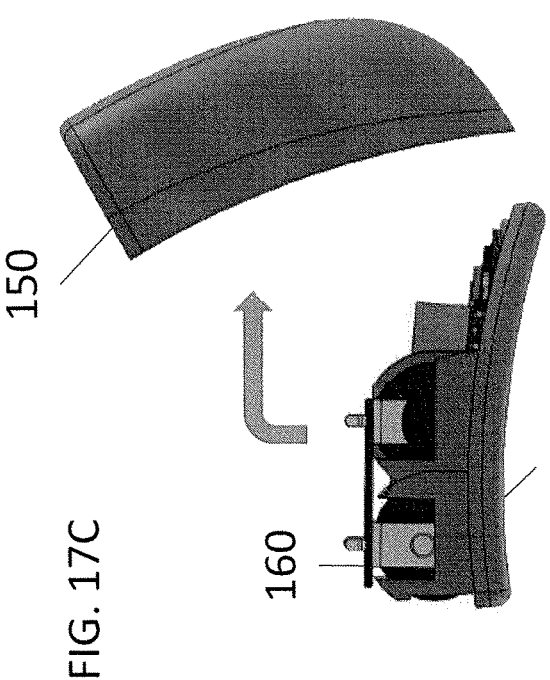
FIGS. 17-20 illustrates examples of refurbishing embodiments of the wearable defibrillators described herein.
Figure 17D:
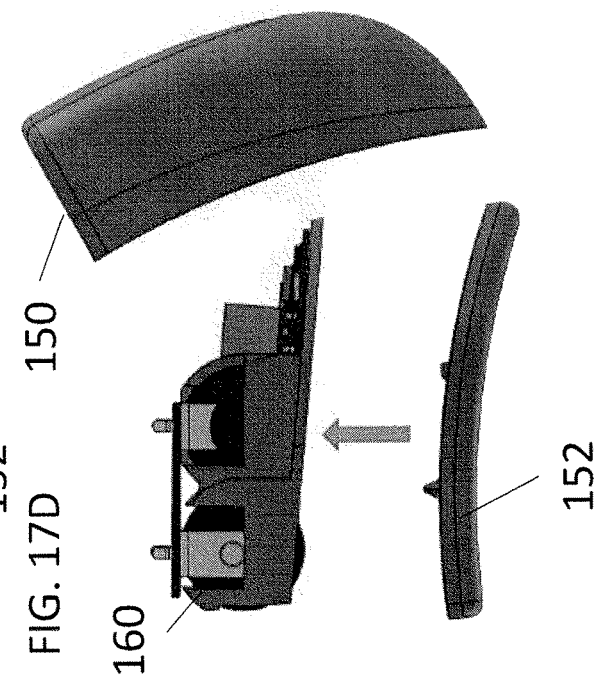
Figure 17A:
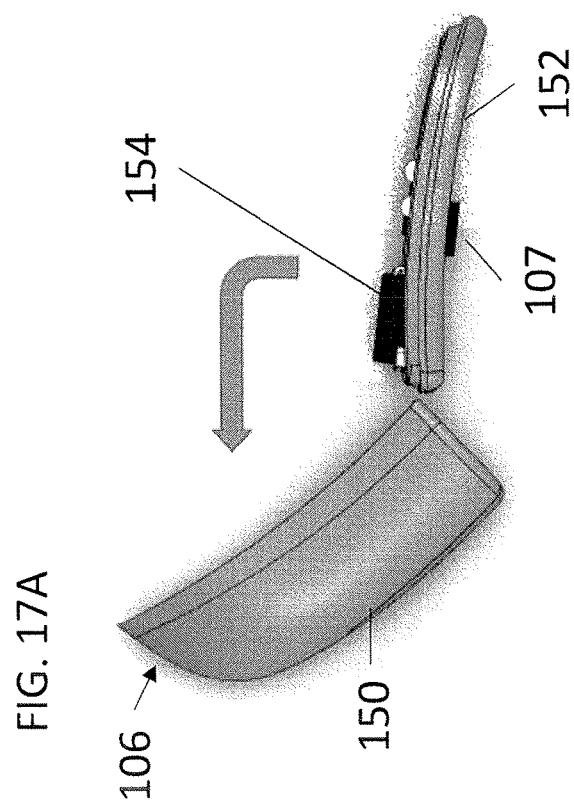
Figure 17B:
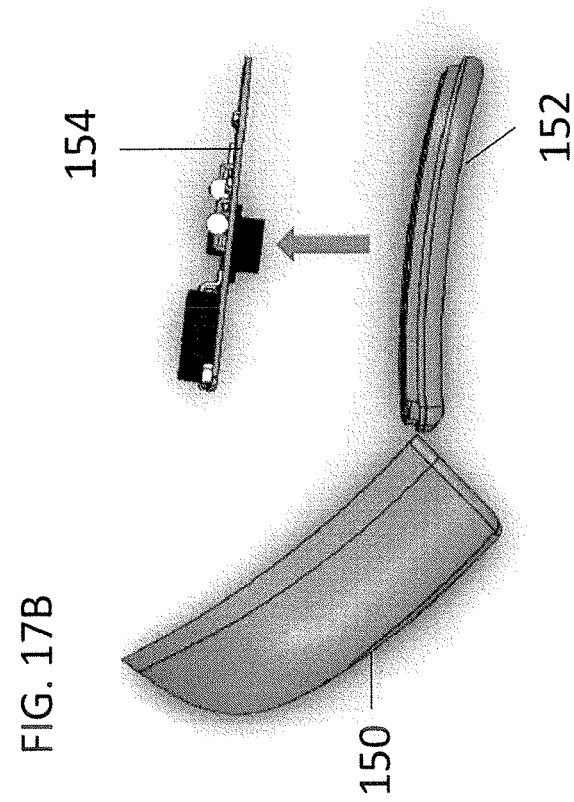

FIGS. 17A-17D illustrate an example of a part of a refurbishment process. FIGS. 17A-17B show the upper shell 150 being disconnected from the lower shell 152 to provide access to the processor and memory 154 within the housing 106. The processor and memory 156 can then be removed from the housing 106 for further refurbishment. After the processor and memory 156 is tested and refurbished it can be placed in a new housing 106 and be used in a refurbished wearable defibrillator. FIGS. 17C-17D show the removal of the energy source 160 from the housing 106 after separating the upper shell 150 from the lower shell 152. The energy source 160 can be recharged or a portion, such as the battery, can be replaced. After the energy source 160 has been refurbished it can be placed in a new housing 106 and used in a refurbished wearable defibrillator.

Figure 18:
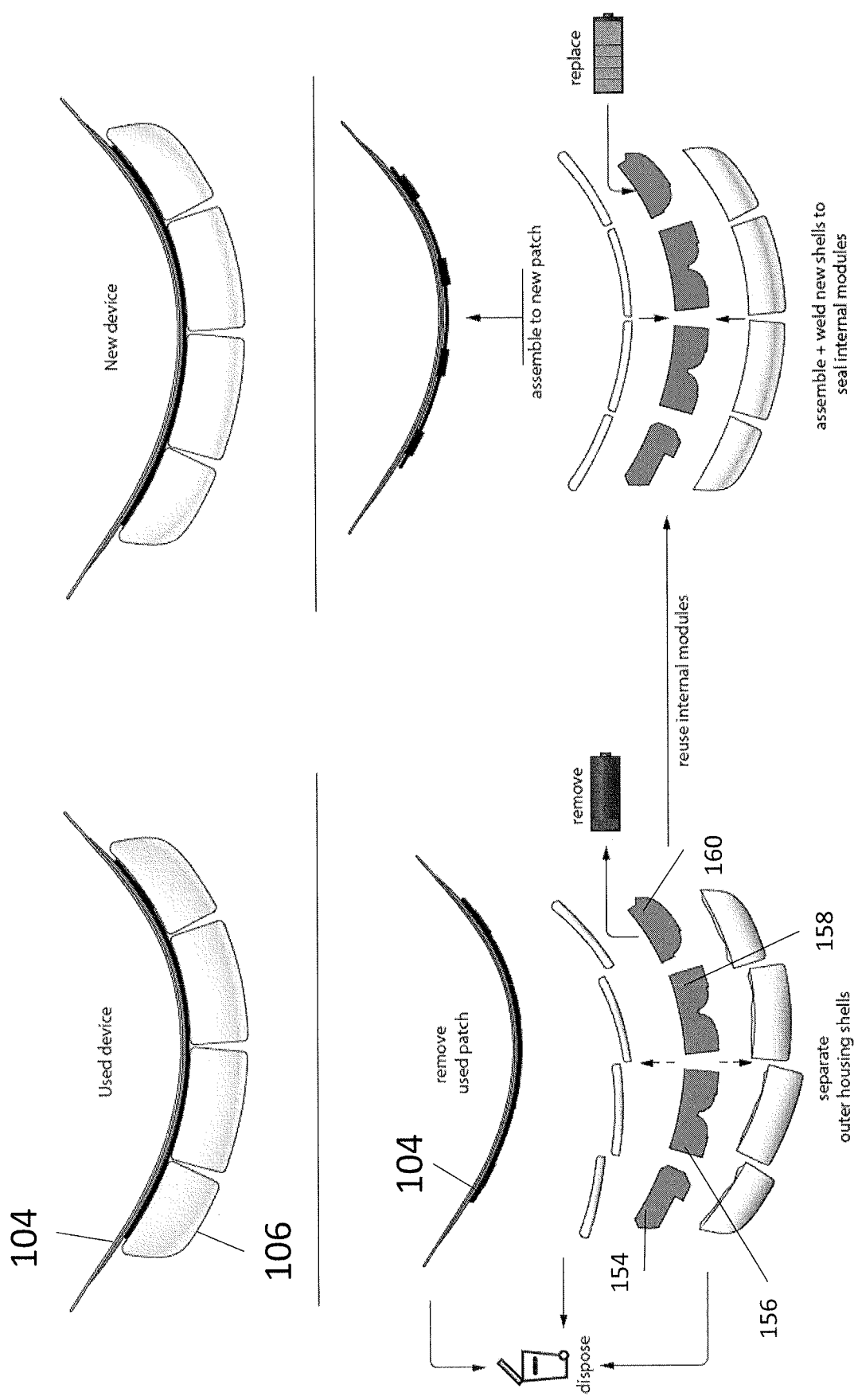

FIG. 18 illustrates a schematic showing the refurbishment of a used wearable defibrillator. The used wearable defibrillator is processed to separate the housings 106 from the patient engagement substrate 104. The removed patient engagement substrate 104 can be disposed of and is not typically reused. FIG. 18 shows the electronics components (processor and memory 156, capacitors 156, 158, and energy source 160) removed from outer shell housings. The outer shell housings can be placed in the trash. The electronics components can each be processed and refurbished. The energy source, such as the battery can be recharged or replaced. The capacitors, memory, and processor can be each tested to verify that they still meet the desired specifications prior to reusing them. FIG. 18 illustrates the discrete electronics components as being part of individual enclosures for simplicity. The refurbishment process can include removing the electronics components from any enclosures as shown in FIGS. 17A-17D. The refurbished electronics components can be placed in new outer shells and attached to a new patient engagement substrate. After refurbishment the new refurbished wearable defibrillator is ready for use.

Figure 19:
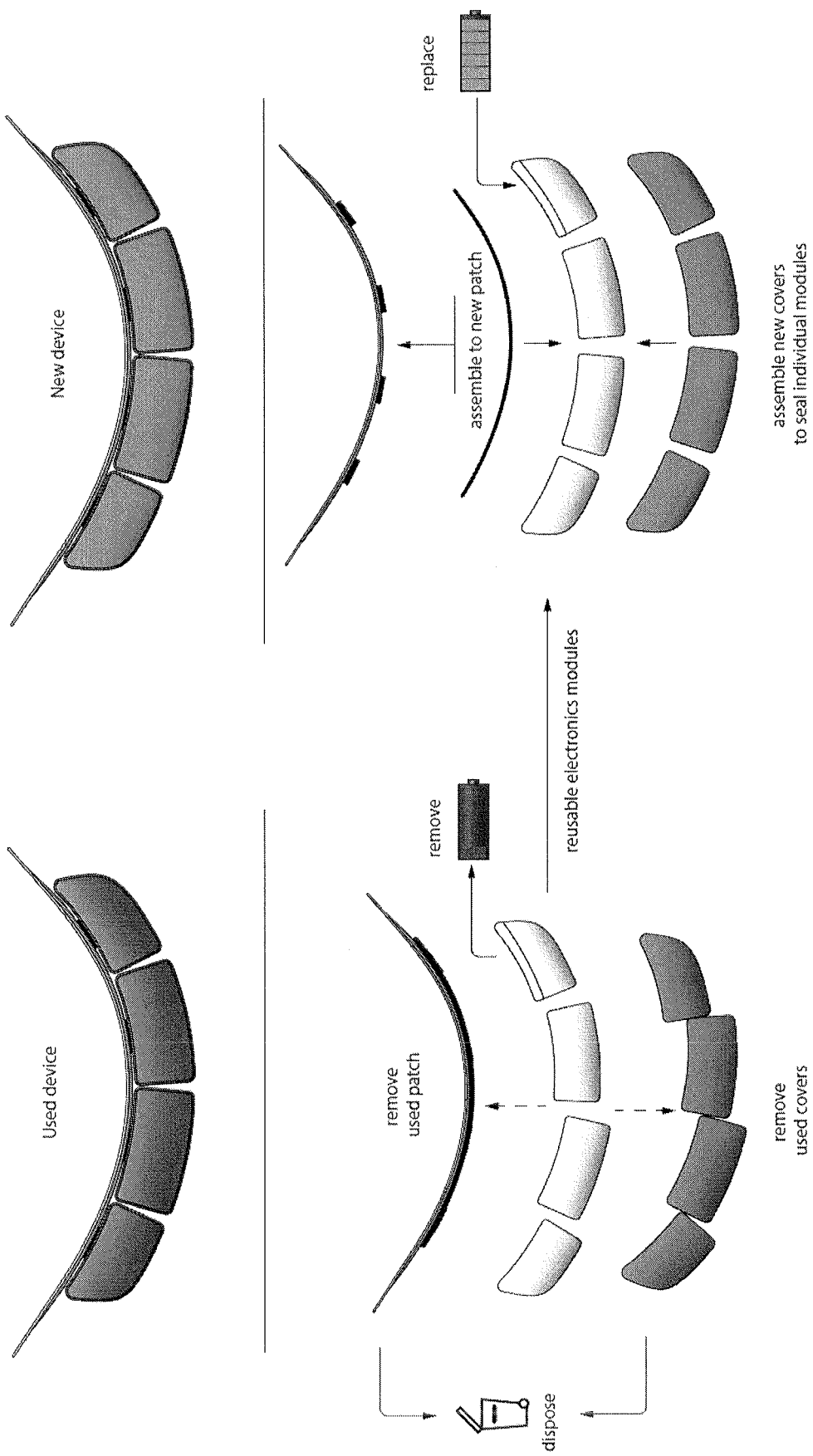
Figure 20:
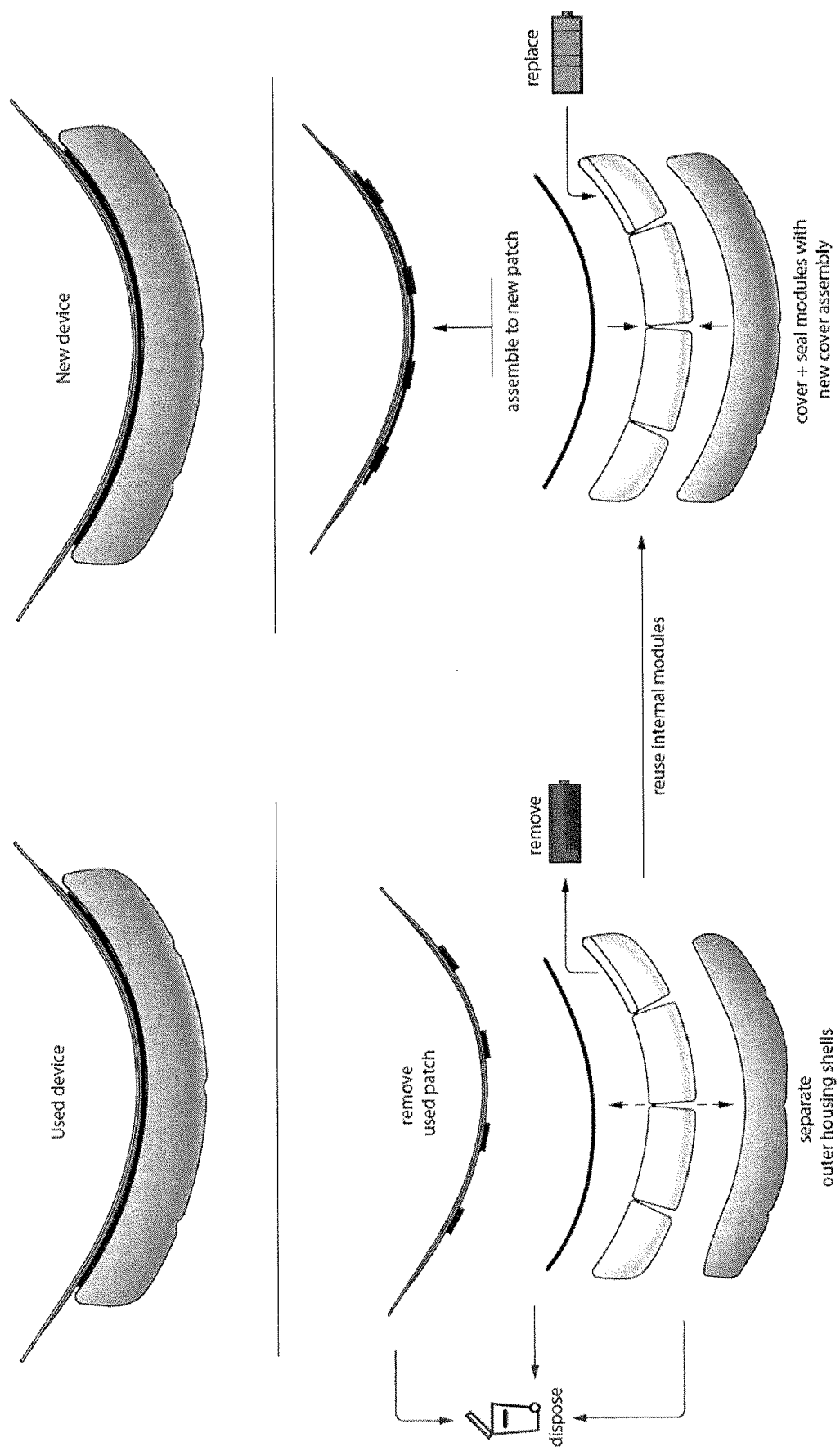

FIG. 19 shows a refurbishment process similar to FIG. 18 but with electronics components included in modules that are enclosed in removable covers. The electronics components in the modules are separated from the plurality of removable covers, refurbished, and the placed in new removable covers and engaged with a new patient engagement substrate. FIG. 20 shows a refurbishment process similar to FIG. 19 but with a removable cover that covers the electronics components instead of a multiple removable covers covering each of the electronics components.

Figure 21:
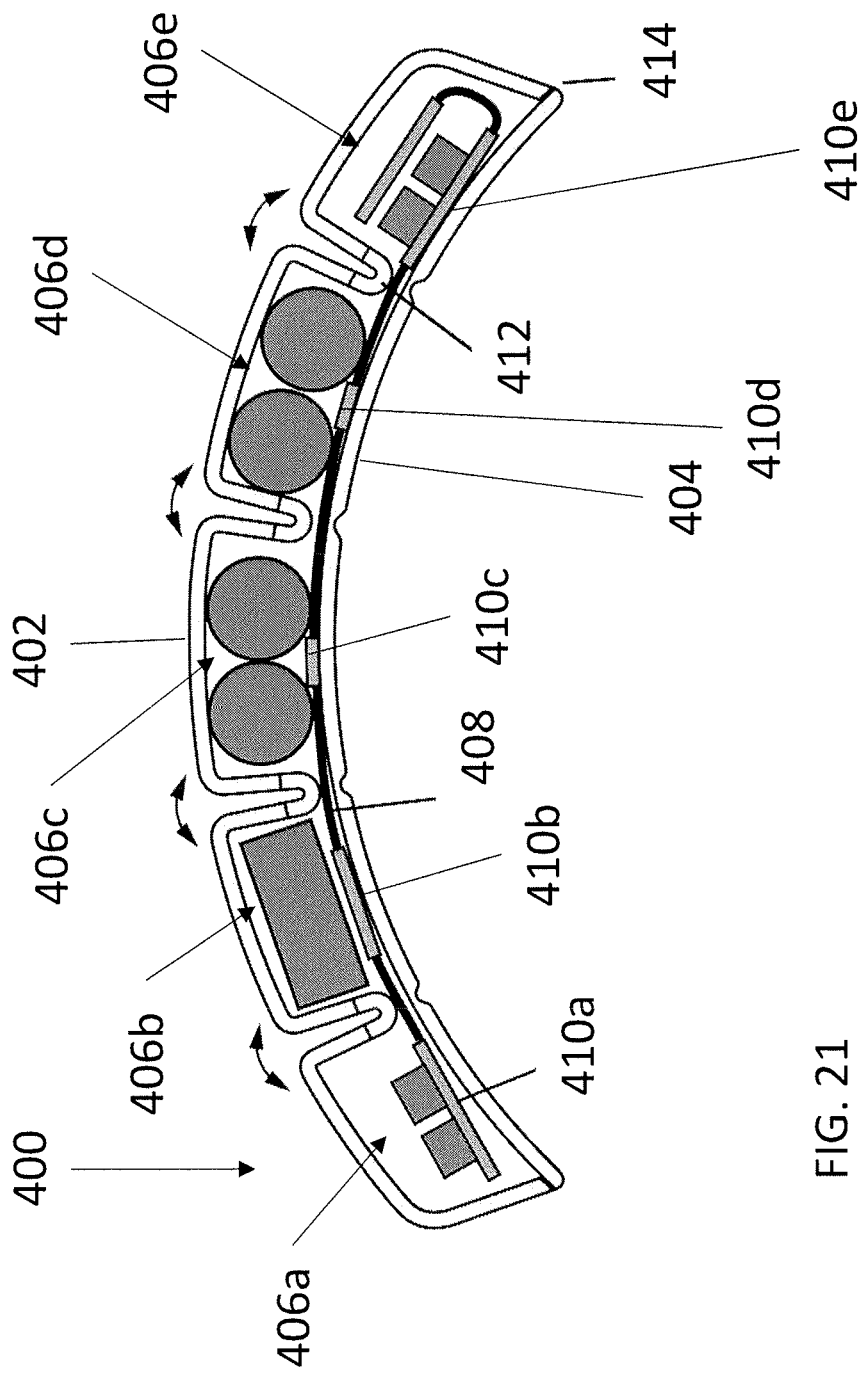
FIGS. 21-23 illustrate a cross-sectional view of embodiments of wearable defibrillators.
Figure 22:
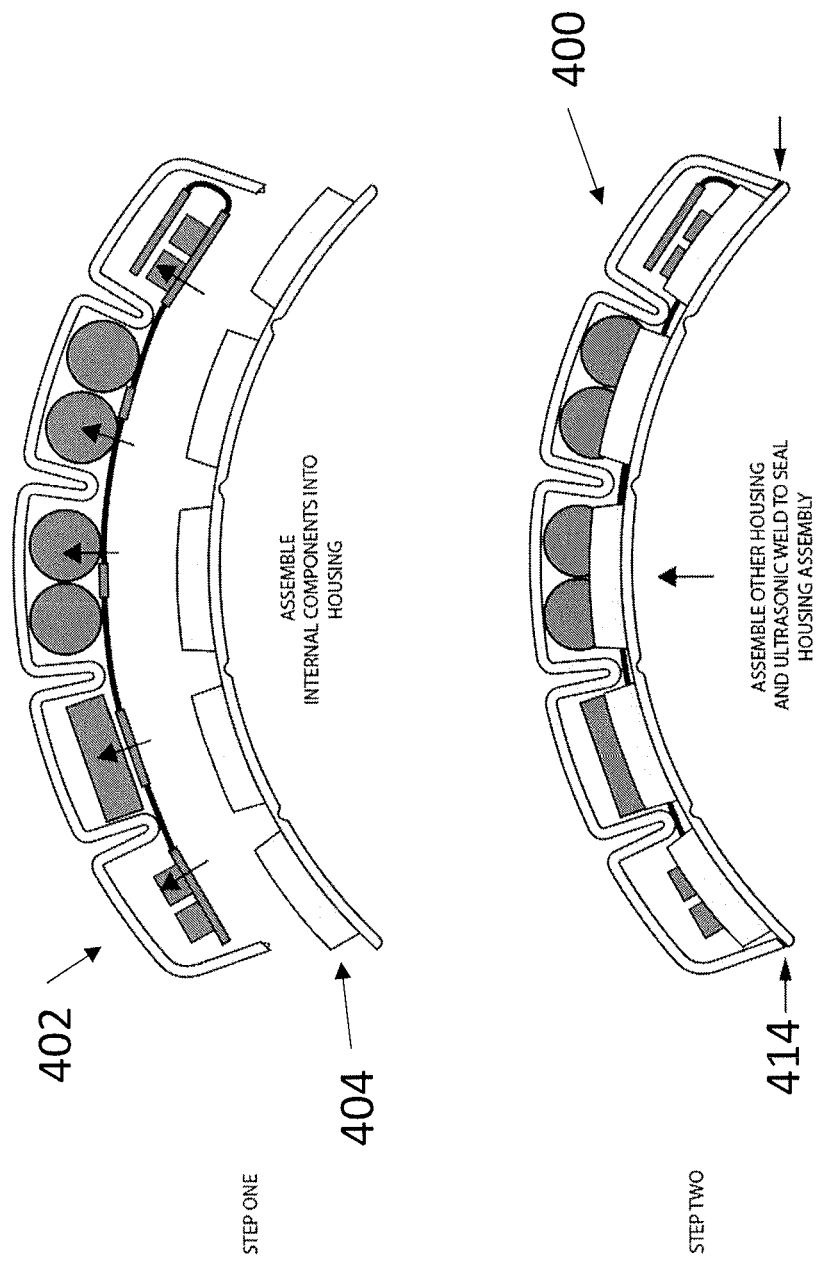
Figure 23:
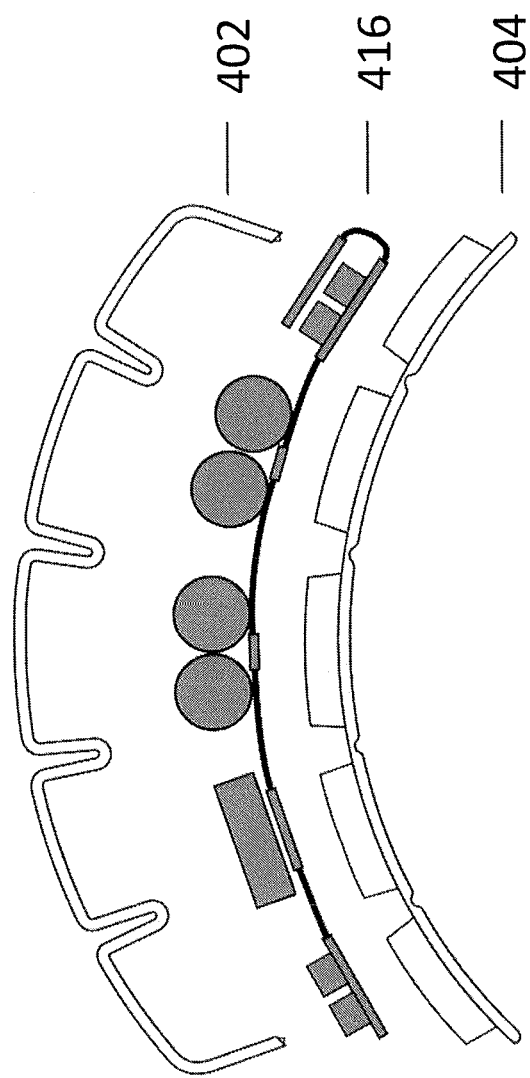

FIGS. 21-23 illustrate a cross-sectional view of portions of embodiments of wearable defibrillators. The illustrated housings 400 in FIGS. 21-23 include a flexible circuit within the housings in contrast to the wearable defibrillator 100 with the flexible circuit 144 within the patient engagement substrate 104. The housing 400 includes an upper shell 402 and lower shell 404 that define a plurality of enclosures containing the electronics components 406a-e. The electronics components 406a-e can be in electrical communication via a flexible circuit 408 containing printed circuit boards (PCBs) 410a-410e. The housing 400 can include a plurality of flexible joints 412. The upper shell 402 can form a seal 414 with the lower shell 404. FIG. 22 illustrates the use of ultrasonic welding to form the seal 414 between the upper shell 402 and the lower shell 404. FIG. 23 shows another view of the upper shell 402 separate from the lower shell 404 and the electronics section 416 defined by the electronics components 406a-e, flexible circuit 408, and PCBs 410a-410e. The wearable defibrillators illustrated in FIGS. 21-23 have a plurality of compartments with a flexible configuration that can bend to improve engagement with the wearer. The plurality of compartments can contain the electronics within the housing, such as the energy source, one or more capacitors, controllers, etc. The housing can contain a substrate with rigid printed circuit board (PCB) sections, flexible circuit sections, wires, and flexible housing joints.

Figure 24A:
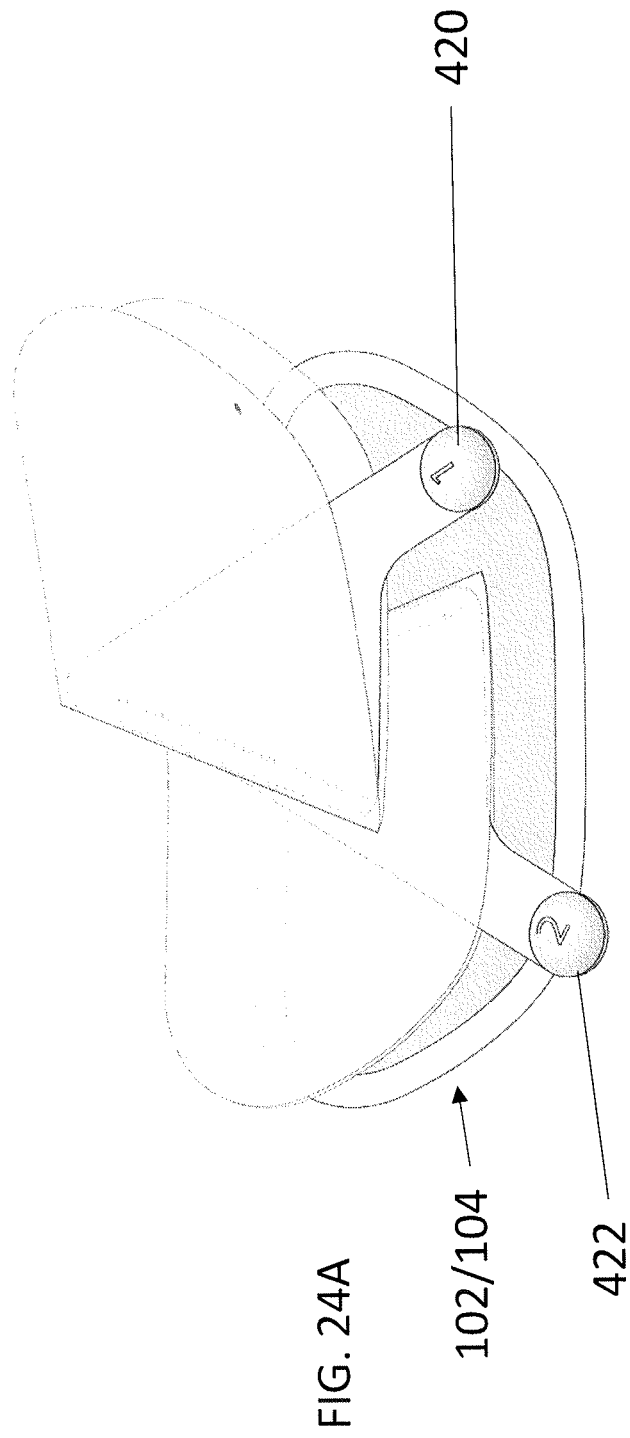
FIG. 24A-24B illustrate examples of release liners that can be used with the patient engagement substrates of the wearable defibrillators described herein.
Figure 24B:
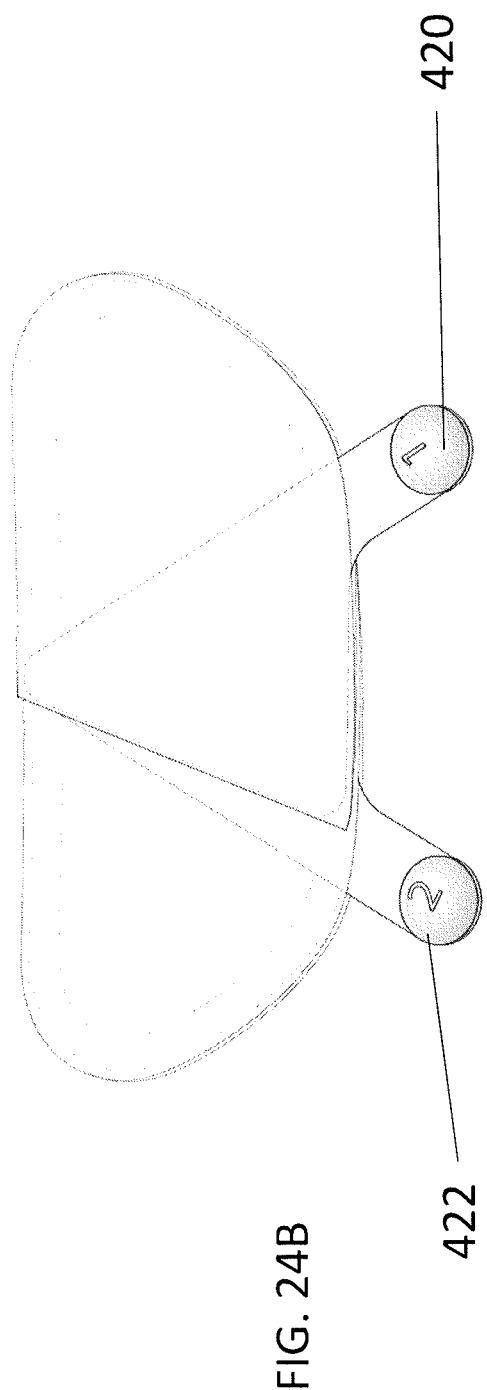

FIG. 24A-24B illustrate examples of release liners 420, 422 that can be used with the patient engagement substrates 102/104 of the wearable defibrillators described herein. The release liner 420, 422 can be used to cover the conductive gels and adhesives on the surface of the patient engagement substrate 102/104 prior to placing the wearable defibrillator on the patient. The release liners 420, 422 can be removed sequentially during the placement process to improve the process for correctly placing the patient engagement substrates and forming a good adhesion to the surface of the skin. The release liner 420 can be removed first followed by contacting the exposed adhesive and conductive gel with the skin of the patient followed by removing the release liner 422 and engaging the remaining portion of the adhesive and conductive gel with the skin of the patient.

Figure 25:
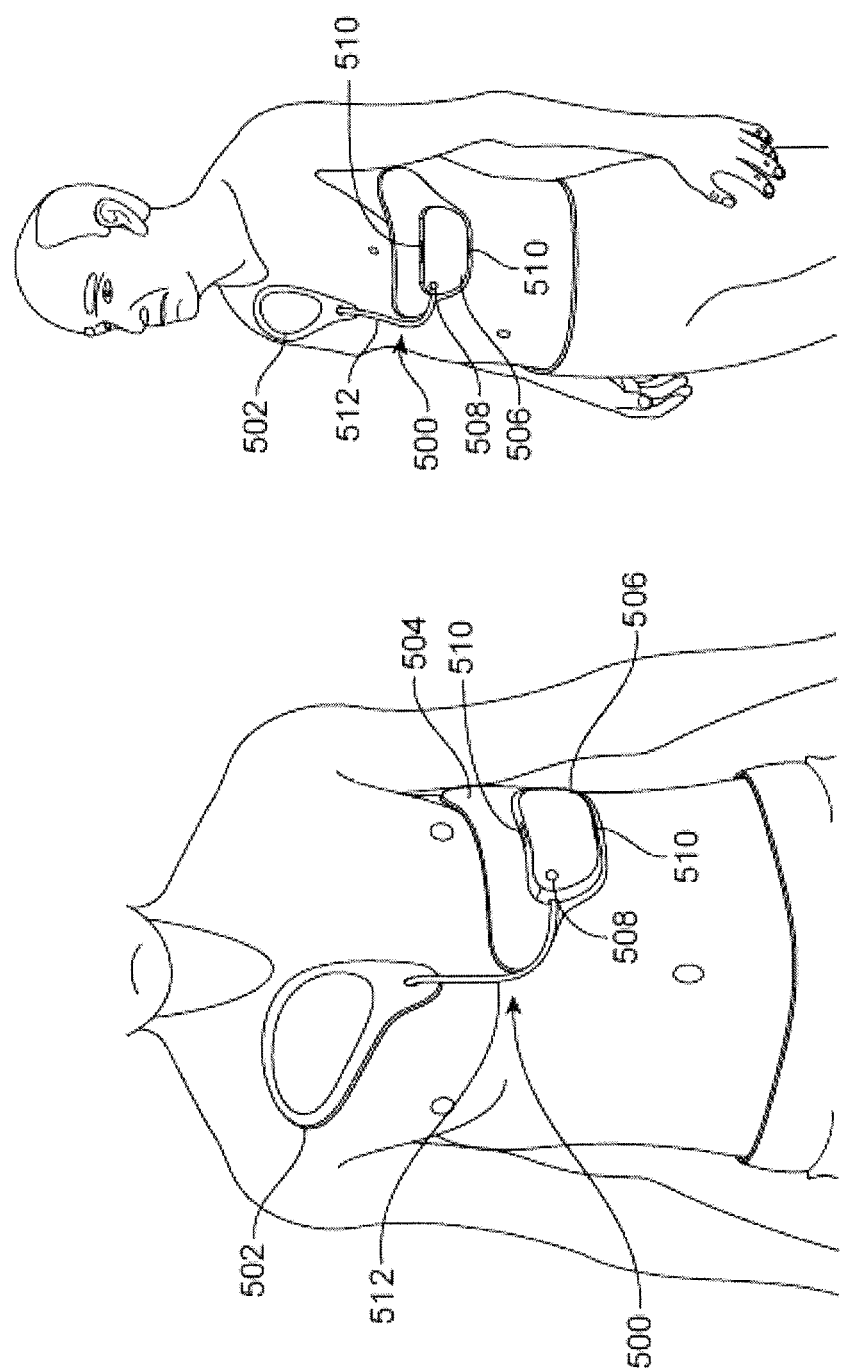
FIG. 25 is a wearable defibrillator in accordance with some embodiments.

FIG. 25 illustrates a wearable defibrillator 500 with an upper patch 502 having two sensor electrodes and a defibrillator electrode and a lower patch 504 having three sensor electrodes and a defibrillator electrode. The patient engagement substrate of the upper patch 502 and lower patch 504 includes the defibrillator electrode pads and the sensing electrodes. The lower patch 504 supports a housing 506 that includes a LED light indicator 508 to provide system feedback. The housing 506 includes buttons 510 that can be pushed by the user. The upper patch electrodes are connected to the electronics in the lower patch by conductive cabling 512. The lower patch 504 has a larger surface area than the upper patch 502 that can be used to spread the shear weight of the electronics module (e.g. battery, capacitors, and controller). The lower patch 504 is configured to follow the lower rib line of the wearer. The ECG sensors can be evenly spread across the vector. The housing 506 on the lower patch 504 includes user interface controls for easy access by the wearer. In some cases the upper patch 502 can include a feedback system, such as a speaker, for improved communication with wearers that have decreased hearing function. In some embodiments the upper patch can include an override button. In some embodiments the upper patch can include a speaker and override button. In other embodiments the speaker and/or override button can be on the lower patch. The illustrated cables 512 can included a cable management system to deploy or remove slack in the cable connecting the upper patch 502 and lower patch 504 to accommodate a spectrum of body sizes.

Figure 26:
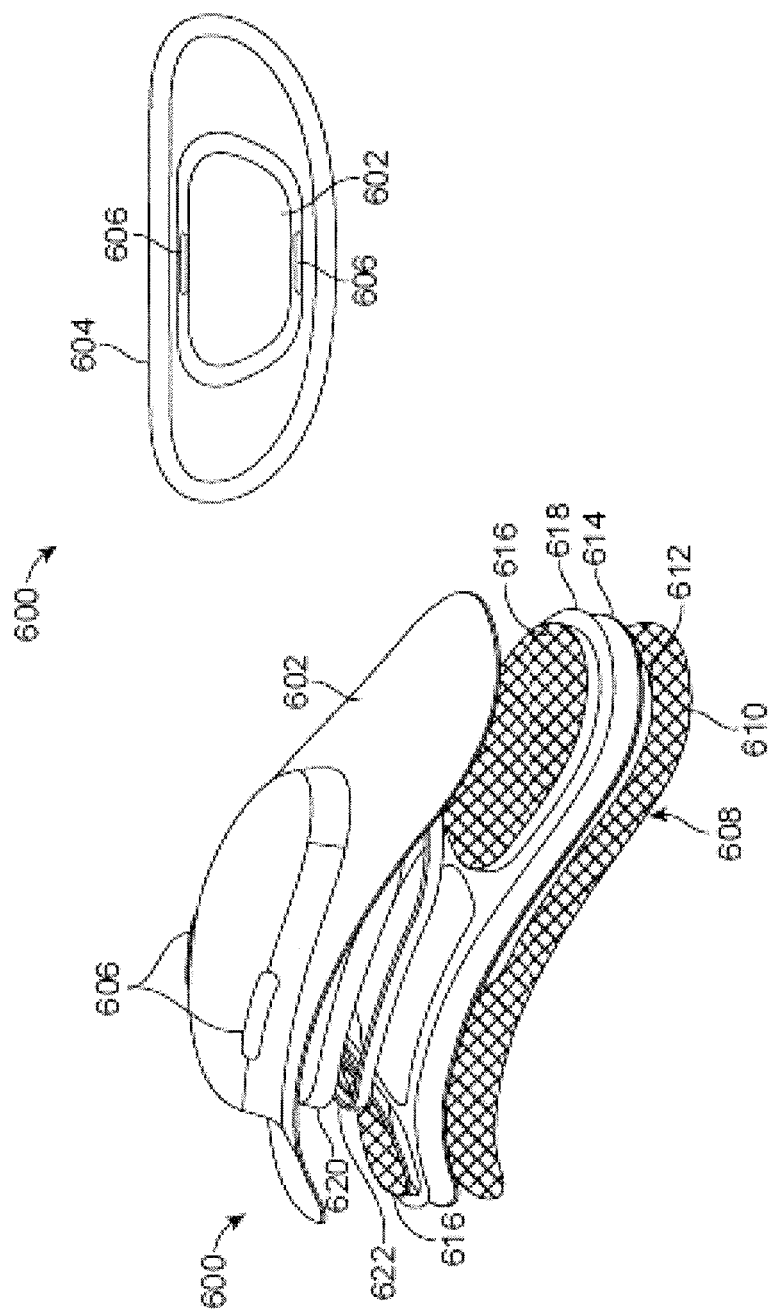
FIG. 26 is a portion of a wearable defibrillator in accordance with some embodiments.

The wearable defibrillators disclosed herein can have a multi-layer construction that can further improve the long term wearability of the defibrillator. FIG. 26 illustrates multiple views of a portion of a lower patch 600 of a wearable defibrillator 600 in accordance with some embodiments. A top view of the lower patch 600 shows the outer housing 602 and adhesive border 604. The housing 602 includes two buttons 606. The adhesive border 604 can be used to prevent moisture from entering the space between the skin and the electrodes and defibrillator electrode pad. Adhesive border 604 can also be used to prevent the device from being inadvertently peeled off due to mechanical abrasion across the edges of the device. The adhesive border can have a thickness of less than about 0.010 inches. In some embodiments the adhesive border has a thickness of about 0.001 inches to about 0.005 inches. The second view of the lower patch 600 is an isometric view illustrating the multi-layer construction of the lower patch 600. The lower patch 600 includes a layer 608 configured to contact the patient's skin for long term wear. The layer 608 that contacts the patient's skin includes adhesive 610, sensing electrodes, and a defibrillator electrode pad 612 configured to contact the skin for long term wear. The adhesive 610, sensing electrodes, and defibrillator electrode pad 612 can include complementary structures to fit together to form the layer or substrate that contacts the skin. In some embodiments the adhesive can be part of a fluid transport element. In some embodiments the adhesive can be modified to improve the fluid transport properties.

A wicking layer 614 can be in contact with the layer 608 containing one or more of the adhesive 610, hydrogel electrodes, sensor electrodes, and defibrillation pads 612. In some embodiments the wicking layer 614 is part of a fluid transport element. The wicking layer 614 can improve the diffusion of fluid, such as water liquid, vapor and moisture, from the skin across the layer (e.g. adhesive and electrodes) contacting the patient's skin. In addition to wicking fluid across the adhesive and electrodes the wicking layer can also diffuse fluids across a dominant surface area of the wicking layer. The wicking layer can have a flexible sheet-like structure that can conform to the desired surface morphology for the device and skin of the patient. The flexible sheet-like structure has a dominant surface area that is the surface area of the flat sheet surface of the layer. The dominant surface area can be either the side of the layer closer to the patient engagement/skin side of the layer or the side of the layer closer to the external housing side of the layer. Spreading the fluid out across the dominant surface area of the wicking layer can greatly improve the fluid transport properties of the device by spreading the fluid out over a larger surface area to improve evaporation and fluid transport across the outer housing. The improved fluid transport can increase the comfort for the user and increase the long term wearability of the device by, e.g., preventing skin perspiration from affecting the electrical contact between the sensing and defibrillation electrodes and the skin and from interfering with the adhesive properties of the adhesive. An absorbing section 616 or plurality of sections 616 can be used in conjunction with the wicking layer 614 to further improve the moisture transport between the skin and the device. In some embodiments the absorbing section can be part of the fluid transport element. The adhesive 610 used in the patient engagement substrate can also be perforated in some embodiments to further improve moisture transport across the adhesive layer. The perforated adhesive layer can be part of the fluid transport element.

A semi rigid base chassis 618 can be used to provide additional structural support for the heavier components of the device, such as the device electronics. The illustrated chassis can have the electronics module 620 or modules mounted to the chassis 618. The illustrated defibrillator mounts the electronics 620 to the chassis 618 using a mount frame 622. The electronics can be included within one or more waterproof housings within the device housing(s). The electronics can be connected to the sensor electrodes and defibrillator electrode pads using flexible conductive material that can be routed through the multi-layer structure in the device. Examples of materials that can be used for the semi-rigid chassis 618 include polyester, polyethylene, polystyrene, polyurethane, and vinyl.

The housing 602 can be flexible. In some embodiments the flexible housing can be used to hold the device together. The flexible housing can also be elastic. The housing can be resistant to impacts, tearing, dirt, chemicals, and bacteria. The outer surface of the housing can be low friction to reduce wear and decrease the likelihood of catching on clothing and objects. In some embodiments the outer surface of the housing is water resistant. In some embodiments the outer surface of the housing is hydrophobic. The housing can be waterproof to prevent water from entering the interior of the device through the housing. In some embodiments the housing can be permeable to air. Examples of materials that can be used for the housing include polyester or polyurethane based fabrics. The fabric can be knitted, woven, or non-woven. In some embodiments the housing can be part of the fluid transport element.

The properties of the individual layers can be selected to achieve a wearable defibrillator with the desired mechanical, strength, flexibility, adhesive, electrical, and chemical properties.

Figure 27:
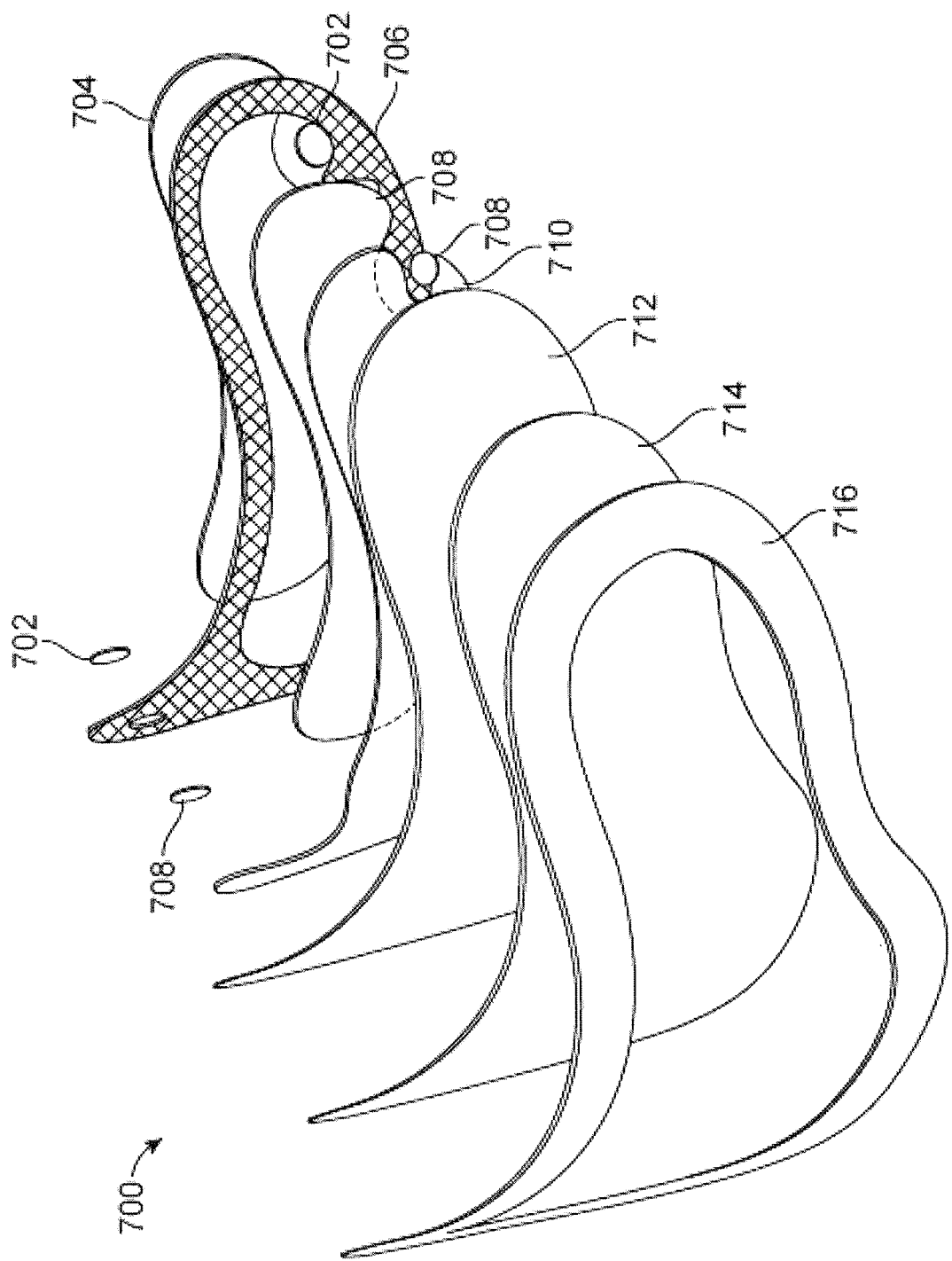
FIG. 27 is a portion of a wearable defibrillator in accordance with some embodiments.
Figure 29:
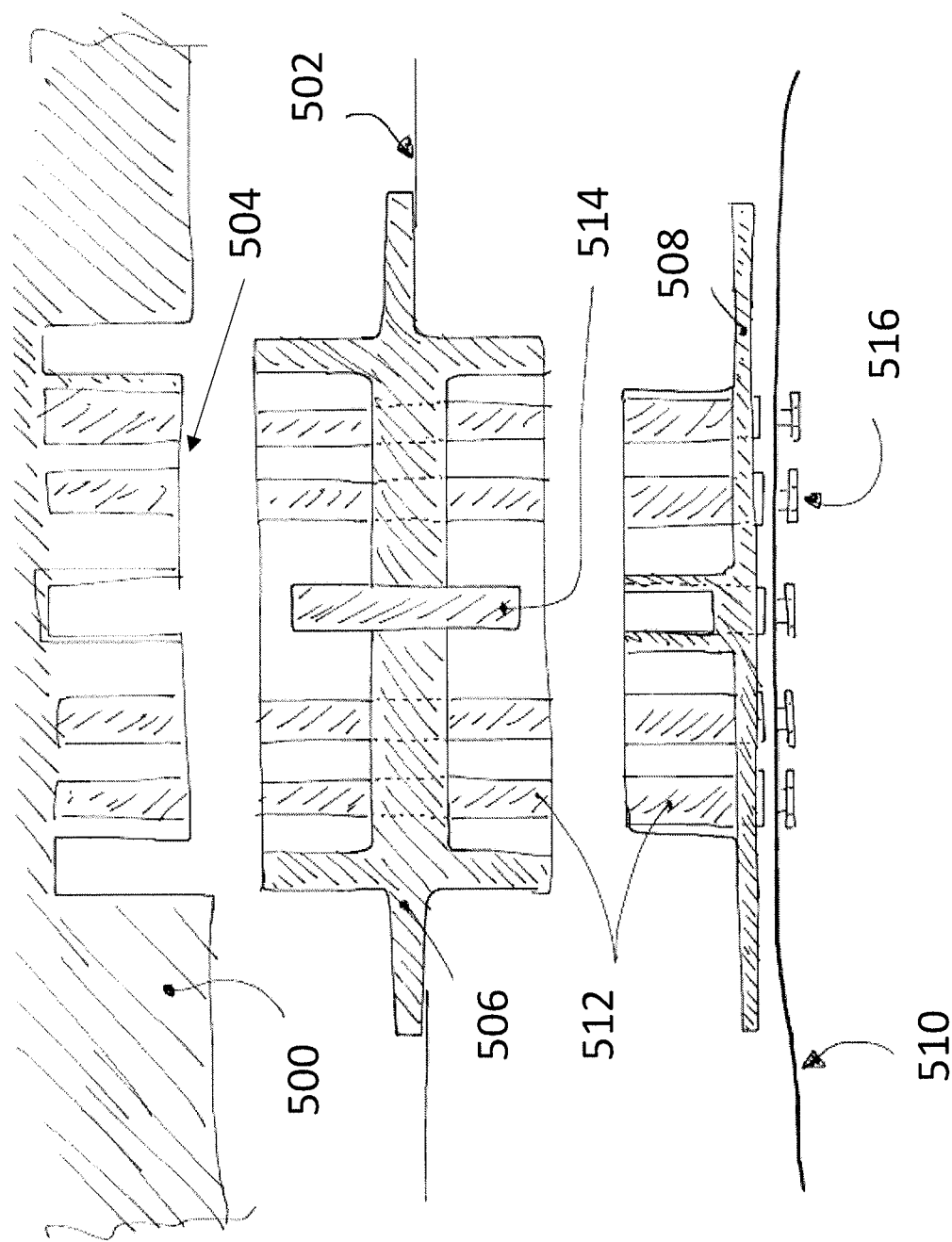
FIG. 29 is a portion of a wearable defibrillator in accordance with some embodiments.

FIG. 27 illustrates an embodiment of a portion 700 of a wearable defibrillator with a multi-layer construction. FIG. 29 shows discrete sections of the sensor electrode hydrogel 702, the defibrillator electrode hydrogel 704, and the adhesive 706 having complementary shapes such that the sensor electrode hydrogel 702, defibrillator electrode hydrogel 704, and adhesive 706 can be combined and arranged in one substrate having a substantially planar layer or shape such that each of the sensing electrodes, defibrillator electrode pad, and adhesive can conform to the skin of the patient. The patient engagement substrate includes the sensor electrode hydrogel 702, defibrillator electrode hydrogel 704, and adhesive 706 and is configured to contact the patient's skin and be suitable for long term wear. The sensor electrode hydrogel 702 can be arranged in multiple discrete electrodes to sense or acquire a cardiac signal at different contact points. The defibrillator electrode hydrogel 704 has a larger surface area to provide sufficient contact with the skin while delivering a defibrillating energy pulse. The adhesive 706 can be a high-tack breathable adhesive. In some embodiments the adhesive 706 can be a gel that is perforated as shown in FIG. 29 to improve the breathability and/or moisture transport properties of the adhesive. The hydrogels used for the defibrillator electrode pad 704 and sensing electrodes 702 can also have adhesive properties to improve electrical contract with the skin and to provide additional structural support for the device.

The adhesive can be selected to support the weight of the wearable defibrillator through activities for a duration of 10-14 days. The adhesive can also be selected for moisture management, to be comfortable and non-irritating, and to be easy to remove. In some embodiments multiple different types of adhesives can be used. Examples of adhesive types that can be used include hydrocolloid, silicone, acrylic, polyolefin, etc. Hydrocolloid adhesive typically have high strength but can be more difficult to remove. Silicone has good strength and can be removed more easily. Perforated silicone in combination with a wicking layer can achieve excellent moisture transport properties while maintaining adhesion to the skin.

A conductive electrode film 708 is illustrated. The conductive electrode film 708 can be in electrical communication with one or more of the sensing electrodes 702 and defibrillator electrode hydrogel 704. In some embodiments the conductive electrode film 708 can be laminated to the support structure, such as a polyester (PET) chassis 710, to form a flex circuit. In some embodiments the additional sensors described herein can also be manufactured within the flex circuit for easier manufacturing. A support structure 710 is illustrated in FIG. 29. The support structure 710 can be used to support the device electronics and spread the shear load of the device across the footprint of the device. The support structure 710 can be semi-rigid to provide support for the electronics and to improve weight distribution. A moisture transport material 712 can be used to improve moisture transport from the electrode and adhesive side of the device towards the exterior of the device. The moisture transport material 712 can be a wicking fabric. Examples of wicking materials include materials such as cotton, polyester, and non-woven constructions. The moisture transport layer can pull moisture from the skin through the adhesive and hydrogels. In some embodiments the moisture or fluid transport layer has an absorption capacity of greater than about 500%. In some embodiments the fluid transport or wicking layer is a non-woven fabric that is a mixture of polyester and cellulose. In some embodiments the ratio of cellulose to polyester can be from about 45/55 to 65/35 with a basis weight from 30-120 $g/m^2$. In one example the layer is a 50/50 mixture of cellulose and polyester with a basis weight of 70 $g/m^2$ and has an absorption capacity of about 850%.

An outer housing material 714 is illustrated. The outer housing material 714 can be made out of a fabric, laminate, or other material or structure that is breathable and has some water resistance. The outer housing material 714 can be flexible and abrasion resistant to reduce friction between the outer housing material and clothing. Examples of outer housing materials 714 include nonwoven fabrics, laminate structures, and laminate fabric structures. In some embodiments a non-woven polyurethane fabric material can be used as the outer housing. Laminate structures can include an outer layer, membrane layer, and inner layer. The outer layer, membrane layer, and inner layer materials can be selected to provide a breathable laminate structure with a hydrophobic outer surface to provide water resistance. In some embodiments the outer housing material is water resistant. In some embodiments the outer housing material is hydrophobic. In some embodiments the outer housing material is waterproof.

An outer adhesive border 716 is illustrated. The adhesive border 716 is configured to connect to the perimeter of the device and to adhesively engage with the skin to improve adhesion between the portion of the wearable defibrillator and the patient's skin. The adhesive border 716 can be made out of a thin and flexible non-woven polyurethane with a high-tack adhesive. The adhesive border 716 can form a substantially waterproof seal between the perimeter of the device and the patient's skin to prevent water from passing from the exterior of the device to the area between the electrodes and the patient's skin. The adhesive border 716 can have a tapered cross section.

The wearable defibrillators described herein can include additional sensors. Examples of sensors include: a voice recognition module, an ultrasound transceiver or transducer configured to transmit and/or receive ultrasonic signals, a Doppler radar configured to transmit a microwave signal and receive a returned microwave signal, a pulse oximeter configured to measure an oxygen content of a blood of the patient at a point on a chest of the patient, an inclinometer configured to determine the position and orientation of the wearable defibrillator, a radio beacon configured to transmit the location of the wearable defibrillator, a GPS sensor, a wireless radio configured to wirelessly transmit data from the wearable defibrillator, and a sensor configured to measure a mechanical stretch of a portion of the wearable defibrillator. In some embodiments an accelerometer, such as a 1 g accelerometer, can be used with the wearable defibrillator to indicate the rotation of the device in one to three axes of rotation. The orientation can be useful during device application to indicate whether the device is right side up and whether it is tilted at an appropriate or inappropriate angle.

Figure 28:
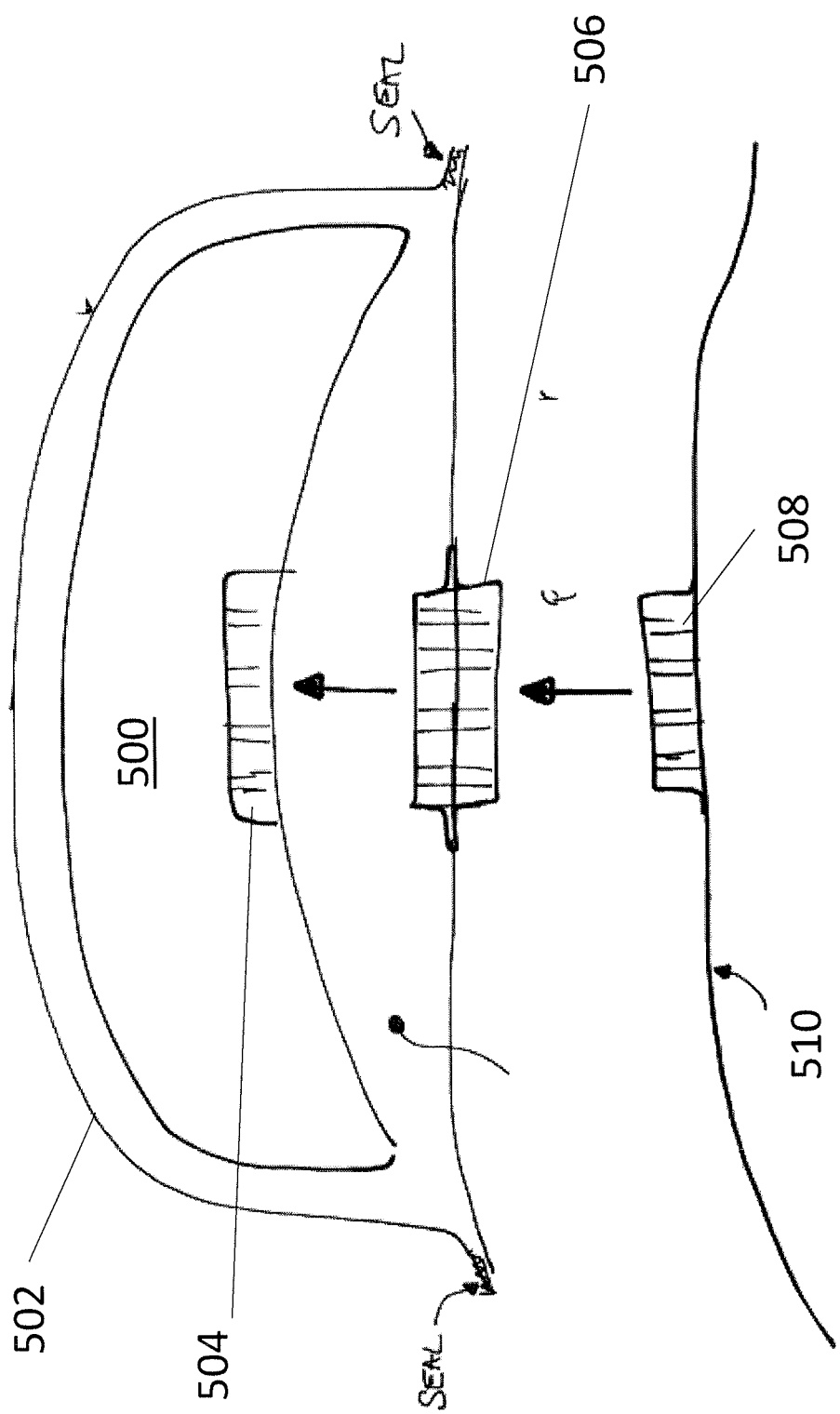
FIG. 28 is a portion of a wearable defibrillator in accordance with some embodiments.

FIG. 28 is a portion of a wearable defibrillator in accordance with some embodiments. FIG. 28 illustrates a housing 500 contained within a sealed enclosure 502. The exterior of the housing can be water resistant. The sealed enclosure 502 can also be water resistant or water proof to prevent moisture or other fluids from contacting the housing 500. The illustrated housing 500 has a connector plug receptacle 504 configured to engage with a connector 506 embedded with the sealed enclosure 502. The connector 506 can engage with a connector 508 that is part of the flex circuit 510 of the patient engagement substrate. The connector plug 504/connector 506/connector 508 can include a plurality of electrical connections that can allow for electrical communication between the housing and the electrodes and sensors that are engaged with the wearable defibrillator. For example, the connector plug can include connections corresponding to the defibrillator electrode pads, the plurality of sensing electrodes, and any additional sensors. FIG. 29 is an enlarged view of the connector plugs 504, 506, 508. The connector 506 and connectors 504/508 include complementary surfaces for ECG sensing electrode electrical connections 512 and for the defibrillator electrical connection 514. The flexible circuit 510 also includes a plurality of rivets 516 for the electrical connections from the connectors 504, 506, and 508 and the flexible circuit 510.

The use of the sealed enclosure can make it easier to download data from the housing and refurbish the housing for subsequent use with another patient engagement substrate. Refurbishing the housing can include one or more of the following steps: 1) receiving the device after use; 2) cutting through the sealed enclosure/waterproof skin to expose the housing; 3) removing the housing (containing batteries, caps, electronics, memory) from the disposable patch (patient engagement structure); 4) the housing may not get opened, except (potentially) for a battery compartment to replace/recharge batteries; 5) batteries could also be charged through a sealed connector on housing (i.e. don't have to open housing at all); 6) plugging into the housing to extract data from the memory; 7) copying data to an external system; 8) erasing memory on the device; 9) recharging or replacing the battery; 10) running a functional test/diagnostics; 11) reprograming; and 12) sealing the housing with a new sealed enclosure/waterproof skin and adding to a new patient engagement structure to create a new device for use by the next patient/wearer.

Figure 30:
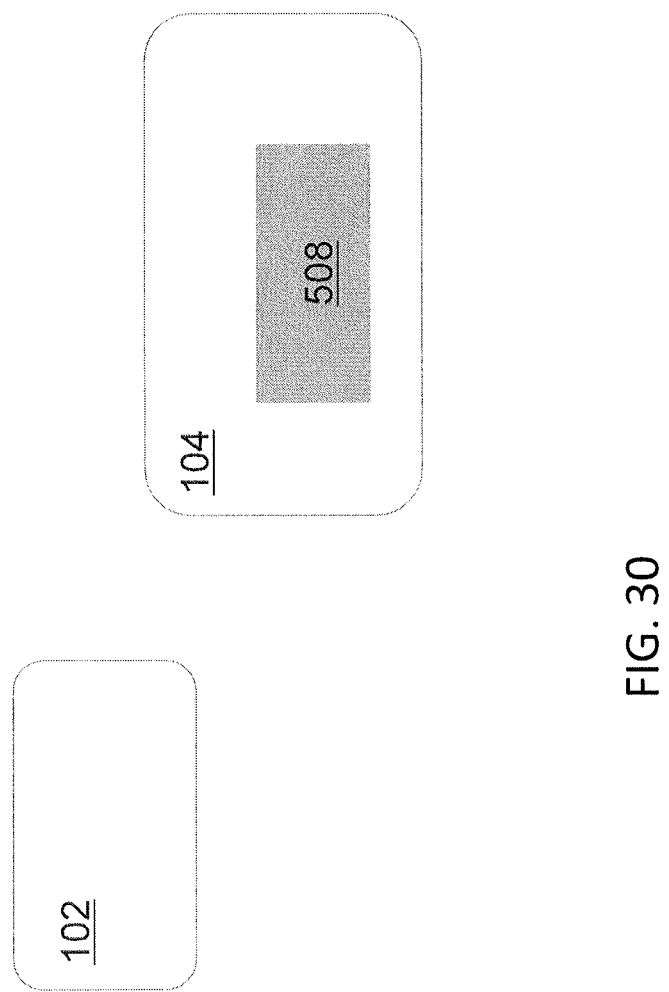
FIG. 30 is a schematic illustration of an upper and lower patch that can be used with the wearable defibrillators described herein.

FIG. 30 is a schematic illustration of an upper and lower patch that can be used with the wearable defibrillators described herein. The illustrated lower patch can be used to support the housing as described herein and can include the universal connector/connector plug engaged with the housing.

Figure 31:
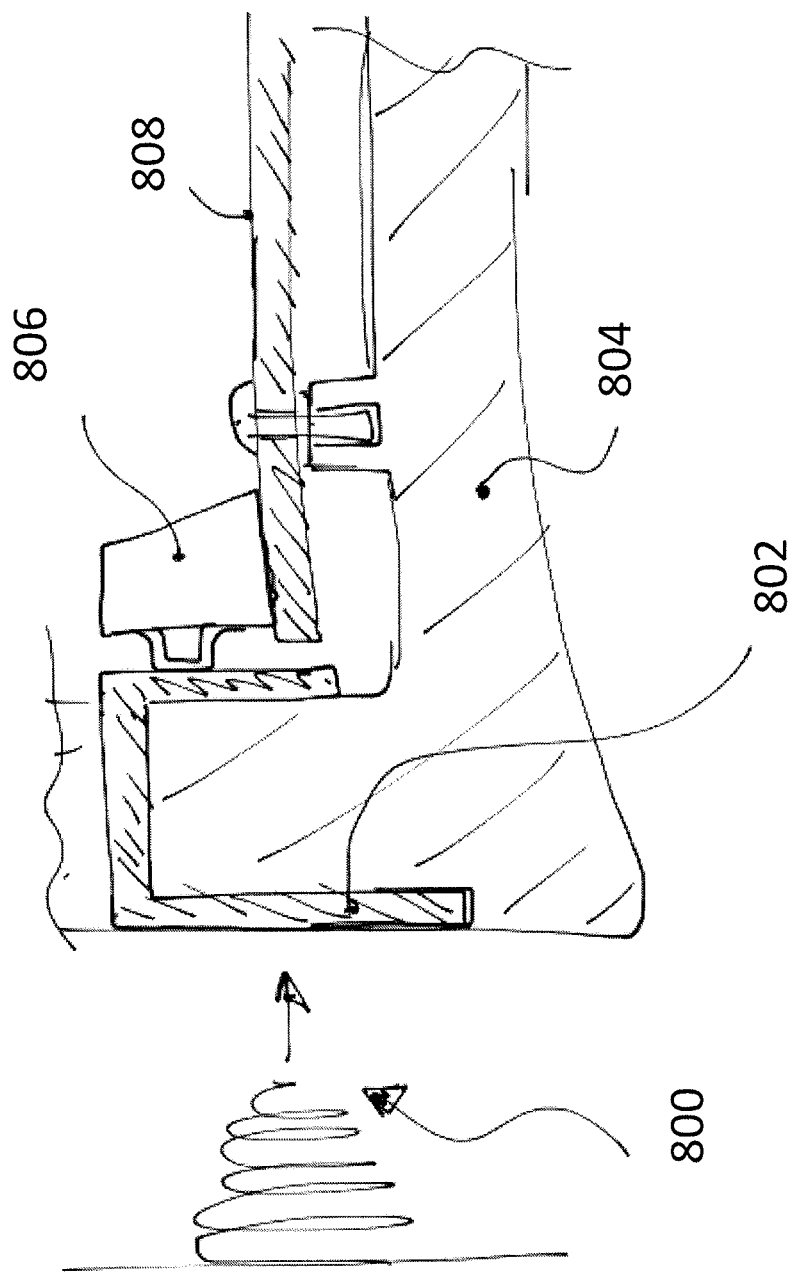
FIG. 31 is a portion of a wearable defibrillator in accordance with some embodiments.
Figure 32:
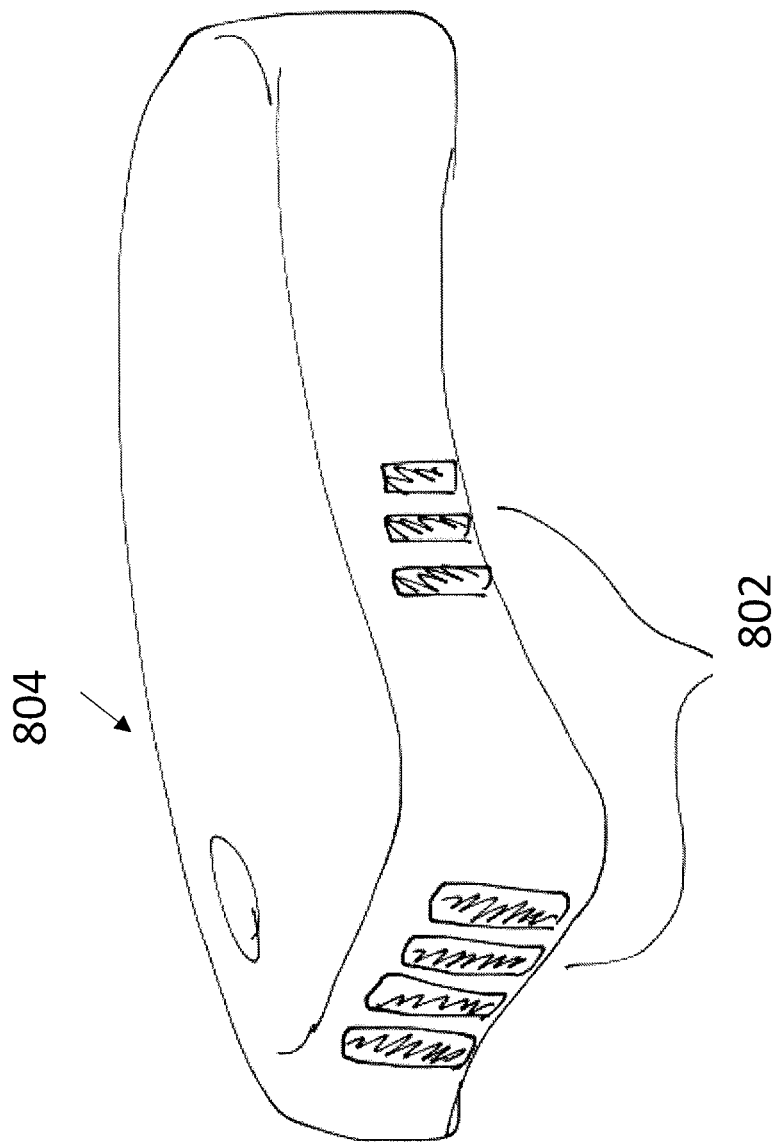
FIG. 32 is a housing that can be used with the wearable defibrillators described herein.

FIG. 31 illustrates a battery charger and/or programmer cable 800 that can be used to engage with an exterior electrical contact 802 of the housing 804 to download data and/or charge the batteries within the housing. The electrical contact 802 can utilize a spring connector 806 to facilitate electrical contact with the PCB 808. FIG. 32 is a housing 804 showing the exposed electrical contacts 802 that can be used to transmit data and/or receive an electrical charge.

Figure 33:
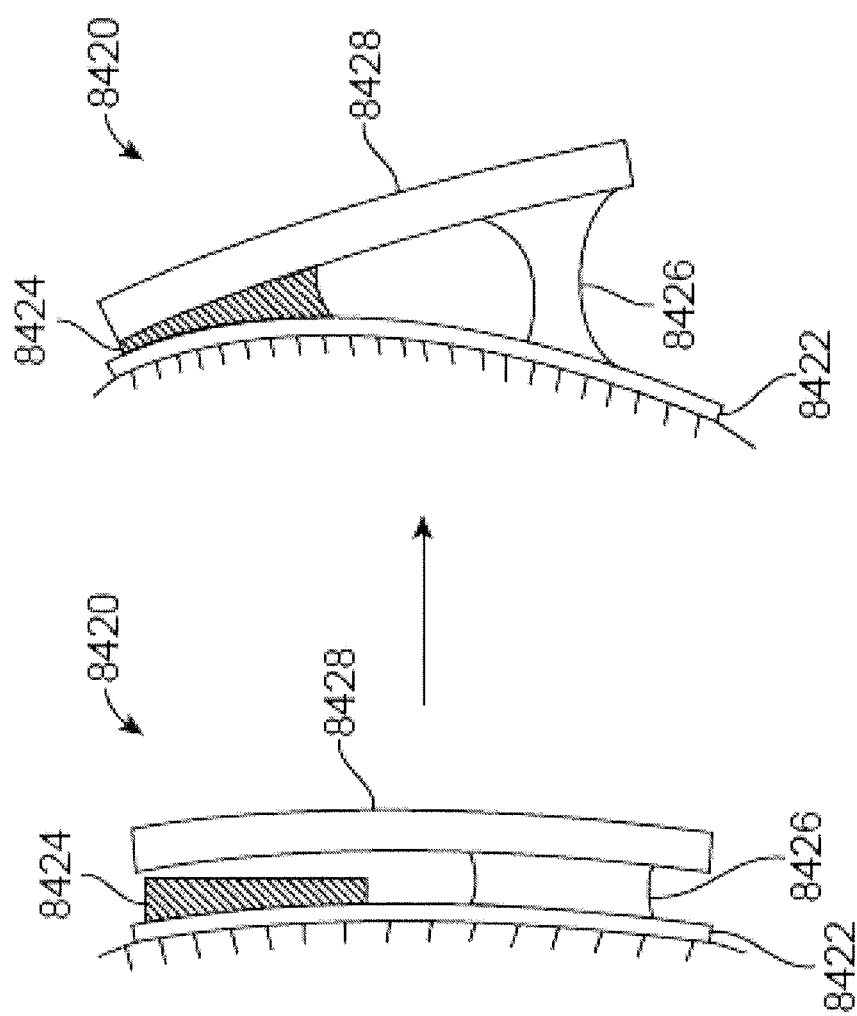
FIG. 33 is a cross-sectional view of a portion of a wearable defibrillator.

FIG. 33 is cross-sectional view of a portion of a wearable defibrillator. FIG. 33 illustrates a device 8420 that can include an adhesive 8422, a bonding layer 8424 and a stretchable anchor 8426 to support the defibrillator components 8428 off of the body. The stretchable anchors 8426 can be used with the bonding layer to allow relative movement between the adhesive 8422 and bottom of the more rigid defibrillator components 8428 to improve the overall flexibility of the device and to decrease the likelihood of the adhesive 8422 pulling off of the skin of the wearer during movement.

Figure 34:
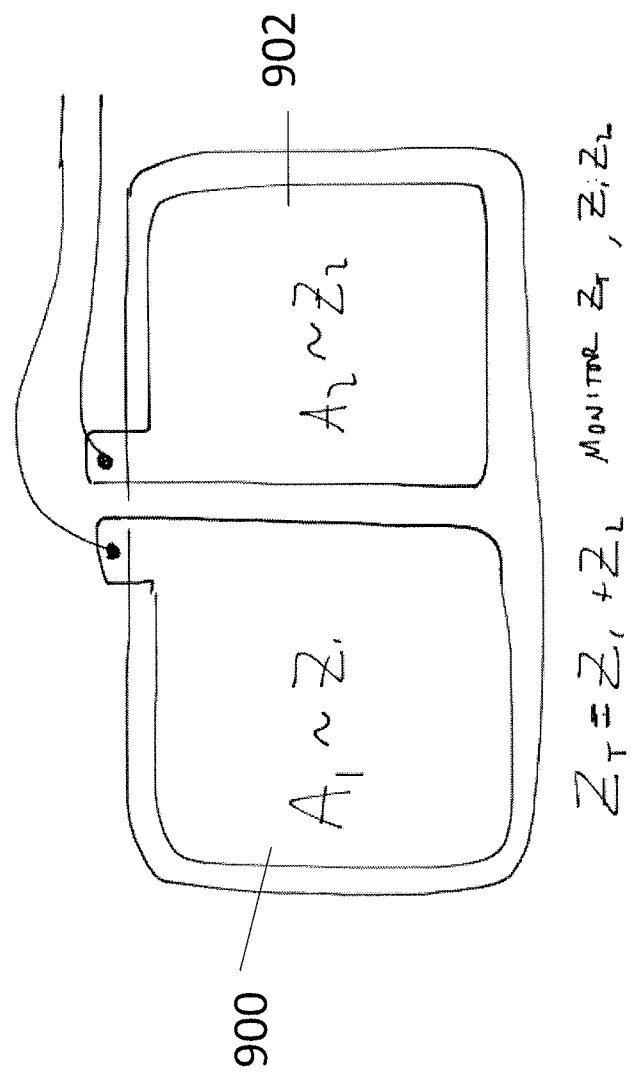
FIG. 34 illustrates a pair of electrodes that can be used in the wearable defibrillators described herein.

FIG. 34 illustrates a pair of electrodes 900, 902 that can be used in the wearable defibrillators described herein. The impedance between the pair of electrodes 900, 902 can be analyzed to determine the quality of the electrical contact between the electrodes and the skin of the patient. The pair of electrodes 900, 902 can make up one of the defibrillator electrode pads. In some cases a transthoracic impedance between the first pair of electrodes and a second pair of electrodes (e.g. second defibrillator electrode pad) can be determined.

Figure 35:
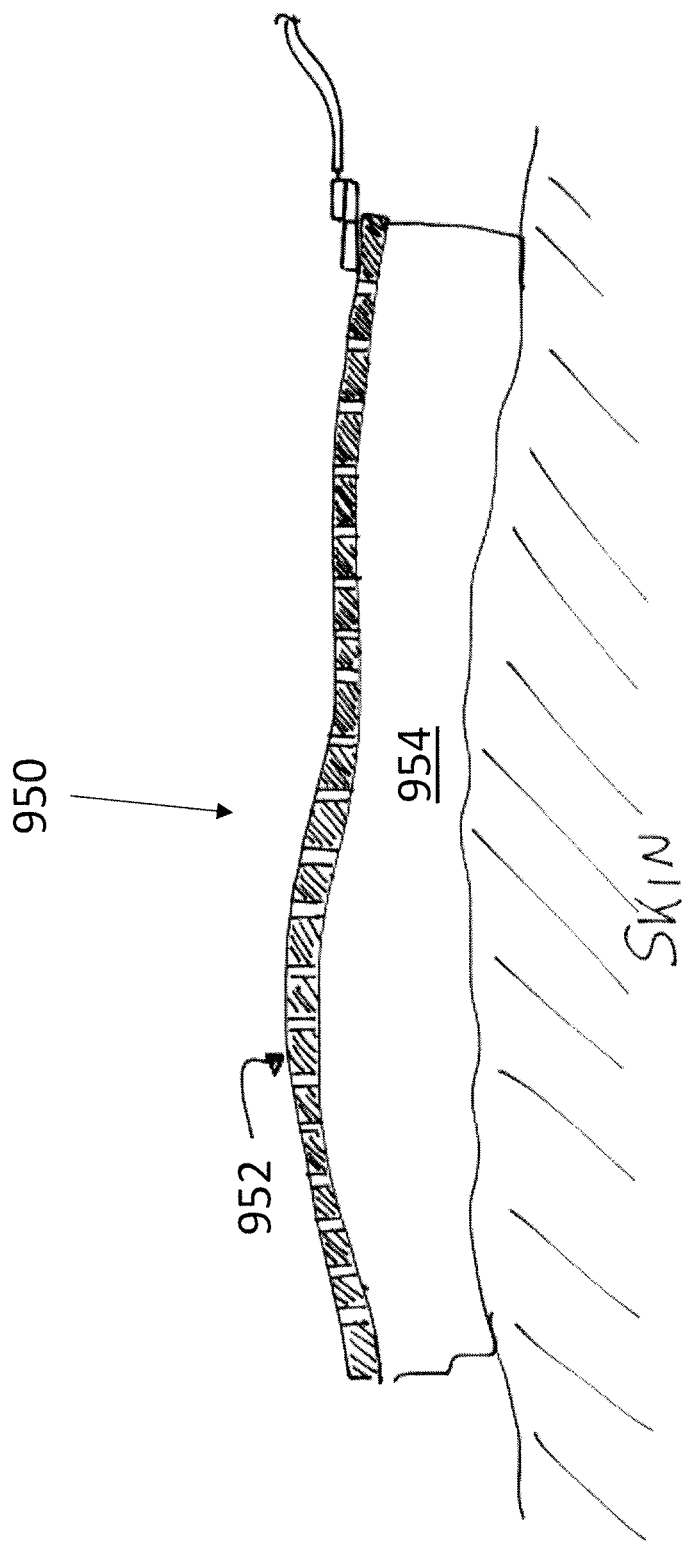
FIG. 35 illustrates a cross-sectional view of a configuration of a defibrillator electrode that can be used in the wearable defibrillators described herein.

FIG. 35 illustrates a cross-sectional view of a configuration of a defibrillator electrode 950 that can be used in the wearable defibrillators described herein. The illustrated electrode configuration 950 in FIG. 35 can be used for the defibrillator electrode pad. The illustrated electrode 950 includes a perforated electrode 952 engaged with a conductive adhesive/hydrogel 954 and an electrical connection that traces back to the housing. The electrode could be made of a carbon vinyl film. The carbon vinyl film could be with or without an Ag or Ag/AgCl coating on one or both sides. The electrode film could be solid or have perforations to allow moisture to move through. In some cases the electrode can have a woven structure that is air permeable. In one example the electrode is a woven carbon fabric. In some cases the electrode is a conductive hydrogel. The conductive hydrogel can be a cross-linked polymer with water and a salt to promote conductivity. In some cases a conductive hydrocolloid can be used. The conductive hydrocolloid can be a mixture of rubber, tackifier, absorber, and conductive filler. Examples of conductive fillers include: carbon nanotubes, graphite, carbon black, silver nanowires, and graphene sheets.

FIG. 36 illustrates a picture of microneedles and an electrode configuration with micro-needles 970 in accordance with some embodiments. In some embodiments any of the electrodes disclosed herein can include micro-needles. The micro-needles can be configured to penetrate the stratum corneum (SC) to deliver the electrical energy to the epidermis.

Figures 37A, 37B, 37C:
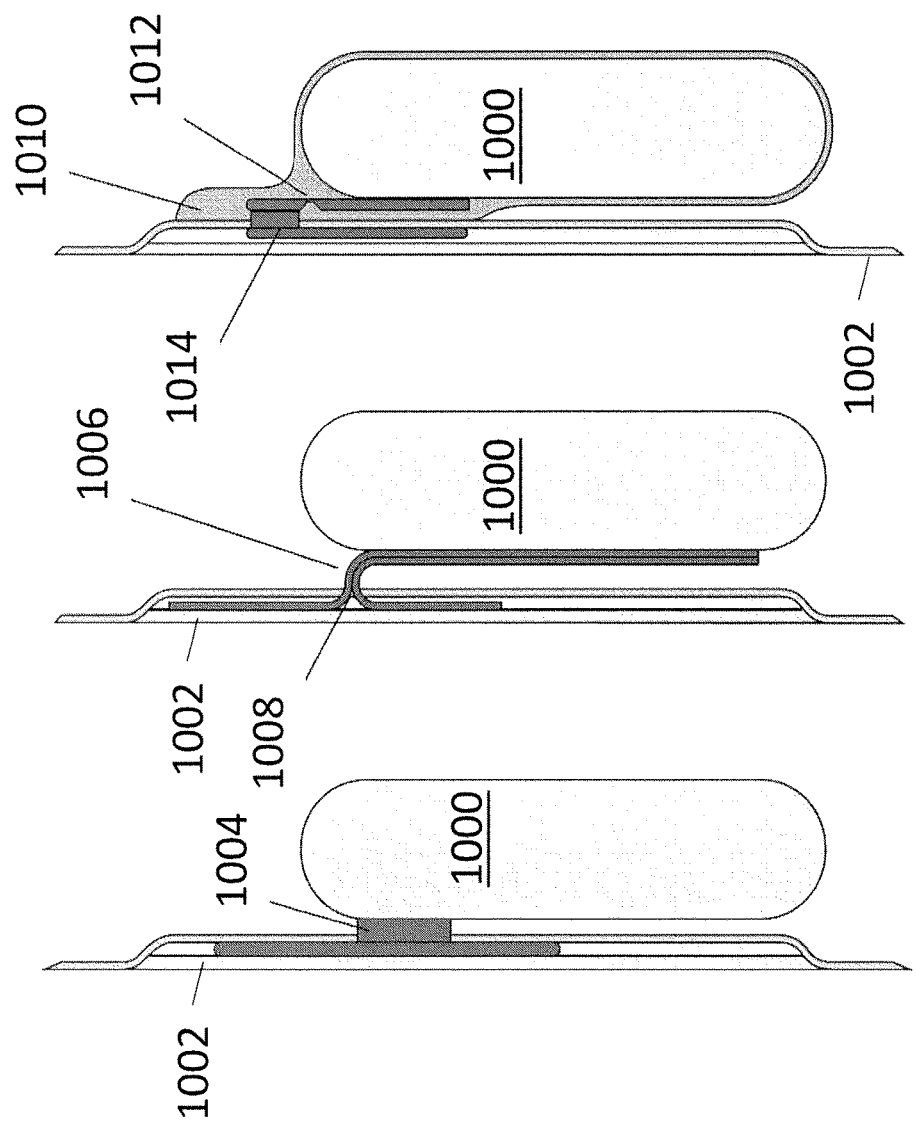
FIGS. 37A-37C illustrate embodiments of connections between a housing and patient engagement substrate that can be used in the embodiments of the wearable defibrillators disclosed herein.

FIGS. 37A-37C illustrate embodiments of connections between a housing 1000 containing electronics components and patient engagement substrate 1002 that can be used in the embodiments of the wearable defibrillators disclosed herein. As shown in FIGS. 37A-37C a flexible connection 1004 can be used between the housing 1000 and patient engagement substrate 1002. The flexible connection 1004 can be used to support the weight of the housing 1000, such as the weight of the battery, capacitors, and energy source within the housing. The flexible connection can also include electrical interconnects between the housing and the one or more sensing electrodes, defibrillator electrode pads, and any other sensors or electrical components on the wearable defibrillator. The use of the flexible connection can allow the housing to articulate away from the body during movement to reduce the likelihood of the patient engagement substrate losing adhesion with the skin. FIG. 37A illustrates the housing 1000 supported by a flexible connector 1004 at one end of the housing. FIG. 37B illustrates the housing 1000 supported with a flexible hinge 1006 at one end of the housing 100 along with a connector 1008 running along one surface of the housing. FIG. 37C illustrates a housing 1000 with a fabric covering 1010 that is supported by a flexible hinge 1012 and connector 1014. All three of the flexible connections illustrated in FIGS. 37A-37C include a plurality of electrical connections between the housing and the patient engagement substrate. The flexible connection can include a plug connection that can reversibly and removably connect the housing with the patient engagement substrate.

Figure 38:
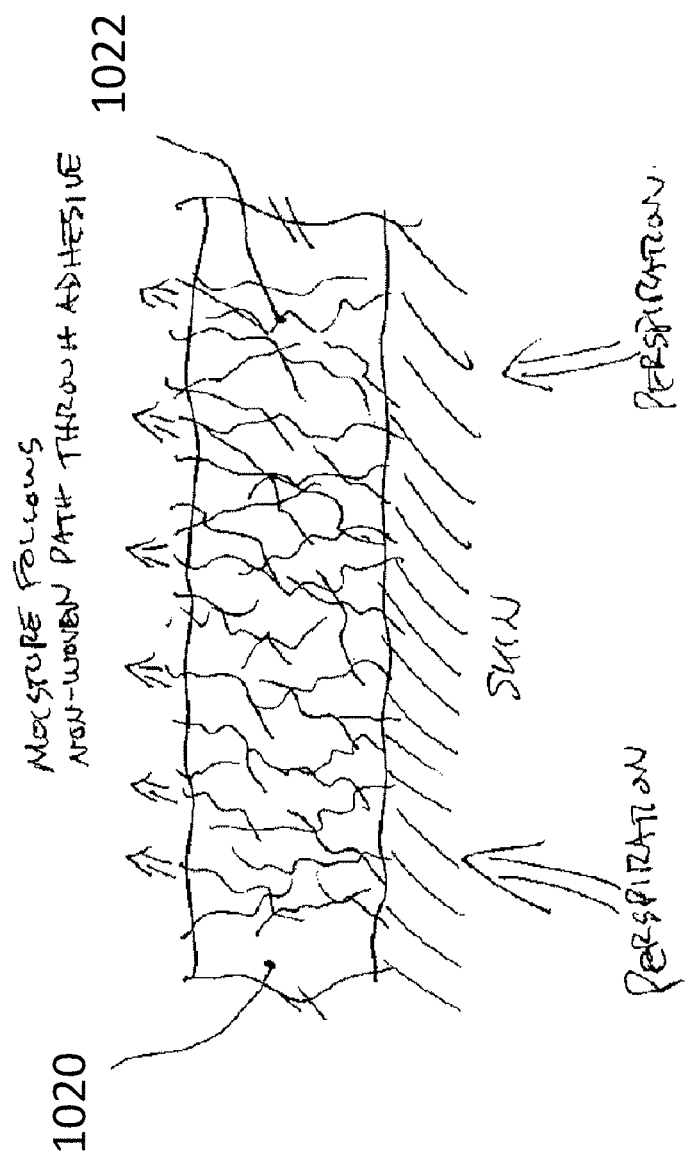
FIG. 38 is a schematic illustration of moisture transport across an embodiment of a conductive adhesive that can be used in the wearable defibrillators disclosed herein.

FIG. 38 is a schematic illustration of moisture transport across an embodiment of a conductive adhesive 1020 that can be used in the wearable defibrillators disclosed herein. FIG. 38 shows a conductive adhesive hydrogel 1020 that is hydrophobic but includes a hydrophilic structure. FIG. 38 illustrates a hydrophilic mesh/non-woven material 1022 within the hydrophobic bulk layer. The hydrophilic mesh/non-woven material 1022 provides a water transport mechanism to transport water from one side of the adhesive 1020 to the other side of the adhesive as shown in FIG. 38.

Figure 39:
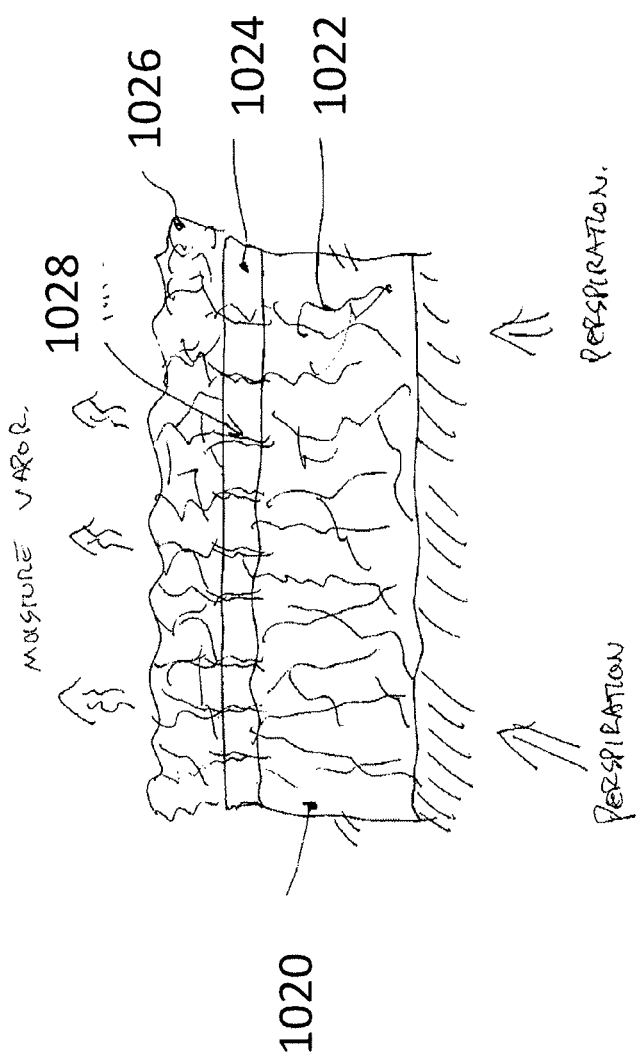
FIG. 39 is a schematic illustration of moisture transport across an embodiment of a conductive adhesive and electrode that can be used in the wearable defibrillators disclosed herein.

FIG. 39 is a schematic illustration of moisture transport across an embodiment of a conductive adhesive 1020 and electrode 1024 that can be used in the wearable defibrillators disclosed herein. FIG. 39 illustrates a conductive adhesive 1020, such as a hydrocolloid or hydrogel bulk material with a non-woven wicking material 1022 within the adhesive 1020. The conducive adhesive contacts an electrode layer 1024 having a plurality of openings. The electrode layer also contacts a non-woven wicking material 1028. The configuration illustrated in FIG. 39 can move moisture from the surface of the skin through the non-woven wicking material 1022 present in the conductive adhesive 1020 through the plurality of openings in the electrode layer 1024 and through the non-woven wicking material 1028. The improved moisture transport can increase the long term wearability of the electrode and wearable defibrillators disclosed herein. The non-woven wicking material 1028 can include a hydrophilic fiber sewn through the thickness of the configuration shown in FIG. 39. The hydrophilic fiber can be sewn through at regular intervals or at certain points of the electrode. The hydrophilic fiber improves water transport and also improves the mechanical properties and adhesion between different layers of the device.

Figure 40:
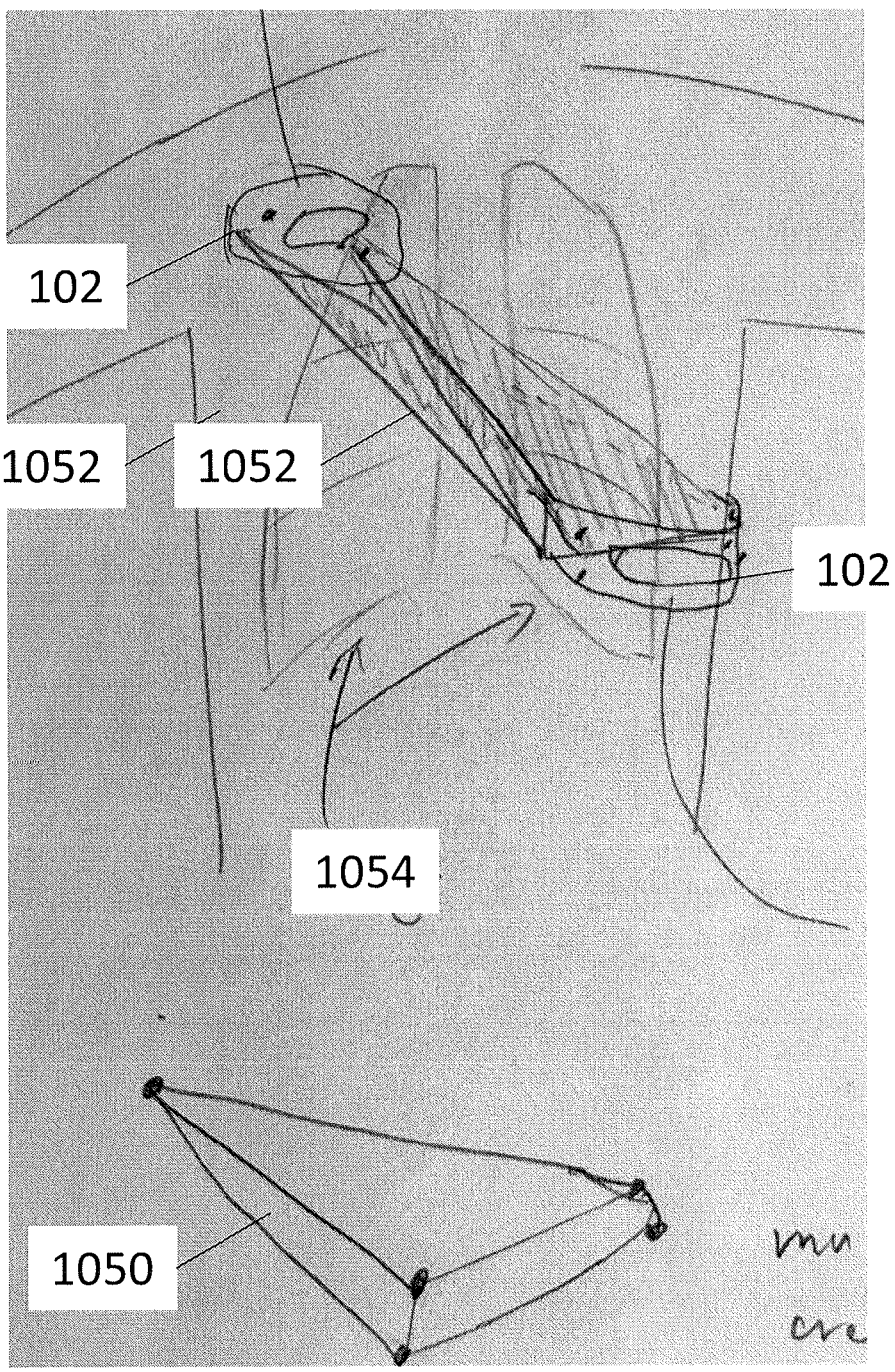
FIG. 40 is a schematic illustration of a portion of a wearable defibrillator measuring a multi-vector trans-thoracic impedance of a patient in accordance with some embodiments.

FIG. 40 is a schematic illustration of a portion of a wearable defibrillator measuring a multi-vector trans-thoracic impedance of a patient in accordance with some embodiments. FIG. 40 illustrates the upper patch 102 and lower patch 104 of a wearable defibrillator. The sensing electrodes on each of the upper patch 102 and the lower patch 104 can measure a multi-vector trans-thoracic impedance 1050 of the patient 1052 as shown in FIG. 40. The multiple vectors create numerous pathways to assess the impedance of the patient, which allows for sampling of various lung lobes 1054 on both the right and left side of the chest. Assessing different lobes can provide more accuracy regarding fluid states and also help with clarifying fluid changes due to patient position.

The devices described herein can be used to monitor a patient for symptoms associated with sleep apnea. In some embodiments the wearable defibrillators can be modified to be adapted to monitor a patient for sleep apnea. For example a single patient engagement substrate can be used in the sleep apnea monitoring device. The capacitors can be omitted in the sleep apnea monitoring device. The controller and energy source can be adapted to power and process the sensors used to detect the symptoms associated with sleep apnea. In some embodiments a wearable device for treating a patient and detecting symptoms associated with sleep apnea are provided. The device can include a patient engagement substrate comprising an adhesive, one or more sensors, a first fluid transport element configured to transport fluid away from the skin to allow the wearable device to be worn continuously, and a first vapor permeable layer, the one or more sensors adapted to detect one or more of a pulse, a cardiac signal, oxygen content of the blood, impedance, galvanic skin impedance, temperature, breathing rate, heart sounds, and heart rate of the patient; and a controller configured to receive data collected by the one or more sensors and analyze the data to determine if the patient exhibits a symptom associated with sleep apnea. The wearable device can be configured to provide a stimulus to the patient upon detection of a symptom associated with sleep apnea. Examples of stimuli include a vibration, an electrical shock, a visual alert, electronic notification, or auditory alarm. Any of the sensors described herein can be used with the device to detect the symptoms associated with sleep apnea in the patient wearing the device. The controller can be configured to apply an algorithm to the data collected by the one or more sensors. In some embodiments the algorithm adapts to the specific patient wearing the device. The controller can be adapted to modify the frequency of the sampling of the sensor data to efficiently receive and analyze the collected data. The controller can be adapted to selectively turn sensors on and off based on the relevant data collected with each sensor for the specific sleep apnea symptoms and the specific patient characteristics. The controller can be adapted to change the sensitivity of each of the sensors for the specific sleep apnea symptoms and the specific patient characteristics. The one or more sensors can be onboard the device or part of the patient engagement substrate or separate from the patient engagement substrate. For example, a wireless sensor can transmit data wirelessly to the device or a wired sensor can transmit data via a wired connection to the device. The wearable device can be adapted to transmit data wirelessly over a computer network to communicate with or provide information via a companion smart phone application.

Figure 41A:
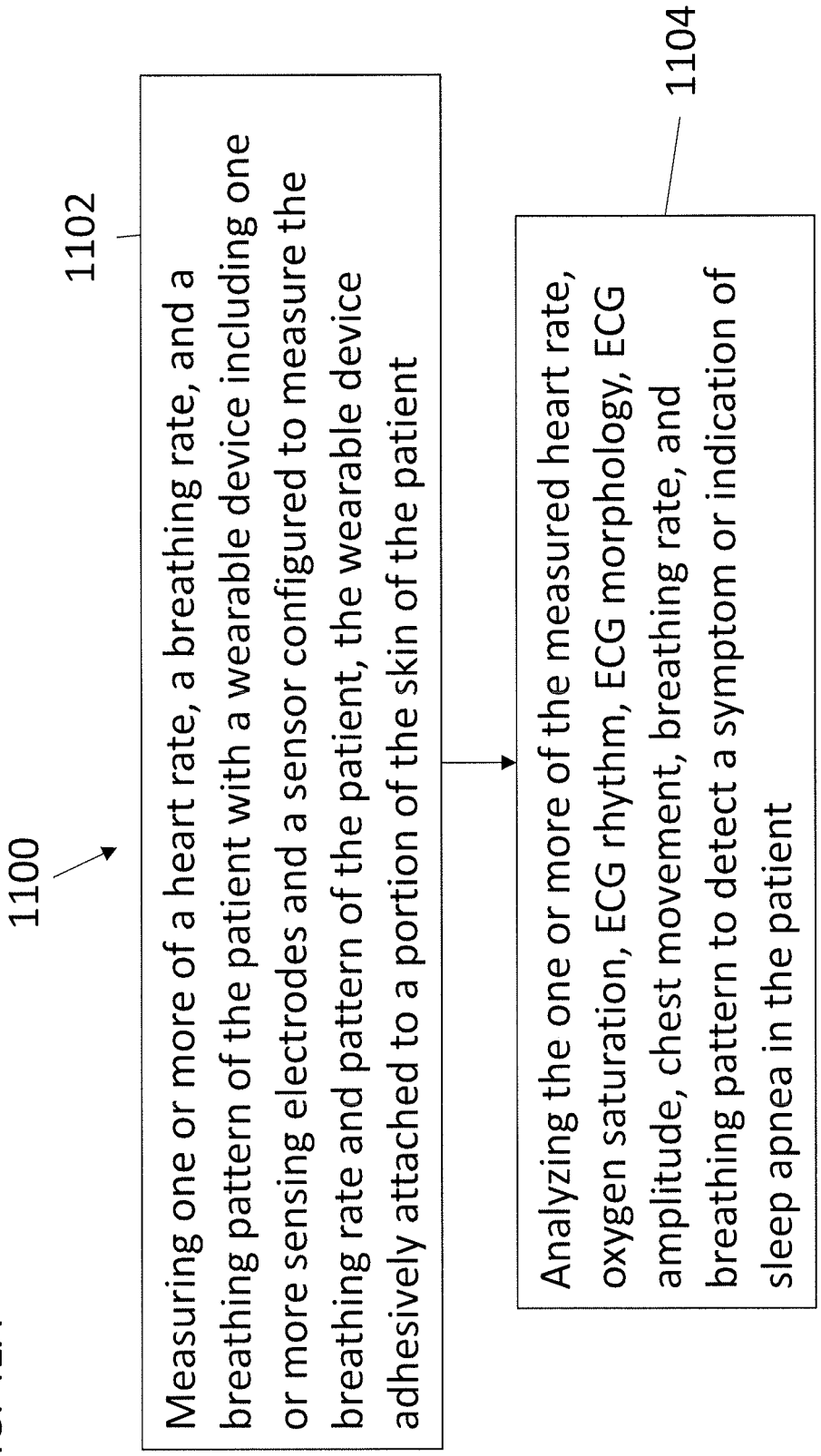
FIG. 41A is a flow chart of a method for detecting symptoms associated with sleep apnea in a patient in accordance with some embodiments.
Figure 41B:
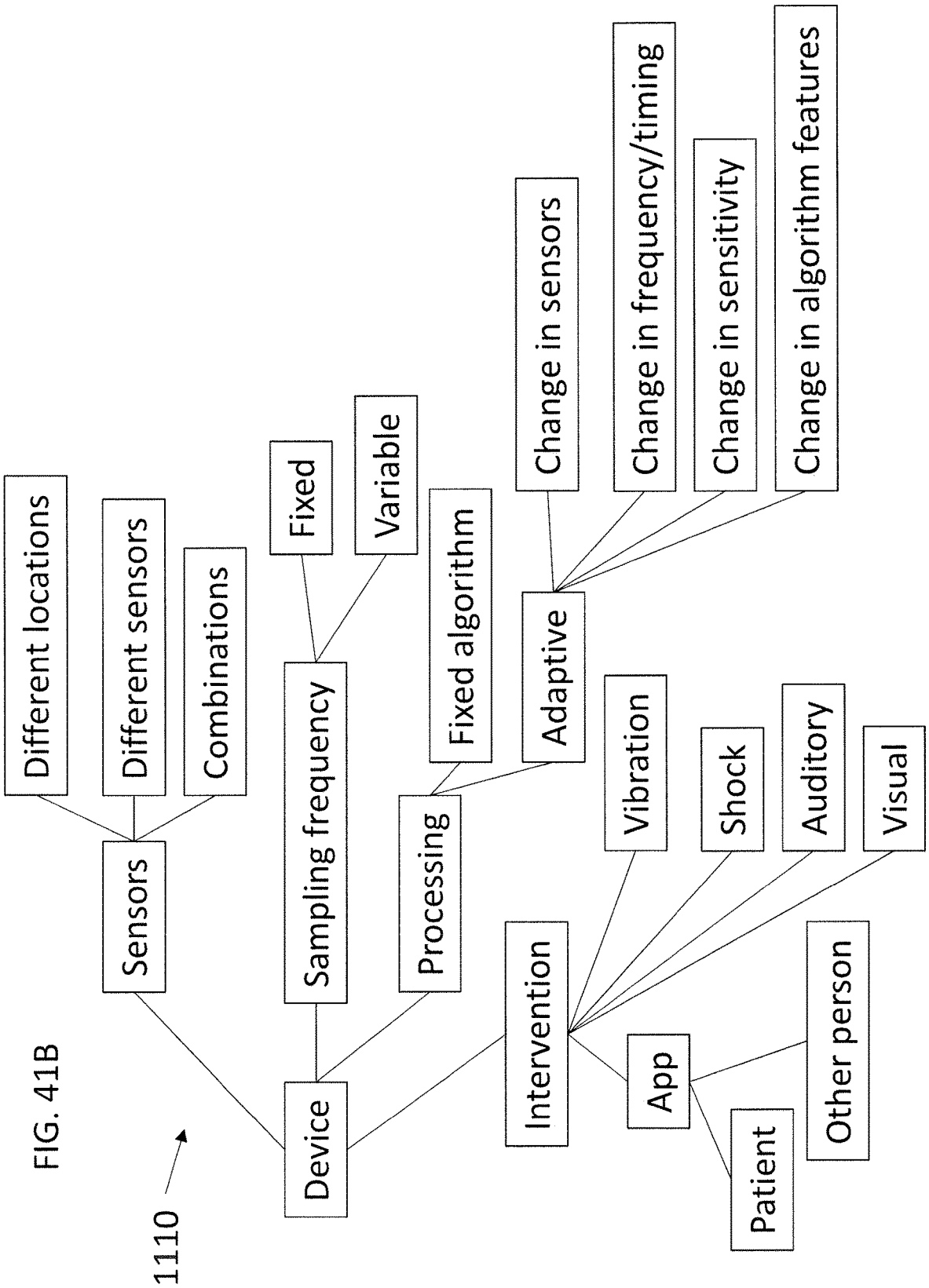
FIG. 41B illustrates a schematic flow chart of a method of detecting symptoms associated with sleep apnea in a patient in accordance with some embodiments.

FIG. 41B illustrates a schematic of a method of detecting symptoms associated with sleep apnea in a patient 1110 using the devices described herein. The device can obtain data from the patient from sensors on board the device or in communication with the device. The sensors can be placed at different locations, can include different sensors, and a combination of different sensors. The device can modify the sampling frequency of any of the sensors. The sampling frequency can be fixed or can be variable. The device controller can process the collected data using a fixed algorithm or an adaptive algorithm. The adaptive algorithm can adapt to the specific patient using the device. The adaptive algorithm can analyze and make changes in the sensors, changes in the frequency/timing of the sampling, changes in the sensitivity of the sensors, and changes to the algorithm features. If the device detects a symptom associated with sleep apnea or other data of interest the device can provide an intervention to the patient. Examples of interventions include a vibration alert, a shock, an auditory alert, and a visual alert. Visual alerts can be provided through the device or as part of a hand held computer applications, such as a smartphone application or tablet computer application. The alerts can be provided directly to the patient, a healthcare provider, family member, or other person based on the user preferences or severity of the detected medical issue.

In some embodiments the devices described herein can be adapted to monitor and treat sleep apnea in the wearer. FIG. 41A is a flow chart of a method 1100 for detecting symptoms associated with sleep apnea in a patient in accordance with some embodiments. The method 1100 for treating sleep apnea includes measuring one or more of a heart rate, a breathing rate, and a breathing pattern of the patient with a wearable device including one or more sensing electrodes and a sensor configured to measure the breathing rate and pattern of the patient, the wearable device adhesively attached to a portion of the skin of the patient 1102; and analyzing the one or more of the measured heart rate, oxygen saturation, ECG rhythm, ECG morphology, ECG amplitude, chest movement, breathing rate, and breathing pattern to detect a symptom or indication of sleep apnea in the patient 1104. In some embodiments the methods include upon detection of the symptom or indication of sleep apnea in the patient, generating and providing a stimulus to the patient. Examples of providing a stimulus include providing a vibration, electrical shock, or auditory alarm.

FIG. 42 is a flow chart illustrating a method 1120 of providing instructions for placing the wearable defibrillators described herein. The method 1120 for providing instructions for placing a wearable defibrillator on a patient includes: providing instructions on where to put a first patient engagement substrate of the wearable defibrillator on a torso of the patient, the first patient engagement substrate including one or more sensing electrodes, adhesive, and a first defibrillator electrode pad, the instructions including where to put the one or more sensing electrodes and first defibrillator electrode pad on the chest of the patient 1122; providing instructions on where to put a second patient engagement substrate of the wearable defibrillator, the second patient engagement substrate including a sensing electrode, adhesive, and a second defibrillator electrode pad, the instructions including where to put the one or more sensing electrodes and second defibrillator electrode pad 1124; verifying a first patient engagement substrate placement on the torso of the patient including the placement of the one or more sensing electrodes and first defibrillator electrode pad 1126; and verifying a second patient engagement substrate placement on the chest of the patient including the sensing electrode and second defibrillator electrode pad 1128.

Instructions can be provided to the patient or to a person applying the wearable defibrillator to the patient. In one example the person applying the wearable defibrillator is a health care provider. Typically a health care provider will apply the wearable defibrillator the first time the patient uses the wearable defibrillator. Second and subsequent applications of the wearable defibrillator can be done by the patient, a health care provider, or person assisting the patient.

A variety of release liners can be used to cover the portions of the wearable defibrillator that contact the skin of the patient. Instructions can also include instructions for removing release liners that cover portions of the patient engagement substrate such as the ECG sensing electrode gels, adhesive, and defibrillator electrode pad gels.

In one embodiment a first sensing electrode release liner is configured to cover the one or more sensing electrodes on the patient engagement substrate, a first defibrillator electrode pad release liner is configured to cover the first defibrillator electrode pad, and a first adhesive release liner configured to cover the adhesive on the first patient engagement substrate. In one embodiment a second sensing electrode release liner is configured to cover the one or more sensing electrodes on the second patient engagement substrate and a second defibrillator electrode pad release liner is configured to cover the second defibrillator electrode pad, and a second adhesive release liner is configured to cover the adhesive on the second patient engagement substrate. The instructions can be provided to sequentially remove the first sensing electrode release liner, the first defibrillator electrode pad release liner, and the first adhesive release liner. The instructions can be provided to sequentially remove the second sensing electrode release liner, the second defibrillator electrode pad release liner, and the second adhesive release liner.

In some embodiments two or more release liners are used to cover the surfaces of each of the patient engagement substrates. In one embodiment a primary patient engagement substrate release liner is configured to cover a first portion of the patient engagement substrate; a secondary patient engagement substrate release liner is configured to cover a second portion of the patient engagement substrate; a primary second patient engagement substrate release liner is configured to cover a first portion of the second patient engagement substrate; and a secondary second patient engagement substrate release liner configured to cover a second portion of the second patient engagement substrate. The instructions can be provided to sequentially remove the primary patient engagement substrate release liner, secondary patient engagement substrate release liner, primary second patient engagement substrate release liner, and secondary second patient engagement substrate release liner.

The methods can include providing instructions to shave, clip, trim, chemically remove, or otherwise depilate, and clean the skin of the patient.

The methods for providing instructions can include measuring data using any of the electrodes and sensors provided on the wearable defibrillators described herein. For example, the methods can include measuring an impedance between the first and second defibrillator electrode pad. The methods can include measuring an impedance between a plurality of the one or more sensing electrodes. The methods can include analyzing the impedance between the first and second defibrillator electrode pad and the impedance between a plurality of the one or more sensing electrodes to verifying the correct placement of the first patient engagement substrate and the second patient engagement substrate. The methods can include verifying placement of the wearable defibrillator by determining a location of a plurality of low power radios integrated with the wearable defibrillator.

In some embodiments the first defibrillator electrode pad can include a first pair of electrodes. The controller can be configured to measure a first impedance between the first pair of electrodes. The controller can be configured to analyze the first impedance to determine whether the first pair of electrodes are in proper contact with the patient's skin.

In some embodiments the second defibrillator electrode pad includes a second pair of electrodes. The controller can be configured to measure a second impedance between the second pair of electrodes. The controller can be configured to analyze the second impedance to determine whether the second pair of electrodes are in proper contact with the patient's skin. The controller can be configured to measure a transthoracic impedance between the first pair of electrodes and the second pair of electrodes.

In some embodiments the wearable defibrillator includes a slip layer disposed between the housing and adhesive configured to allow relative movement between the housing and the adhesive.

In one example the wearable defibrillator includes a first sealing layer enclosing the energy source, one or more capacitors, and controller. The first sealing layer can be within the housing. The first sealing layer can contact the housing. In one example the wearable defibrillator includes a second sealing layer containing the housing.

In some embodiments the wearable defibrillator includes a first connection between the housing and the first patient engagement substrate and a second flexible connection between the housing and the first patient engagement substrate. The first connection can be on a first end of the first patient engagement substrate and the second flexible connection can be on a second end of the first patient engagement substrate that opposes the first end of the first patient engagement substrate. The second flexible connection can allow for relative movement between the second end of the first patient engagement substrate and the housing.

In some embodiments the wearable defibrillator includes a first sensing electrode release liner configured to cover the one or more sensing electrodes on the first patient engagement substrate and a first defibrillator electrode pad release liner configured to cover the defibrillator electrode pad. In some embodiments the wearable defibrillator includes a second sensing electrode release liner configured to cover the one or more sensing electrodes on the second patient engagement substrate and a second defibrillator electrode pad release liner configured to cover the second defibrillator electrode pad.

In some embodiments the wearable defibrillator housing is supported by two or more patient engagement substrates.

In some embodiments the wearable defibrillator includes an electroactive polymer. The electroactive polymer can be configured to detect a change in a morphology of the first patient engagement substrate and/or second patient engagement substrate. The electroactive polymer can configured to vibrate. The electroactive polymer can be configured to deform to change the morphology of the first and/or second patient engagement substrate.

In some embodiments the wearable defibrillator housing is configured to receive a plurality of energy sources. The energy source can include a first modular battery and a second modular battery. The first and second modular batteries can be configured to be removably received within the housing.

In some embodiments the wearable defibrillator includes a flexible connection between the housing and the first patient engagement substrate configured to support the weight of the housing and components within the housing. The flexible connection can allow for relative movement between the housing and the first patient engagement substrate. The flexible connection can include one or more electrical connections between the housing and the first patient engagement substrate. The flexible connection can include a removable and reversible connection.

In some embodiments the wearable defibrillator includes a cantilever coupled to the housing and the first patient engagement substrate.

In some embodiments the wearable defibrillator includes a first adhesive release liner configured to cover the adhesive on the first patient engagement substrate. In some embodiments the wearable defibrillator includes a second adhesive release liner configured to cover the adhesive on the second patient engagement substrate.

Figure 43A:
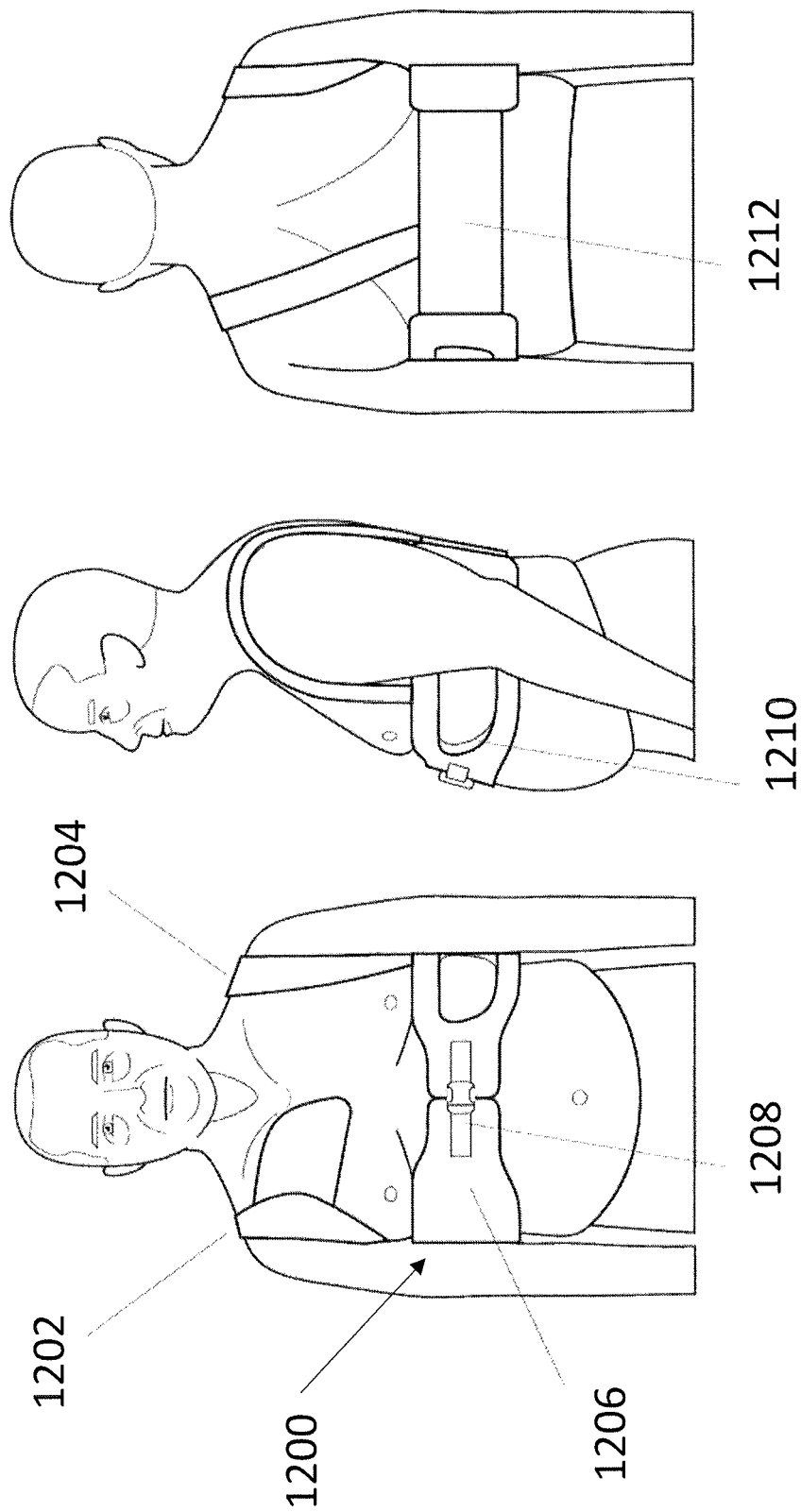
FIGS. 43A-43B illustrate a device that can be used to fit the wearable devices described herein to the patient in accordance with some embodiments.
Figure 43B:
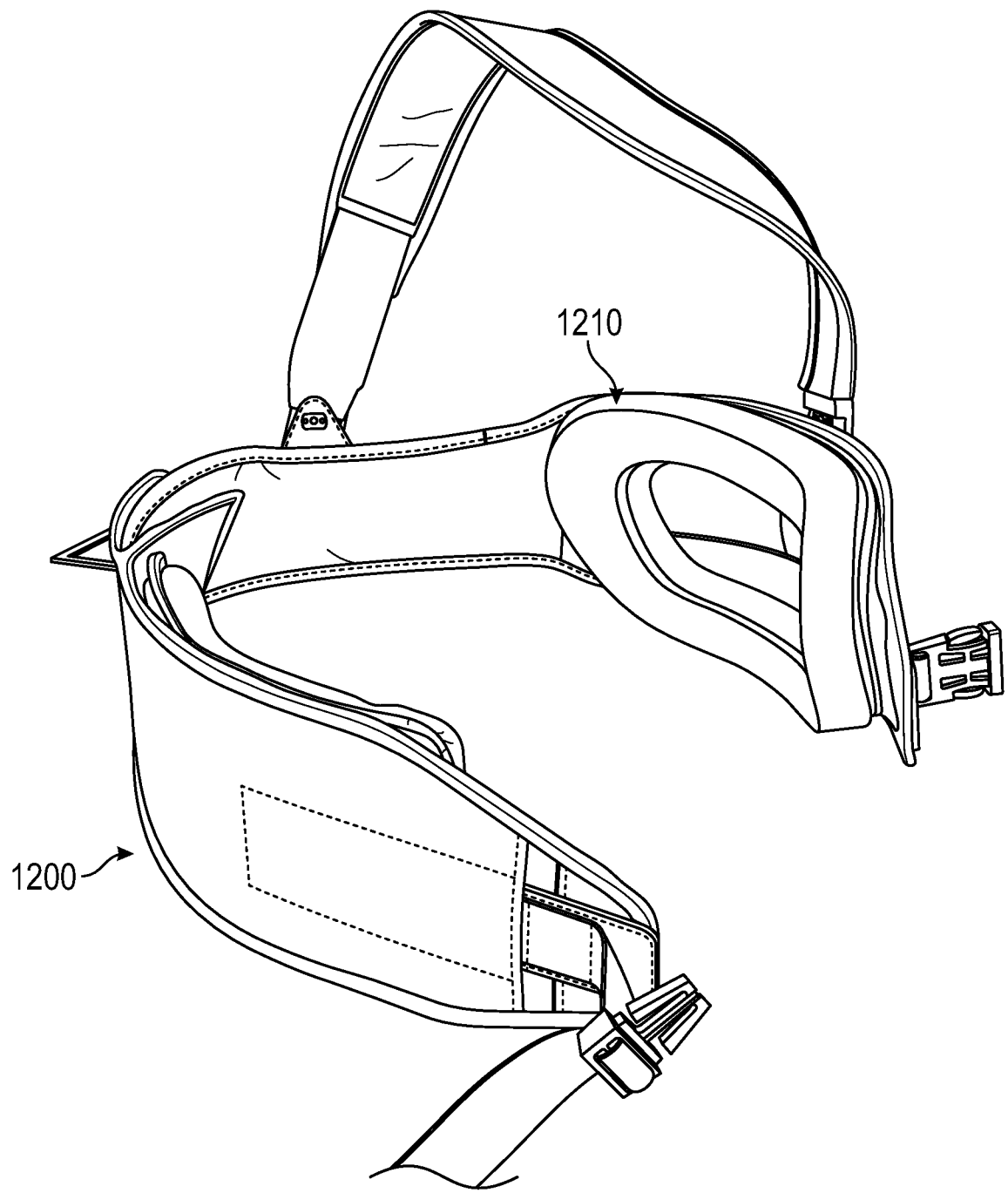

In some embodiments a fitting tool can be provided with the wearable devices described herein. The fitting tool can be part of s system with the wearable devices and can be used in methods for placing the wearable device on the patient. FIGS. 43A-43B illustrate a fitting tool 1200 that can be used to fit the wearable devices described herein to the patient in accordance with some embodiments. The fitting tool can be custom fit and sized to the individual patient. The measurements can be set and noted for future reference using a pre-defined system guide. The fitting tool 1200 can include an adjustable upper/top patch arm brace 1202 and an adjustable shoulder strap 1204 for height alignment. The upper patch of the wearable device can be stored on the main fitting tool either on the shoulder strap or the belt 1206 while the patient positions and fastens the tool on the body. The upper patch fitting tool 1200 can be sized to fit the circumference of the shoulder/armpit area of the specific patient. The height and angle of the patch in the tool can be set during an initial fitting process. The fitting tool 1200 can include a main belt 1206 for lateral chest alignment of the wearable device. The fitting tool 1200 can include an adjustable buckle strap 1208. The belt 1206 can be adjustable and extendable to fit patients with a torso circumference (at xiphoid height) from about 27" up to about 56". The fitting tool 1200 can include an inner frame 1210 with a foam support for the wearable device. The inner frame 1210 can include a complementary surface to an outer portion of the surface of the wearable devices described herein, such as the wearable defibrillators. The inner frame 1210 can engage with the wearable device to securely hold the outer portion of the surface of the wearable device with the complementary surface. The inner frame can include a foam pad with a complementary surface to the wearable device having an undercut edge such that the fitting tool and foam pad can interface with the housing modules with the undercut edge. In some instances the foam of the fitting tool 1200 can be removed from the frame to help simplify loading the device from shipping package to the fitting tool 1200. The fitting tool 1200 can include an extended back belt brace 1212. The fitting tool 1200 can be used when the device is initially provided to the patient and placed on the patient. The fitting tool 1200 and any of the belt sections included in the fitting tool 1200 can be packaged in a compact and folded arrangement.

Example 1

The moisture vapor transmission rate (MVTR) were tested for various components and wearable defibrillator patient engagement substrates described herein. Adhesive conductive hydrogels were tested and had a MVTR rate of 4,000-5,000 g/m$^2$ per day. Vapor permeable fabric materials were tested and had MVTR of 3,500-3,600 g/m$^2$ per day.

Patient engagement substrates were tested that included: adhesive, conductive hydrogels, defibrillator electrode pad, wicking layer, flexible circuit, chassis support layer, and vapor permeable outer layers. The tested MVTR rates in g/m$^2$ per day were around 1,800-1,900 for the tested patient engagement substrates.

Other combinations of materials were also tested. In another example the MVTR was tested across a carbon vinyl defibrillator electrode layer with 0.16" diameter perforations, an acrylic defibrillator electrode adhesive, a nonwoven wicking material layer, an acrylic chassis adhesive, a PVC chassis layer with a thickness of 16 mil. The MVTR was 6,000 g/m$^2$ per day for this tested configuration.

In another example the MVTR was tested across a carbon vinyl defibrillator electrode layer with 0.085" diameter perforations, an acrylic defibrillator electrode adhesive, a nonwoven wicking material layer, an acrylic chassis adhesive, a PVC chassis layer with a thickness of 16 mil. The MVTR was 6,000 g/m$^2$ per day for this tested configuration.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements, these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A wearable external defibrillator comprising:
   two or more sensing electrodes configured to engage with a patient's skin to detect a cardiac signal;
   a first defibrillator electrode pad configured to engage with the patient's skin and to deliver an electrical therapy to the patient, the first defibrillator electrode pad configured to be in continuous contact with the patient's skin;
   a first patient engagement substrate comprising an adhesive, the first defibrillator electrode pad, a first fluid transport element configured to transport fluid away from the skin to allow the wearable external defibrillator to be worn continuously, and a first vapor permeable layer;
   a second patient engagement substrate comprising a second defibrillator electrode pad, a second adhesive, a second fluid transport element in fluid communication with the second patient engagement substrate configured to transport fluid away from the skin to allow the wearable external defibrillator to be worn continuously, and a second vapor permeable layer;
   an energy source;
   one or more capacitors in electrical communication with the energy source and the first defibrillator electrode pad and the second defibrillator electrode pad;
   a controller configured to detect the cardiac signal with the two or more sensing electrodes and to charge the one or more capacitors with the energy source followed by discharging the one or more capacitors to deliver a therapeutic shock through the first defibrillator electrode pad and the second defibrillator electrode pad to the patient while the first and second patient engagement substrates are engaged with the patient, wherein the energy source, one or more capacitors, and controller are enclosed within a plurality of housings supported by at least one of the first patient engagement substrate and the second patient engagement substrate; and
   a flexible circuitry providing electrical communication between the housings.

2. The wearable defibrillator of claim 1, further comprising: one or more mechanical connections between two or more of the housings.

3. The wearable defibrillator of claim 1, wherein the flexible circuitry is adapted to receive an electrical connection from one or more of the plurality of housings.

4. The wearable defibrillator of claim 1, wherein the flexible circuitry is supported by the first patient engagement substrate.

5. The wearable defibrillator of claim 1, further comprising: a support chassis disposed between the housings and the first defibrillator electrode pad and adapted to spread a shear load of the housings.

6. The wearable defibrillator of claim 1, wherein the controller is configured to measure an impedance between a pair of electrodes selected from the group consisting of the first defibrillator electrode pad, the second defibrillator electrode pad and the two or more sensing electrodes.

7. The wearable defibrillator of claim 6, wherein the controller is configured to analyze the impedance to determine whether the pair of electrodes are in proper contact with the patient's skin.

8. The wearable defibrillator of claim 1, wherein the first defibrillator electrode pad and the second defibrillator electrode pad each comprises a conductive adhesive.

9. The wearable defibrillator of claim 1, wherein the first and second defibrillator electrode pads each comprises a plurality of perforations.

10. The wearable defibrillator of claim 1, wherein the first and second defibrillator electrode pads each comprises a carbon vinyl film, Ag/AgCl coated carbon vinyl film, or Ag coated carbon vinyl film.

11. The wearable defibrillator of claim 8, wherein the conductive adhesive comprises a conductive hydrogel.

12. The wearable defibrillator of claim 1, further comprising: a wireless radio configured to wirelessly transmit data from the wearable defibrillator.

13. The wearable defibrillator of claim 1, wherein the controller is configured to measure impedances between pairs of electrodes selected from the group consisting of the first defibrillator electrode pad, the second defibrillator electrode pad and the one or more sensing electrodes to sense impedance changes along a plurality of vectors of the patient, wherein the controller is configured to analyze the impedance changes along the plurality of vectors of the patient.

14. The wearable defibrillator of claim 1, further comprising: a tactile feedback module.

15. The wearable defibrillator of claim 14, wherein the tactile feedback module is a vibration motor.

16. The wearable defibrillator of claim 1, further comprising: a connection between the one or more of the plurality of housings and the at least one of the first patient engagement substrate and the second patient engagement substrate, the connection configured to support the weight of the plurality of housings and components within the plurality of housings.

17. The wearable defibrillator of claim 16, wherein the connection allows for relative movement between the plurality of housings and the first patient engagement substrate.

18. The wearable defibrillator of claim 16, wherein the connection further comprises one or more electrical connections between the housings and the first patient engagement substrate.

19. The wearable defibrillator of claim 16, wherein the connection comprises a removable and reversible connection.

20. The wearable defibrillator of claim 6, wherein the controller is further configured to measure the impedance using two or more discrete frequencies.

21. The wearable defibrillator of claim 20, the controller further configured to analyze the impedance measured at the two or more discrete frequencies to determine a power of the therapeutic shock for the patient based on the impedance.

22. A method of monitoring and defibrillating a patient's heart, comprising:
adhering to a first skin surface portion of the patient a first patient engagement substrate comprising a first sensing electrode and a first defibrillator electrode pad, the first defibrillator electrode pad in electrical communication with one or more capacitors and an electrical energy source sufficient to provide a defibrillating shock;
adhering to a second skin surface portion of the patient a second patient engagement substrate comprising a second sensing electrode and a second defibrillator electrode pad, the second defibrillator electrode pad in electrical communication with the one or more capacitors and the electrical energy source, the one or more capacitors and the energy source being enclosed within a plurality of housings supported by at least one of the first patient engagement substrate and the second patient engagement substrate, the plurality of housings being in electrical communication via flexible circuitry;
measuring patient data corresponding to a cardiac signal or other characteristic of the patient with the first sensing electrode and the second sensing electrode; and
analyzing the patient data to determine if the patient has an arrhythmia.

23. The method of claim 22, further comprising: sensing impedance changes along a plurality of vectors of the patient between pairs of electrodes selected from the group consisting of the first defibrillator electrode pad, the second defibrillator electrode pad the first sensing electrode and the second sensing electrode.

24. The method of claim 22, further comprising: delivering an electrical shock after determining that the patient has an arrhythmia.

25. The wearable defibrillator of claim 1, wherein the housings are each configured to reversibly receive and support one or more of the energy source, the one or more capacitors, and the controller.

26. The wearable defibrillator of claim 25, further comprising one or more connectors each configured to reversibly engage with one or more of the energy source, the one or more capacitors, and the controller, the electrical connector supported by the first patient engagement substrate, the second patient engagement substrate and/or the housings.

* * * * *